US012054781B2

(12) United States Patent
Bettegowda et al.

(10) Patent No.: US 12,054,781 B2
(45) Date of Patent: Aug. 6, 2024

(54) DETECTION OF TUMOR-DERIVED DNA IN CEREBROSPINAL FLUID

(71) Applicant: The Johns Hopkins University, Baltimore, MD (US)

(72) Inventors: Chetan Bettegowda, Perry Hall, MD (US); Kenneth W. Kinzler, Baltimore, MD (US); Bert Vogelstein, Baltimore, MD (US); Yuxuan Wang, Baltimore, MD (US); Luis Diaz, Ellicot City, MD (US); Nickolas Papadopoulos, Towson, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 15/744,299

(22) PCT Filed: Jul. 12, 2016

(86) PCT No.: PCT/US2016/041862
§ 371 (c)(1),
(2) Date: Jan. 12, 2018

(87) PCT Pub. No.: WO2017/011440
PCT Pub. Date: Jan. 19, 2017

(65) Prior Publication Data
US 2019/0002987 A1 Jan. 3, 2019

Related U.S. Application Data

(60) Provisional application No. 62/192,424, filed on Jul. 14, 2015.

(51) Int. Cl.
*C07H 21/04* (2006.01)
*C12Q 1/68* (2018.01)
*C12Q 1/6886* (2018.01)

(52) U.S. Cl.
CPC ..... *C12Q 1/6886* (2013.01); *C12Q 2600/156* (2013.01)

(58) Field of Classification Search
None
See application file for complete search history.

(56) References Cited

U.S. PATENT DOCUMENTS 9,873,917 B2 * 1/2018 Vogelstein ........... C12Q 1/6886
2012/0202207 A1 * 8/2012 Vogelstein ........... C12Q 1/6886
435/6.11

(Continued)

FOREIGN PATENT DOCUMENTS

WO WO 2012/051622 4/2012
WO WO 2014/127359 8/2014
WO WO-2014160834 A1 * 10/2014

OTHER PUBLICATIONS

Wong et al. (Cancer Research vol. 63, pp. 3866-3871, Jul. 2003) (Year: 2003).*

(Continued)

*Primary Examiner* — Jeanine A Goldberg
(74) *Attorney, Agent, or Firm* — Fish & Richardson P.C.

(57) ABSTRACT

As cell-free DNA from brain and spinal cord tumors cannot usually be detected in the blood, we assessed the cerebrospinal fluid (CSF) that bathes the CNS for tumor DNA, here termed CSF-tDNA. The results suggest that CSF-tDNA could be useful for the management of patients with primary tumors of the brain or spinal cord.

15 Claims, 38 Drawing Sheets

Specification includes a Sequence Listing.

(56) References Cited

U.S. PATENT DOCUMENTS

| | | | |
|---|---|---|---|
| 2014/0221219 A1* | 8/2014 | Vogelstein | C12Q 1/6886 506/2 |
| 2014/0227271 A1 | 8/2014 | Yan et al. | |
| 2015/0361507 A1* | 12/2015 | Yan | C12Q 1/6886 506/2 |
| 2017/0081730 A1* | 3/2017 | Vogelstein | C12Q 1/6886 |

OTHER PUBLICATIONS

Chen et al. (Molecular Therapy-Nucleic Acids, vol. 2, e109, 2013) (Year: 2013).*
Pan et al. (Clin Chem, vol. 61, No. 3, pp. 514-522, Mar. 2015) (Year: 2015).*
Wang et al. (PNAS, vol. 112, No. 31, pp. 9704-9709, Jun. 18, 2015) (Year: 2015).*
Shingyoji et al. (J. of Thoracic Oncology, vol. 6, No. 7, Jul. 2011). (Year: 2011).*
Pan et al. (Clinical Chemistry, vol. 61, No. 3, pp. 514-522, Jan. 20, 2015). (Year: 2015).*
McAllister (Primary Central Nervous System Lymphoma: A Review, pp. 210-215, 2002) (Year: 2002).*
Koelsche et al (Acta Neuropathol, vol. 126, pp. 907-915, 2013). (Year: 2013).*
Jose-Lopez et al. (JAVMA, vol. 244, No. 2, pp. 200-204, Jan. 14, 2014) (Year: 2014).*
Eichler et al. (Neurosurg Focus, vol. 5, E16, 2006) (Year: 2006).*
Bruno et al. (Abstract 3896: Recurrent TERT promoter mutations in primary central nervous system lymphoma; Proceedings: AACR 106th Annual Meeting 2015; Apr. 18-22, 2015; Philadelphia, PA) (Year: 2015).*
Shi et al. J. Mol Neurosci, vol. 46, pp. 470-475, 2012). (Year: 2012).*
Chen et al., "BEAMing and droplet digital PCR analysis of mutant IDH1 mRNA in glioma patient serum and cerebrospinal fluid extracellular vesicles.", Molecular Therapy-Nucleic Acids, vol. 2, p. e109, 2013.
Extended European Search Report in Application No. 16825025.6, dated Jan. 3, 2019, 9 pages.
Melanie Gephart, "Abstract 620: Monitoring leptomeningeal metastasis treatment response using tumor cell free DNA from cerebral spinal flui", Proceedings: AACR 106th Annual Meeting 2015, Cancer Research 2015.
Agrawal et al., "Comparative Genomic Analysis of Esophageal Adenocarcinoma and Squamous Cell Carcinoma", Cancer Discov., 2(10), pp. 899-905, 2012.
Agrawal et al., "Exome Sequencing of Head and Neck Squamous Cell Carcinoma Reveals Inactivating Mutations in NOTCH1", Science, 333(6046), pp. 1154-1157, 2011.
Allory et al., "Telomerase reverse transcriptase promoter mutations in bladder cancer: high frequency across stages, detection in urine, and lack of association with outcome", Eur. Urol., 65(2), pp. 360-366, 2014.
Bartlett F, Kortmann R, & Saran F. Medulloblastoma, Clinical oncology, 25(1): 36-45, 2013.
Bettegowda et al., "Detection of circulating tumor DNA in early- and late-stage human malignancies" , Sci. Tranls. Med., 6(224): 224ra224, 2014.
Bettegowda et al., "Exomic sequencing of four rare central nervous system tumor types", Oncotarget, 4(4), pp. 572-583, 2013.
Bettegowda et al., "Mutations in CIC and FUBP1 contribute human oligodendroglioma", Science, 333(6048), pp. 1453-1455, 2011.
Chamberlain et al., "A comparison between ventricular and lumbar cerebrospinal fluid cytology in adult patients with leptomeningeal metastases", Neuro. Oncol. 3(1), pp. 42-45, 2001.
Dawson et al., "Analysis of circulating tumor DNA to monitor metastatic breast cancer", N. Engl. J. Med., 368(13):119-1209, 2014.
Destro A, et al., "K-ras and p16(INK4A)alterations in sputum of NSCLC patients and in heavy asymptomatic chronic smokers", Lung Cancer, 44(1):23-32, 2004.
Diehl et al., "Analysis of mutations in DNA isolated from plasma and stool of colorectal cancer patients", Gastroenterology, 135(2), pp. 489-498, 2008.
Diehl et al., "Circulating mutant DNA to assess tumor dynamics", Nat. Med., 14(9): 985-990, 2008.
Gajjar A, et al., "Comparison of lumbar and shunt cerebrospinal fluid specimens for cytologic detection of leptomeningeal disease in pediatric patients with brain tumors", J. Clin. Oncol., 17(6):1825-1828, 1999.
Gajjar AJ & Robinson GW, "Medulloblastoma-translating discoveries from the bench personalized treatment", J. Pathol., 232(2):165-177, 2014.
Gajjar et al., "Molecular insights into pediatric brain tumors have the potential to transfer therapy", Clin. Cancer Res., 20(22), pp. 5630-5640, 2014.
Glass et al., "Malignant cells in cerebrospinal fluid (CSF): the meaning of a positive CSF cytology", Neurology, 29(10), pp. 1369-1375, 1979.
Horn S. et al., "TERT promoter mutations in familial and sporadic melanoma", Science, 339(6122):957-959, 2013.
Huang et al., "Highly recurrent TERT promoter mutations in human melanoma", Science, 339(6122), pp. 957-959, 2013.
Hubers et al., "Molecular sputum analysis for the diagnosis of lung cancer", Br. J. Cancer, 1009(3), pp. 530-537, 2013.
International Search Report and Written Opinion in International Application No. PCT/US2016/041862, dated Oct. 20, 2016.
Khwaja et al., "Proteomic identification of biomarkers in the cerebrospinal fluid (CSF) of astrocytoma patients", J. Proteome. Res., 6(2), pp. 559-570, 2007.
Killela et al., "TERT promoter mutations occur frequently in gliomas and a subset of tumors derived from cells with low rates of self-renewal", Proc. Natl. Acad. Sci. USA, 110(15), pp. 6021-6026, 2013.
Kinde et al., "Detection and quantification of rare mutations with massively parallel sequencing", Proc. Natl. Acad. Sci. USA, 108(23), pp. 9530-9535, 2011.
Kinde et al., "TERT promoter mutations occur early in urothelial neoplasia and are biomarkers of early disease and disease recurrence in urine", Cancer Res. 73(24), pp. 7162-7167, 2013.
Kros et al., "Circulating glioma biomakers", Neuro. Oncol., 17(3), pp. 343-360, 2014.
Krueger et al., "Everolimus for subendymal giant-cell astrocytomas in tuberous sclerosis", N. Engl. J. Med., 363(19), pp. 1801-1811, 2010.
Macarthur et al., "Detection of brain tumor cells in the peripheral blood by a telomerase promoter-based assay", Cancer Res. 74(8), pp. 2152-2159, 2014.
Mack et al., "Epigenomic alterations define lethal CIMP-positive ependymomas of infancy", Nature, 506(7489), pp. 445-450, 2014.
Martignetti et al., "Personalized ovarian cancer disease surveillance and detection of candidate therapeutic drug target in circulating tumor DNA", Neoplsia, 16(1), pp. 97-103, 2014.
Moreno L, et al., "Utility of cerebrospinal fluid cytology in newly diagnosed childhood ependymoma", J. Pediatr. Hematol. Oncol., 32(6):515-518, 2010.
Muller C, et al., "Hematogenous dissemination of glioblastoma multiforme", Sci. Transl. Med., 6(247): 247ra101, 2014.
Newman AM, et al., "An ultrasensitive method for quantitating circulating tumor DNA with broad patient coverage", Nat. Med. 20(5): 548-554, 2014.
Olar et al., "Using the molecular classification of glioblastoma to inform personalized treatment", J. Pathol. 232(2) pp. 165-177, 2014.
Ostrom QT, et al., "CBTRUS statistical report: Primary brain and central nervous system tumors diagnosed in the United States in 2006-2010", 56 pages, 2013.
Pan et al., "Brain tumor mutations detected in cerebral spinal fluid", Clin. Chem., 61(3), pp. 514-522, 2015.
Preusser et al., "CSF and laboratory analysis (tumor markers)", Handbook of clinical neurology, 104: 143-148, 2012.

(56) References Cited

OTHER PUBLICATIONS

Ralla B. et al., "Nucleic acid-based biomarkers in body fluids of patients with urologic malignancies", Critical Reviews in Clinical Laboratory Sciences, 51(4): 200-231, 2014.
Rhodes et al., "PCR-detection of tumor-derived p53 DNA in cerebrospinal fluid", American Journal of Clinical Pathology, vol. 103, No. 4, pp. 404-408, 1995.
Roy et al., "Protein biomarker identification in the CSF of patients with CNS lymphoma", J. Clin. Oncol., 26(1), pp. 96-105, 2008.
Rudin et al., "Treatment of medulloblastoma subgroups that are enriched for specific genetic alterations", J. Clin. Oncol., 24(12), pp. 1924-1931, 2006.
Samuel et al., "Proteomic analyses of CSF aimed at biomarker development for pediatric brain tumors", J. Neurooncol, 118(2): 225-238, 2014.
Sidransky D, et al., "Identification of p53 gene mutations in bladder cancers and urine samples", Science, 252(5006): 706-709, 1991.
Sidransky D, et al., "Identification of ras oncogene mutations in the stool of patients with curable colorectal tumors", Science, 256(5053): 102-105, 1992.
Sullivan et al., "Brain tumor cells in circulation are enriched for mesenchymal gene expression", Cancer Res., 74(8), pp. 1299-1309, 2014.
Thomas et al., "Predictive biomarkers in adult gliomas: the present and the future", Curr. Opin. Oncol., 25(6):689-694, 2013.
Thompson et al., "Genomics identifies medullolastoma subgroups that are enriched for specific genetic alertations", J. Clin. Oncol., 24(12), pp. 1924-1931, 2006.
Van Mieghem E. et al., "Defining pseudoprogression in glioblastoma multiforme", European Journal of Neurology: The Official Journal of the European Federation of Neurological Societies, 20(10): 1335-1341, 2013.
Von Hoff et al., "Medulloblastoma", Current treatment options in neurology, 14(4): 416-426, 2012.
Wang et al., "Detection of tumor-derived DNA in cerebrospinal fluid of patients with primary tumors of the brain and spinal cord", PNAS, vol. 112, No. 31, pp. 9704-9709, 2015.
Weston et al., "Detection of cancer cells in the cerebrospinal fluid: current methods and future directions", Fluids and barriers of the CNS, 8: 14, 9 pages, 2011.
Wong et al., "Detection of mitochondrial DNA mutations in the tumor and cerebrospinal fluid of medulloblastoma patients", Cancer Research, vol. 63, pp. 386-3871, 2003.
Woodworth et al., "Histopathological correlates with survival in reoperated glioblastomas", J. Neurooncol, 113(3), pp. 485-493, 2013.
Zhang et al., "Somatic mutations of SUZ12 in malignant peripheral nerve sheath tumors", Nat. Genet., 46(11), pp. 1170-1172, 2014.
Bougel et al., "Methylation of the hTERT promoter: a novel cancer biomarker for leptomeningeal metastasis detection in cerebrospinal fluids," Clin. Cancer Res., Feb. 2013, 19(8):2216-2223.
Kinde et al., "Evaluation of DNA from the Papanicolaou test to detect ovarian and endometrial cancers," Sci Transl. Med., Jan. 2013, 5(167):167ra4, 10 pages.
Rudin et al., "Treatment of medulloblastoma with hedgehog pathway inhibitor GDC-0449," N. Engl. J. Med., Sep. 2009, 361(12):1173-1178.
Vogelstein et al., "Cancer Genome Landscapes," Science, Mar. 2013, 339(6127):1546-1558.

\* cited by examiner

Fig. 3

Table 1. Patient Demographics

| Patient ID | Gender | Recurrence | Age (years) | Race | Pre-op Symptoms | Duration of Symptoms (months) | Hydrocephalus | Diagnosis | Tumor Grade | Enhancing on CT or MRI | Tumor Location | Size (cubic cm) | Location of Where CSF was Obtained | Abutting CSF Space | Tumor-Derived DNA detected in CSF |
|---|---|---|---|---|---|---|---|---|---|---|---|---|---|---|---|
| CGLI 02 | Female | No | 33 | W | Dysesthesias, urinary retention | 33 | No | Glioma | WHO II, diffuse astrocytoma | No | T11 spinal cord | 2 x 1 x 1 | Spinal sub-arachnoid space | Yes | Not detected |
| CGLI 03 | Male | No | 13 | W | Incidental | Not applicable | No | Anaplastic astrocytoma | WHO III, anaplastic astrocytoma | Yes | Pons | 3 x 3.2 x 3.6 | Basal cistern | Yes | Positive |
| CGLI 06 | Female | No | 13 | AA | Headache, vision loss | 2 | Yes | Pilocytic astrocytoma | WHO I, pilocytic astrocytoma | Yes | Cerebellar vermis | 4.9 x 4.5 x 5.6 | Basal cistern | Yes | Positive |
| CGLI 101 | Male | Yes | 49 | W | Headache, nausea, vomiting | NA | Yes | Glioblastoma | WHO IV, glioblastoma | Yes | Cerebellar vermis | 2.6 x 2.0 x 1.6 | Basal cistern | Yes | Positive |
| CGLI 11 | Female | No | 50 | W | Dysesthesias, numbness | 36 | No | Spinal ependymoma | WHO II, ependymoma | Yes | C7-T3 spinal cord | 5.3 x 1 x 1.2 | Spinal sub-arachnoid space | Yes | Positive |
| CGLI 12 | Male | No | 5 | W | Headache, vomiting | 1 | Yes | Intracranial ependymoma | WHO II, ependymoma | Yes | 4th ventricle | 4.1 x 4.2 x 3.8 | Basal cistern | Yes | Positive |
| CGLI 13 | Male | No | 27 | W | Back pain, sciatica | 15 | No | Myxopapillary ependymoma | WHO I, myxopapillary ependymoma | NA | L2-3 spinal cord | NA | Spinal sub-arachnoid space | NA | Positive |
| CGLI 14 | Female | No | 62 | W | Back pain | 5 | No | Intramedullary spinal cord lesion | low-grade neoplasm | Yes | T7-9 spinal cord | 4.5 x 0.8 x 1.2 | Spinal sub-arachnoid space | Yes | Positive |
| CGLI 15 | Male | No | 52 | W | Neck pain | 1 | No | Spinal ependymoma | WHO II, ependymoma | Yes | C3-4 spinal cord | 2.1 x 0.9 x 1.2 | Spinal sub-arachnoid space | No | Not detected |
| CGLI 20 | Female | No | 14 | W | Headache, vomiting | 3 | Yes | Medulloblastoma | WHO IV, medulloblastoma | Yes | 4th ventricle | 3.4 x 3.2 x 2.6 | Basal cistern | Yes | Positive |
| CGLI 22 | Female | No | 18 | A | Headache, vomiting | 3 | No | Pilocytic astrocytoma | WHO I, pilocytic astrocytoma | Yes | Cerebellar hemisphere | 5 x 4.5 x 4.3 | Basal cistern | No | Not detected |
| CGLI 25 | Female | No | 72 | W | Back pain, arm pain | 3 | No | Myxopapillary ependymoma | WHO I, myxopapillary ependymoma | Yes | L2-3 spinal cord | 4.3 x 1.2 x 0.7 | Spinal sub-arachnoid space | Yes | Positive |
| CGLI 254 | Male | Yes | 7 | W | Headache, ataxia, vomiting | NA | Yes | Medulloblastoma | WHO IV, medulloblastoma | Yes | 4th ventricle | 1.7 x 1.2 x 1.2 | Basal cistern | Yes | Positive |
| CGLI 26 | Female | No | 46 | W | Left leg pain | 13 | No | Intramedullary spinal cord tumor | WHO II, infiltrating astrocytoma w/ oligodendroglial features | No | C3-6 spinal cord | 5 x 1.4 x 1.2 | Spinal sub-arachnoid space | Yes | Positive |
| CGLI 28 | Female | No | 79 | A | Left arm weakness | 3 | No | Anaplastic astrocytoma | WHO III, anaplastic astrocytoma | Yes | Right frontal/butterfly | 4.4 x 5.7 x 5.8 | Ventricle | Yes | Positive |
| CGLI 29 | Male | Yes | 18 | W | Neck pain | 28 | No | Glioblastoma | WHO IV, glioblastoma | Yes | C4-6 spinal cord | 3.1 x 1.1 | Spinal sub-arachnoid space | Yes | Positive |
| CGLI 31 | Male | No | 74 | AA | Seizure | 0.5 | No | Glioblastoma | WHO IV, glioblastoma | Yes | Right frontal/butterfly | 4.5 x 5.2 x 4.3 | Ventricle | Yes | Positive |

Fig. 3 (continued)

| ID | Sex | | Age | Race | Symptoms | Duration (mo) | | Diagnosis | WHO grade | | Location | Size (cm) | Location 2 | | Result |
|---|---|---|---|---|---|---|---|---|---|---|---|---|---|---|---|
| CGLI 35 | Male | No | 70 | AA | Memory loss | 2 | No | Glioblastoma | WHO IV, glioblastoma | Yes | Right temporal | 6.1 x 4.3 x 3.5 | Ventricle | Yes | Positive |
| CGLI 36 | Male | No | 11 | W | Back pain | 2 | No | Spinal cord glioblastoma | WHO IV, glioblastoma | Yes | T10-L1 spinal cord | 6.5 x 1.7 x 2.2 | Spinal sub-arachnoid space | Yes | Positive |
| CGLI 39 | Male | No | 56 | W | Paresthesias | 3 | No | Intramedullary spinal cord tumor | WHO II, low grade glioma likely ependymoma | Yes | C2-3 spinal cord | 1.7 x 1.1 x 1.6 | Spinal sub-arachnoid space | No | Not detected |
| CGLI 40 | Male | No | 7 | W | Headache, ataxia | 5 | No | Medulloblastoma | WHO IV, medulloblastoma | Yes | 4th ventricle | 4.0 x 4.0 x 4.8 | Basal cistern | Yes | Positive |
| CGLI 41 | Male | Yes | 34 | W | Gait imbalance, incoordination | 0.5 | No | Glioblastoma | WHO IV, glioblastoma | Yes | Cerebellar hemisphere | 4.0 x 3.0 x 2.9 | Basal cistern | Yes | Positive |
| CGLI 42 | Female | No | 31 | W | Back pain | 24 | No | Spinal ependymoma | WHO II, ependymoma | NA | NA | NA | Spinal sub-arachnoid space | NA | Positive |
| CGLI 43 | Male | Yes | 66 | W | Dysesthesias | 12 | No | Low grade glioma | WHO II, low-grade glioma | Yes | T10 spinal cord | 3.8 x 1.4 x 1.4 | Spinal sub-arachnoid space | Yes | Not detected |
| CGLI 44 | Female | No | 6 | A | Headache, vomiting | 2 | Yes | Pilocytic astrocytoma | WHO I, pilocytic astrocytoma | Yes | Cerebellar vermis | 3.4 x 3.8 x 3.4 | Basal cistern | No | Not detected |
| CGLI 47 | Female | Yes | 71 | W | Headache | 2 | No | Glioblastoma | WHO IV, glioblastoma | Yes | Right temporal | 6.0 x 3.7 x 3.3 | Ventricle | Yes | Positive |
| CGLI 48 | Male | No | 56 | W | Blurry vision, mental status change | 2 | No | Glioblastoma | WHO IV, glioblastoma | Yes | Left temporal | 6.1 x 7.7 x 4.9 | Ventricle | Yes | Positive |
| CGLI 50 | Female | No | 69 | W | Vision | 1 | No | Glioblastoma | WHO IV, glioblastoma | Yes | Right temporal | 5.1 x 5.0 x 3.8 | Ventricle | Yes | Positive |
| CGLI 51 | Female | No | 84 | W | Asymptomatic | Not applicable | No | Glioblastoma | WHO IV, glioblastoma | Yes | Right frontal | 4.0 x 3.3 x 2.9 | Ventricle | Yes | Positive |
| CGLI 55 | Male | No | 7 | ME | Headache, difficulty walking | 1 | No | Brainstem glioblastoma | WHO IV, glioblastoma | Yes | Midbrain | 3.1 x 3.9 x 3.4 | Basal cistern | Yes | Positive |
| CGLI 56 | Male | No | 3 | W | Headache, difficulty walking | 1 | Yes | Medulloblastoma | WHO IV, medulloblastoma | Yes | 4th ventricle | 4.1 x 4.2 x 4.0 | Basal cistern | Yes | Positive |
| CGLI 58 | Male | No | 32 | ME | Numbness, myelopathy | 24 | No | Diffuse astrocytoma | WHO II, diffuse astrocytoma | No | T2-4 spinal cord | 5.1 x 1.9 x 1.2 | Spinal sub-arachnoid space | Yes | Not detected |
| CGLI 60 | Female | No | 9 | W | Headache | 3 | No | Medulloblastoma | WHO IV, medulloblastoma | Yes | 4th ventricle | 2.4 x 2.2 x 2.0 | Basal cistern | Yes | Positive |
| CGLI 61 | Female | No | 12 | W | Headache, nausea, vomiting | 1 | No | Pilocytic astrocytoma | WHO I, pilocytic astrocytoma | Yes | Cerebellar vermis | 5.5 x 5.3 x 5.2 | Basal cistern | Yes | Not detected |
| CGLI 63 | Male | No | 22 | M | Headache, vomiting, ataxia | 1 | No | Medulloblastoma | WHO IV, medulloblastoma | Yes | Cerebellum | 3.0 x 2.2 x 2.0 | Basal cistern | No | Not detected |

W = White, AA = African American, A = Asian, ME = Middle Eastern, NA = Not available

Fig. 4

Table 2. Mutations detected in the CSF and tumor of each patient

| Patient ID | Volume of CSF Analyzed (ml) | DNA in CSF (ng) | Sequencing Method* | Mutation | Location | Gene | Transcript | Protein | cDNA | Mutant Allele Fraction in Tumor | Mutant Allele Fraction in CSF |
|---|---|---|---|---|---|---|---|---|---|---|---|
| CGLI 02 | 4 | 245 | WES | NM_144631.5 (ZNF513):c.413C>T | Exon | ZNF513 | NM_144631.5 | p.P138L | c.413C>T | 49% | Not detected |
| CGLI 03 | 7 | 314 | WES | NM_181523.2 (PIK3R1):c.1690A>G | Exon | PIK3R1 | NM_181523.2 | p.N564D | c.1690A>G | 39% | 0.11% |
| CGLI 06 | 8 | 148 | WES | NR_024804.1 (CLCA3P):c.446G>A | Exon | CLCA3P | NR_024804.1 | p.R149Q | c.446G>A | 36% | 0.2% |
| CGLI 101 | 3.5 | 14 | Panel | NM_000546.5 (TP53):c.731G>A | Exon | TP53 | NM_000546.5 | p.G244D | c.731G>A | 36% | 0.9% |
| CGLI 11 | 5 | 290 | WES | NM_133450.3 (ANKS3):c.1738G>A | Exon | ANKS3 | NM_133450.3 | p.E580K | c.1738G>A | 47% | 0.3% |
| CGLI 12 | 5 | 71 | WES | NM_003531.2 (HIST1H3C):c.83T>A | Exon | HIST1H3C | NM_003531.2 | p.K28M | c.83T>A | 44% | 0.2% |
| CGLI 13 | 1.5 | 6 | WES | NM_149965.1 (TTC16):c.1016T>A | Exon | TTC16 | NM_149965.1 | p.V339E | c.1016T>A | 46% | 1.1% |
| CGLI 14 | 7.5 | 187 | Panel | NM_000546.5 (TP53):c.638G>A | Exon | TP53 | NM_000546.5 | p.R213Q | c.638G>A | 59% | 19.6% |
| CGLI 15 | 5 | 482 | WES | NM_004990.3 (MARS):c.1487C>T | Exon | MARS | NM_004990.3 | p.T496I | c.1487C>T | 13% | Not detected |
| CGLI 20 | 3 | 127 | WES | NM_198229.2 (RGS12):c.2980C>T | Exon | RGS12 | NM_198229.2 | p.R994W | c.2980C>T | 52% | 52.6% |
| CGLI 22 | 5 | 8 | WES | NM_001080522.2 (CC2D2A):c.1938G>A | Exon | CC2D2A | NM_001080522.2 | p.W646X | c.1938G>A | 54% | Not detected |
| CGLI 25 | 10 | 253 | WES | NM_001795.3 (CDH5):c.1211G>A | Exon | CDH5 | NM_001795.3 | p.S404N | c.1211G>A | 50% | 0.3% |
| CGLI 254 | 2.5 | 168 | WES | NM_021140.2 (KDM6A):c.4153C>T | Exon | KDM6A | NM_021140.2 | p.Q1385X | c.4153C>T | 91% | 77.3% |
| CGLI 26 | 7 | 20 | Panel | NM_005896.2 (IDH1):c.394C>T | Exon | IDH1 | NM_005896.2 | p.R132C | c.394C>T | 43% | 0.3% |
| CGLI 28 | 1 | 2361 | Panel | NM_005896.2 (IDH1):c.395G>A | Exon | IDH1 | NM_005896.2 | p.R132H | c.395G>A | 33% | 33.0% |
| CGLI 29 | 3.5 | 206 | Panel | NM_000546.5 (TP53):c.742C>T | Exon | TP53 | NM_000546.5 | p.R248W | c.742C>T | 69% | 0.2% |
| CGLI 31 | 4 | 1416 | Panel | NM_198253.2 (TERT):c.1-124C>T | Promoter | TERT | NM_198253.2 | NA | c.1-124C>T | 37% | 8.2% |
| CGLI 35 | 2.5 | 432 | Panel | NM_198253.2 (TERT):c.1-124C>T | Promoter | TERT | NM_198253.2 | NA | c.1-124C>T | 46% | 1.4% |
| CGLI 38 | 5.5 | 448 | Panel | NM_000546.5 (TP53):c.742C>T | Exon | TP53 | NM_000546.5 | p.R248W | c.742C>T | 65% | 14.3% |
| CGLI 39 | 8.5 | 154 | WES | NM_000268.3 (NF2):c.592C>T | Exon | NF2 | NM_000268.3 | p.R198X | c.592C>T | 88% | Not detected |
| CGLI 40 | 1.5 | 1169 | WES | NM_000388.3 (CASR):c.2549G>T | Exon | CASR | NM_000388.3 | p.A850V | c.2549G>T | 45% | 2.8% |
| CGLI 41 | 4.25 | 87 | Panel | NM_000546.5 (TP53):c.396G>C | Exon | TP53 | NM_000546.5 | p.K132N | c.396G>C | 43% | 1.4% |
| CGLI 42 | 0.75 | 20 | WES | NM_001848.2 (COL6A1):c.1417G>A | Exon | COL6A1 | NM_001848.2 | p.G473R | c.1417G>A | 39% | 0.5% |
| CGLI 43 | 4.5 | 100 | WES | NM_000268.3 (NF2):c.1009C>T | Exon | NF2 | NM_000268.3 | p.Q337* | c.1009C>T | 61% | Not detected |
| CGLI 44 | 1.5 | 64 | WES | NM_001004439.1 (ITGA11):c.2140C>T | Exon | ITGA11 | NM_001004439.1 | p.R714* | c.2140C>T | 16% | Not detected |
| CGLI 47 | 6.8 | 29 | Panel | NM_198253.2 (TERT):c.1-124C>T | Promoter | TERT | NM_198253.2 | NA | c.1-124C>T | 44% | 22.1% |
| CGLI 48 | 5 | 1400 | Panel | NM_198253.2 (TERT):c.1-124C>T | Promoter | TERT | NM_198253.2 | NA | c.1-124C>T | 52% | 1.0% |
| CGLI 50 | 5.5 | 520 | Panel | NM_198253.2 (TERT):c.1-124C>T | Promoter | TERT | NM_198253.2 | NA | c.1-124C>T | 47% | 18.8% |

Fig. 4 (continued)

| | | Panel | | | | | | |
|---|---|---|---|---|---|---|---|---|
| CGL: 51 | 0.75 | 64 | NM_198253.2 (TERT):c.1-124C>T | Promoter | TERT | NM_198253.2 | NA | c.1-124C>T | 10% | 5.9% |
| CGL: 55 | 9 | 146 | NM_000314.4 (PTEN):c.388C>T | Exon | PTEN | NM_000314.4 | p.R130* | c.388C>T | 66% | 33.2% |
| CGL: 56 | 6.5 | 1155 | NM_014691.2 (AQR):c.17464delT | Exon | AQR | NM_014691.2 | p.P5826fs | c.17464delT | 39% | 1.8% |
| CGL: 58 | 9 | 90 | NM_052853.3 (ADCK2):c.1057T>A | Exon | ADCK2 | NM_052853.3 | p.F353I | c.1057T>A | 23% | Not detected |
| CGL: 60 | 8 | 1335 | NM_004687.4 (MTMR4):c.2110C>G | Exon | MTMR4 | NM_004687.4 | p.L704V | c.2110C>G | 40% | 18.7% |
| CGL: 61 | 3 | 99 | NM_001122679.1 (TENM2):c.799G>A | Exon | TENM2 | NM_001122679.1 | p.A267T | c.799G>A | 21% | Not detected |
| CGL: 63 | 4 | 411 | NM_000264.3 (PTCH1):c.746+1C>A | Splice Site | PTCH1 | NM_000264.3 | NA | c.746+1C>A | 71% | Not detected |

WES = Whole-exome sequencing; Panel = Directed sequencing of 130 to 139 of IDH1, codons 126 to 155, 144 to 178, and 250 to 262 of IDH2, all coding exons of TP53, and the TERT promoter (see Materials and Methods)

Fig. 5A

Table 3A. Associations between clinical characteristics and levels of CSF-tDNA

| | All patients (N=35) | CSF Undetected (N=9) | CSF Detected (N=26) | P-value |
|---|---|---|---|---|
| Age: Median (Range) | 32 (3 - 84) | 32 (6 - 66) | 32.5 (3 - 84) | 0.85 |
| Gender: | | | | |
| Female: # (%) | 16 (46) | 4 (44) | 12 (46) | 1 |
| Male: # (%) | 19 (54) | 5 (55) | 14 (54) | |
| Recurrent: | | | | |
| No: # (%) | 29 (83) | 8 (89) | 21 (81) | 1 |
| Yes: # (%) | 6 (17) | 1 (11) | 5 (19) | |
| Race: | | | | |
| A: # (%) | 3 (9) | 2 (22) | 1 (4) | |
| AA: # (%) | 3 (9) | 0 (0) | 3 (12) | 0.06 |
| ME: # (%) | 3 (9) | 2 (22) | 1 (4) | |
| W: # (%) | 26 (74) | 5 (56) | 21 (81) | |
| Hydrocephalus: | | | | |
| No: # (%) | 28 (80) | 8 (89) | 20 (77) | 0.65 |
| Yes: # (%) | 7 (20) | 1 (11) | 6 (23) | |
| Tumor Grade: | | | | |
| 1: # (%) | 6 (17) | 3 (33) | 3 (12) | |
| 2: # (%) | 9 (26) | 5 (56) | 4 (15) | 0.01 |
| 3: # (%) | 2 (6) | 0 (0) | 2 (8) | |
| 4: # (%) | 17 (49) | 1 (11) | 16 (62) | |
| NA: # (%) | 1 (3) | 0 (0) | 1 (4) | |
| Tumor Grade: | | | | |
| 1 and 2: # (%) | 15 (43) | 8 (89) | 7 (27) | 0.004 |
| 3 and 4: # (%) | 19 (54) | 1 (11) | 18 (69) | |
| NA: # (%) | 1 (3) | 0 (0) | 1 (4) | |
| Enhancing CT or MRI: | | | | |
| No: # (%) | 3 (9) | 2 (22) | 1 (4) | 0.17 |
| Yes: # (%) | 30 (86) | 7 (78) | 23 (88) | |
| NA: # (%) | 2 (6) | 0 (0) | 2 (8) | |
| Tumor Location: | | | | |
| Infratentorial: # (%) | 14 (40) | 4 (44) | 10 (38) | 0.16 |
| Spinal: # (%) | 13 (37) | 5 (56) | 8 (31) | |
| Supratentorial: # (%) | 8 (23) | 0 (0) | 8 (31) | |
| Abutting CSF Space: | | | | |
| No: # (%) | 5 (14) | 5 (56) | 0 (0) | < 0.001 |
| Yes: # (%) | 28 (80) | 4 (44) | 24 (92) | |
| NA: # (%) | 2 (6) | 0 (0) | 2 (8) | |
| Sequencing Method: | | | | |
| Panel: # (%) | 13 (37) | 0 (0) | 13 (50) | 0.01 |
| WES: # (%) | 22 (63) | 9 (100) | 13 (50) | |

Fig. 5A (continued)

| Location: | | | | |
|---|---|---|---|---|
| Exon: # (%) | 28 (80) | 8 (89) | 20 (77) | 0.1 |
| Promoter: # (%) | 6 (17) | 0 (0) | 6 (23) | |
| Splice Site: # (%) | 1 (3) | 1 (11) | 0 (0) | |
| Location: | | | | |
| Promoter: # (%) | 6 (17) | 0 (0) | 6 (23) | 0.3 |
| Exon and Splice Site: # (%) | 29 (83) | 9 (100) | 20 (77) | |
| Symptom Duration: | | | | |
| Median (Range) | 3 (0.5 - 36) | 3 (1 – 33) | 2.5 (0.5 – 36) | 0.65 |
| Tumor Size: | | | | |
| Median (Range) | 34.8 (2 – 230) | 11.6 (2 – 152) | 37.4 (2.45 – 230) | 0.41 |
| CSF Volume, ml: | | | | |
| Median (Range) | 5 (0.75 – 10) | 4.5 (1.5 – 9) | 5 (0.75 – 10) | 0.88 |
| Quantity of DNA in CSF, ng: | | | | |
| Median (Range) | 168 (6 – 2361) | 100 (8 – 482) | 196 (6 – 2361) | 0.03 |
| Mutant Allele Fraction in Tumor: | | | | |
| Median (Range) | 0.45 (0.1 – 0.91) | 0.49 (0.13 – 0.80) | 0.44 (0.10 – 0.91) | 0.68 |

NA = not available, WES = Whole-exome sequencing, Panel = Directed sequencing of 130 to 139 of *IDH1*, codons 126 to 155, 144 to 178, and 250 to 262 of *IDH2*, all coding exons of *TP53*, and the *TERT* promoters (see Materials and Methods)

Fig. 5B

Table 3B. Associations between clinical characteristics and levels of CSF-tDNA

| | Odds Ratio (95% CI) | P-value |
|---|---|---|
| Univariate Logistic Regression | | |
| Gender: Female vs. Male | 1.07 (0.23 – 4.92) | 0.93 |
| Recurrent: Yes vs. No | 1.91 (0.19 – 18.93) | 0.58 |
| Race: | | |
|   A vs. W | 0.15 (0.01 – 1.92) | 0.15 |
|   AA vs. W | 1.79 (0.05 – 62.48) | 0.75 |
|   ME vs. W | 0.15 (0.01 – 1.92) | 0.15 |
|   AA vs. A | 11.67 (0.19 – 736) | 0.25 |
|   ME vs. A | 1.00 (0.04 – 27.27) | 1 |
|   ME vs. AA | 0.09 (0.001 – 5.40) | 0.25 |
| Hydrocephalus: Yes vs. No | 2.40 (0.25 – 23.24) | 0.45 |
| Tumor Grade: (3 and 4) vs. (1 and 2) | 20.57 (2.16 – 196) | 0.01 |
| Enhancing Imaging: Yes vs. No | 6.57 (0.52 – 83.75) | 0.15 |
| Tumor Location: | | |
|   Spinal vs. Infratentorial: | 0.66 (0.13 – 3.27) | 0.61 |
|   Supratentorial vs. Infratentorial: | 7.29 (0.29 – 185) | 0.23 |
|   Supratentorial vs. Spinal | 11.0 (0.44 – 276) | 0.14 |
| Abutting CSF Space: Yes vs. No | 59.9 (2.14 – 1669) | 0.02 |
| Sequencing Method: Panel vs. WES | 19.0 (0.90 – 401) | 0.06 |
| Location: Promoter vs. (Exon and Splice Site) | 6.03 (0.25 – 148) | 0.27 |
| Age: | 1.01 (0.98 – 1.04) | 0.64 |
| Symptom Duration: | 0.98 (0.91 – 1.06) | 0.63 |
| Tumor Size: | 1.01 (0.99 – 1.02) | 0.41 |
| CSF Volume: | 0.98 (0.72 – 1.32) | 0.88 |
| Quantity of DNA in CSF: | 1.00 (1.00 – 1.01) | 0.2 |
| Mutant Allele Fraction in Tumor: | 3.55 (0.04 – 298) | 0.58 |
| | | |
| Multivariate Logistic Regression | | |
| Tumor Grade: (3 and 4) vs. (1 and 2) | 26.51 (1.45 – 485) | 0.03 |
| CSF Space: Yes vs. No | 90.59 (1.07 – 7670) | 0.05 |

W = White, AA = African American, A = Asian, ME = Middle Eastern, NA = Not available, WES = Whole-exome sequencing, Panel = Directed sequencing of 130 to 139 of *IDH1*, codons 126 to 155, 144 to 178, and 250 to 262 of *IDH2*, all coding exons of *TP53*, and the *TERT* promoter (see Materials and Methods)

TABLE 4. DETECTION OF CSF-tDNA USING WHOLE-EXOME SEQUENCING (WES)

| PATIENT | SAMPLE TYPE | GENOMIC COORDINATE | MUTATION | DISTINCT COVERAGE (SAFE-SEQS) | % MUTANT (SAFE-SEQS) | DISTINCT COVERAGE (WES) | % MUTANT (WES) |
|---|---|---|---|---|---|---|---|
| CGL103 | CSF | CHR5:67591097 | PIK3R1 P.N564D, C.A1690G | 57,921 | 0.1% | 76 | 0.0% |
| | NORMAL | CHR5:67591097 | PIK3R1 P.N564D, C.A1690G | 284 | 0.0% | 61 | 0.0% |
| | PRIMARY TUMOR | CHR5:67591097 | PIK3R1 P.N564D, C.A1690G | 377 | 38.7% | 147 | 12.9% |
| CGL129 | CSF | CHR17:7577539 | TP53 P.R248W, C.C742T | 13,964 | 0.2% | 64 | 0.0% |
| | NORMAL | CHR17:7577539 | TP53 P.R248W, C.C742T | NA | 0.0% | 55 | 0.0% |
| | PRIMARY TUMOR | CHR17:7577539 | TP53 P.R248W, C.C742T | 6,418 | 69.0% | 58 | 70.7% |
| CGL136 | CSF | CHR17:7577539 | TP53 P.R248W, C.C742T | 376,434 | 14.3% | 74 | 9.5% |
| | NORMAL | CHR17:7577539 | TP53 P.R248W, C.C742T | 57,818 | 0.0% | 75 | 0.0% |
| | PRIMARY TUMOR | CHR17:7577539 | TP53 P.R248W, C.C742T | 44,981 | 65.0% | 25 | 72.0% |
| CGL155 | CSF | CHR10:89692904 | PTEN P.R130*, C.C388T | 251,609 | 33.1% | 63 | 42.9% |
| | PRIMARY TUMOR | CHR10:89692904 | PTEN P.R130*, C.C388T | 91,515 | 65.9% | 56 | 66.1% |

GENOMIC COORDINATES REFER TO THE HUMAN REFERENCE GENOME HG19 RELEASE (GENOME REFERENCE CONSORTIUM GRCH37, FEB 2009)

Table S2. Mutations identified in whole-exome sequencing

| Sample | Gene Symbol | Gene Description | Transcript Accession | Nucleotide (genomic) | Amino Acid (protein) | Mutation Type | Consequence | % Mutant Tags | Distinct Mutant Reads | Normal Distinct Phred Coverage |
|---|---|---|---|---|---|---|---|---|---|---|
| CGLI 02 PT | ZNF513 | zinc finger protein 513 | CCDS1761.1 | chr2_27601720-27601720_G_A | 138P>L | Substitution | Nonsynonymous coding | 49% | 88 | 149 |
| CGLI 02 PT | PLA2G4D | phospholipase A2, group IVD (cytosolic) | CCDS32203.1 | chr15_42378475-42378475_A_C | 108L>R | Substitution | Nonsynonymous coding | 42% | 34 | 82 |
| CGLI 02 PT | PIGM | phosphatidylinositol glycan anchor biosynthesis, class M | CCDS1192.1 | chr1_160000548-160000548_T_A | 328N>Y | Substitution | Nonsynonymous coding | 40% | 129 | 211 |
| CGLI 02 PT | PIGM | phosphatidylinositol glycan anchor biosynthesis, class M | CCDS1192.1 | chr1_160000549-160000549_A_C | 327F>L | Substitution | Nonsynonymous coding | 40% | 130 | 213 |
| CGLI 02 PT | LRP1 | Prolow-density lipoprotein receptor-related protein 1 precursor (LRP) (Alpha-2-macroglobulin receptor) (A2MR) (Apolipoprotein E receptor; APOER) (CD91 antigen) (Contains: Low-density lipoprotein receptor- related protein 1 85 kDa subunit (LRP-85) | CCDS8932.1 | chr12_57598461-57598461_T_G | 3708V>G | Substitution | Nonsynonymous coding | 31% | 73 | 263 |
| CGLI 02 PT | LRP1 | Prolow-density lipoprotein receptor-related protein 1 precursor (LRP) (Alpha-2-macroglobulin receptor) (A2MR) (Apolipoprotein E receptor; APOER) (CD91 antigen) (Contains: Low-density lipoprotein receptor- related protein 1 85 kDa subunit (LRP-85) | CCDS8932.1 | chr12_57598449-57598449_A_C | 3704K>T | Substitution | Nonsynonymous coding | 29% | 74 | 298 |
| CGLI 03 PT | H3F3A | Histone H3.3;H3F3A;ortholog | CCDS1550.1 | chr1_226252135-226252135_A_T | K28M | Substitution | nonsynonymous SNV | 44% | 26 | 71 |
| CGLI 03 PT | MYT1 | Myelin transcription factor 1;MYT1;ortholog | CCDS13558.1 | chr20_62844855-62844855__C | T529fs | Insertion | frameshift insertion | 44% | 39 | 71 |
| CGLI 03 PT | EP300 | Histone acetyltransferase p300;EP300;ortholog | CCDS14010.1 | chr22_41572437-41572437_G_T | V1656L | Substitution | nonsynonymous SNV | 38% | 32 | 71 |
| CGLI 03 PT | LILRB5 | Leukocyte immunoglobulin-like receptor subfamily B member 5;LILRB5;ortholog | CCDS12864.1 | chr19_54760520-54760520_C_T | R728W | Substitution | nonsynonymous SNV | 38% | 53 | 71 |
| CGLI 03 PT | XPOT | Exportin-T;XPOT;ortholog | CCDS31852.1 | chr12_64819637-64819637_A_G | K539E | Substitution | nonsynonymous SNV | 34% | 24 | 71 |
| CGLI 03 PT | PIK3R1 | Phosphatidylinositol 3-kinase regulatory subunit alpha;PIK3R1;ortholog | CCDS56374.1 | chr5_67591097-67591097_A_G | N564D | Substitution | nonsynonymous SNV | 31% | 36 | 71 |
| CGLI 03 PT | FLG | Filaggrin;FLG;ortholog | CCDS30860.1 | chr1_152280405-152280405_A_C | H2318Q | Substitution | nonsynonymous SNV | 29% | 75 | 71 |
| CGLI 03 PT | ASCL3 | Achaete-scute homolog 3;ASCL3;ortholog | CCDS7795.1 | chr11_8959618-8959618_G_T | L31M | Substitution | nonsynonymous SNV | 28% | 25 | 71 |
| CGLI 03 PT | PPM1D | Protein phosphatase 1D;PPM1D;ortholog | CCDS11625.1 | chr17_58740624-58740624__A | Q510fs | Insertion | frameshift insertion | 27% | 43 | 71 |
| CGLI 03 PT | SOX6 | Transcription factor SOX-6;SOX6;ortholog | CCDS53604.1 | chr11_16340062-16340062__C | G125fs | Insertion | frameshift insertion | 25% | 38 | 71 |
| CGLI 03 PT | ATAD3B | ATPase family AAA domain-containing protein 3B;ATAD3B;ortholog | CCDS30.1 | chr1_1421990-1421990_C_T | R366W | Substitution | nonsynonymous SNV | 17% | 12 | 71 |
| CGLI 06 PT | CLCA3P | chloride channel accessory 3 (pseudogene) | ENST00000224054 | chr1_87101784-87101784_G_A | 149R>Q | Substitution | Nonsynonymous coding | 36% | 33 | 96 |
| CGLI 06 PT | IGHM | immunoglobulin heavy constant mu | ENST00000390559 | chr14_106320761-106320761_G_A | 350R>C | Substitution | Nonsynonymous coding | 18% | 45 | 261 |
| CGLI 06 PT | TUBB | Tubulin beta chain (Tubulin beta-5 chain) | CCDS4687.1 | chr6_30690713-30690713_G_T | 62R>L | Substitution | Nonsynonymous coding | 18% | 22 | 56 |
| CGLI 06 PT | MLL3 | myeloid/lymphoid or mixed-lineage leukemia 3 | CCDS5931.1 | chr7_151945330-151945330_C_T | 730S>Y | Substitution | Nonsynonymous coding | 17% | 52 | 14 |
| CGLI 11 PT | ANKS3 | ankyrin repeat and sterile alpha motif domain containing 3 | CCDS10529.1 | chr16_4748050-4748050_C_T | 580E>K | Substitution | Nonsynonymous coding | 47% | 64 | 106 |
| CGLI 11 PT | COL11A2 | Collagen alpha-2(XI) chain precursor | CCDS43452.1 | chr6_33147579-33147579_G_A | 369R>W | Substitution | Nonsynonymous coding | 42% | 111 | 258 |
| CGLI 11 PT | FGD2 | FYVE, RhoGEF and PH domain containing 2 | CCDS4829.1 | chr6_36993607-36993607_A_C | 500K>Q | Substitution | Nonsynonymous coding | 39% | 126 | 242 |
| CGLI 11 PT | ESX1 | ESX homeobox 1 | CCDS14516.1 | chrX_103495171-103495171_G_C | 320P>R | Substitution | Nonsynonymous coding | 24% | 73 | 15 |
| CGLI 11 PT | PAMR1 | peptidase domain containing associated with muscle regeneration 1 | CCDS7898.1 | chr11_35457815-35457815_T_C | 407K>R | Substitution | Nonsynonymous coding | 21% | 32 | 150 |
| CGLI 11 PT | SPIRE1 | spire homolog 1 (Drosophila) | CCDS32790.1 | chr18_12535604-12535604_T_C | NA | Substitution | Splice site acceptor | 16% | 21 | 113 |
| CGLI 11 PT | USP18 | ubiquitin specific peptidase 18 | CCDS13752.1 | chr22_18655970-18655970_C_G | 315D>E | Substitution | Nonsynonymous coding | 16% | 4 | 38 |
| CGLI 11 PT | AMDHD1 | amidohydrolase domain containing 1 | CCDS9057.1 | chr12_96356196-96356196_G_A | 293V>I | Substitution | Nonsynonymous coding | 15% | 25 | 161 |
| CGLI 11 PT | C5 | complement component 5 | CCDS6826.1 | chr9_123760036-123760036_C_T | 859M>I | Substitution | Nonsynonymous coding | 11% | 8 | 54 |
| CGLI 12 PT | NCOR1 | nuclear receptor co-repressor 1 | CCDS11175.1 | chr17_16012211-16012211_G_A | 691R>C | Substitution | Nonsynonymous coding | 56% | 20 | 40 |
| CGLI 12 PT | ProSAPiP1 | Uncharacterized protein KIAA0552 | CCDS13049.1 | chr20_3145218-3145218_C_A | 635R>L | Substitution | Nonsynonymous coding | 50% | 277 | 326 |

Fig. 8 (continued)

| Sample | Gene | Description | Transcript | Position | AA Change | Type | Effect | Freq | Alt | Total |
|---|---|---|---|---|---|---|---|---|---|---|
| CGLI 12 PT | TTN | ttn | ENST00000375033 | chr2_179429822-179429822_G_A | 22994R>X | Substitution | Nonsense | 48% | 146 | 251 |
| CGLI 12 PT | HIST1H3C | histone cluster 1; H3c | CCDS4576.1 | chr6_26046721-26046721_A_T | 28K>M | Substitution | Nonsynonymous coding | 44% | 118 | 199 |
| CGLI 12 PT | SPTA1 | spectrin; alpha; erythrocytic 1 (elliptocytosis 2) | CCDS41423.1 | chr1_158644160-158644160_C_T | 437V>M | Substitution | Nonsynonymous coding | 44% | 148 | 225 |
| CGLI 12 PT | ASXL1 | additional sex combs like 1 (Drosophila) | CCDS13201.1 | chr20_31023569-31023570_TA_ | NA | Deletion | Frameshift | 42% | 270 | 432 |
| CGLI 12 PT | ANO8 | anoctamin 8 | CCDS32949.1 | chr19_17443766-17443766_C_T | 187V>M | Substitution | Nonsynonymous coding | 21% | 120 | 386 |
| CGLI 13 PT | TTC16 | tetratricopeptide repeat domain 16 | CCDS6875.1 | chr9_130486542-130486542_T_A | 339V>E | Substitution | Nonsynonymous coding | 48% | 331 | 209 |
| CGLI 13 PT | PCSK7 | proprotein convertase subtilisin/kexin type 7 | CCDS8362.1 | chr11_117076953-117076953_C_A | 706W>C | Substitution | Nonsynonymous coding | 20% | 64 | 194 |
| CGLI 15 PT | MARS | methionyl-tRNA synthetase | CCDS8942.1 | chr12_57905599-57905599_C_T | 496I>I | Substitution | Nonsynonymous coding | 13% | 43 | 196 |
| CGLI 20 PT | SORCS2 | sortilin-related VPS10 domain containing receptor 2 | NM_020777 | chr4_7731407-7731407_C_T | 1026P>S | Substitution | Nonsynonymous coding | 62% | 69 | 92 |
| CGLI 20 PT | RGS12 | regulator of G-protein signaling 12 | CCDS3366.1 | chr4_3424244-3424244_C_T | 994R>W | Substitution | Nonsynonymous coding | 52% | 79 | 143 |
| CGLI 20 PT | NLRP12 | NLR family, pyrin domain containing 12 | CCDS12884.1 | chr19_54314438-54314438_G_A | 159R>W | Substitution | Nonsynonymous coding | 51% | 285 | 388 |
| CGLI 20 PT | FGF3 | fibroblast growth factor 3 (murine mammary tumor virus integration site (v-int-2) oncogene homolog) | CCDS8195.1 | chr11_69625281-69625281_C_T | 171R>H | Substitution | Nonsynonymous coding | 49% | 190 | 287 |
| CGLI 20 PT | ITGB1BP3 | integrin beta 1 binding protein 3 | CCDS12115.1 | chr19_3936620-3936620_C_T | 25A>V | Substitution | Nonsynonymous coding | 49% | 98 | 144 |
| CGLI 20 PT | PCDH18 | protocadherin 18 | CCDS34064.1 | chr4_138449707-138449707_G_A | 889R>X | Substitution | Nonsense | 49% | 34 | 146 |
| CGLI 20 PT | FARS2 | phenylalanyl-tRNA synthetase 2; mitochondrial | CCDS4494.1 | chr6_5771526-5771526_C_T | 407T>M | Substitution | Nonsynonymous coding | 47% | 41 | 38 |
| CGLI 20 PT | CEP350 | centrosomal protein 350kDa | NM_014810 | chr1_179965725-179965725_C_T | 146H>Y | Substitution | Nonsynonymous coding | 46% | 48 | 80 |
| CGLI 20 PT | CXCR6 | chemokine (C-X-C motif) receptor 6 | CCDS2735.1 | chr3_45988586-45988586_G_A | 205L>I | Substitution | Nonsynonymous coding | 46% | 207 | 295 |
| CGLI 20 PT | IL16 | interleukin 16 (lymphocyte chemoattractant factor) | CCDS42069.1 | chr15_81592072-81592072_G_A | 802R>H | Substitution | Nonsynonymous coding | 45% | 286 | 465 |
| CGLI 20 PT | PRG2 | proteoglycan 2; bone marrow (natural killer cell activator, eosinophil granule major basic protein) | CCDS7955.1 | chr11_57156487-57156487_G_A | 121A>V | Substitution | Nonsynonymous coding | 44% | 201 | 313 |
| CGLI 20 PT | SIGLEC1 | sialic acid binding Ig-like lectin 1; sialoadhesin | CCDS13060.1 | chr20_3670684-3670684_C_T | 1607D>N | Substitution | Nonsynonymous coding | 44% | 195 | 317 |
| CGLI 20 PT | CHD7 | chromodomain-helicase-DNA-binding protein 7 | NM_017780 | chr8_61729063-61729063_A_T | NA | Substitution | Splice site donor | 42% | 16 | 27 |
| CGLI 20 PT | ACTL9 | actin-like 9 | CCDS12207.1 | chr19_8806220-8806220_G_A | 278R>W | Substitution | Nonsynonymous coding | 40% | 245 | 359 |
| CGLI 20 PT | AIFM1 | apoptosis-inducing factor; mitochondrion-associated; 1 | CCDS14618.1 | chrX_129264108-129264108_G_A | 536S>F | Substitution | Nonsynonymous coding | 37% | 32 | 153 |
| CGLI 20 PT | MKL1 | megakaryoblastic leukemia (translocation) 1 | CCDS14003.1 | chr22_40814691-40814691_C_G | 584C>S | Substitution | Nonsynonymous coding | 36% | 26 | 65 |
| CGLI 20 PT | PGGT1B | protein geranylgeranyltransferase type I; beta subunit | CCDS4116.1 | chr5_114548241-114548241_A_T | 331L>Q | Substitution | Nonsynonymous coding | 36% | 10 | 36 |
| CGLI 20 PT | KCNK10 | potassium channel; subfamily K; member 10 | CCDS9881.1 | chr14_88652379-88652379_G_A | 378R>C | Substitution | Nonsynonymous coding | 35% | 111 | 230 |
| CGLI 20 PT | LRP1 | P=low-density lipoprotein receptor-related protein 1 precursor (LRP) (Alpha-2-macroglobulin receptor) (A2MR) (Apolipoprotein E receptor) (APOER) (CD91 antigen) [Contains: Low-density lipoprotein receptor-related protein 1 85 kDa subunit (LRP-85)] | CCDS8932.1 | chr12_57556270-57556270_G_T | 791E>D | Substitution | Nonsynonymous coding | 34% | 36 | 66 |
| CGLI 20 PT | AHNAK2 | protein AHNAK2 | NM_138420 | chr14_105418346-105418346_T_C | 2148T>A | Substitution | Nonsynonymous coding | 27% | 4 | 11 |
| CGLI 20 PT | TENC1 | tensin like C1 domain containing phosphatase (tensin 2) | CCDS8842.1 | chr12_53453836-53453836_G_A | 814R>H | Substitution | Nonsynonymous coding | 26% | 60 | 204 |
| CGLI 20 PT | C14orf80 | hypothetical protein LOC283643 isoform 1 | NM_001134675 | chr14_105963713-105963713_G_A | 235R>H | Substitution | Nonsynonymous coding | 24% | 21 | 87 |
| CGLI 20 PT | KCTD10 | potassium channel tetramerisation domain containing 10 | CCDS9128.1 | chr12_109893952-109893952_C_T | 232V>I | Substitution | Nonsynonymous coding | 23% | 50 | 231 |
| CGLI 20 PT | ANKRD23 | ankyrin repeat domain 23 | CCDS2027.1 | chr2_97506603-97506603_A_G | 116L>P | Substitution | Nonsynonymous coding | 20% | 39 | 205 |

Fig. 8 (continued)

| Sample | Gene | Description | Accession | Location | AA Change | Type | Effect | Freq | Var Reads | Total Reads |
|---|---|---|---|---|---|---|---|---|---|---|
| CGLI 20 PT | AL137145.13 | Putative uncharacterized protein DKFZp667F0711 (Fragment) | ENST00000391437 | chr10_8392467-8392467_G_A | 63R>H | Substitution | Nonsynonymous coding | 19% | 66 | 348 |
| CGLI 20 PT | GPAM | glycerol-3-phosphate acyltransferase, mitochondrial | CCDS7570.1 | chr10_113937800-113937800_G_A | 81P>S | Substitution | Nonsynonymous coding | 19% | 5 | 42 |
| CGLI 20 PT | ARID1A | AT rich interactive domain 1A (SWI-like) | CCDS285.1 | chr1_27106873-27106873_G_T | 2182V>L | Substitution | Nonsynonymous coding | 18% | 56 | 297 |
| CGLI 20 PT | DSCAML1 | Down syndrome cell adhesion molecule like 1 | CCDS8384.1 | chr11_117403208-117403208_C_T | 241G>R | Substitution | Nonsynonymous coding | 18% | 33 | 136 |
| CGLI 20 PT | FAM175B | family with sequence similarity 175, member B | CCDS31308.2 | chr10_126507952-126507952_G_A | NA | Substitution | Splice site acceptor | 18% | 6 | 36 |
| CGLI 20 PT | KIAA1462 | KIAA1462 | CCDS41500.1 | chr10_30315473-30315473_C_T | 1202E>K | Substitution | Nonsynonymous coding | 18% | 43 | 199 |
| CGLI 20 PT | ITGAD | integrin, alpha D | CCDS32438.1 | chr16_31424208-31424208_C_T | 568A>V | Substitution | Nonsynonymous coding | 17% | 53 | 287 |
| CGLI 20 PT | OR52K1 | olfactory receptor, family 52, subfamily K, member 1 | CCDS31352.1 | chr11_4510637-4510637_G_T | 236R>L | Substitution | Nonsynonymous coding | 15% | 109 | 460 |
| CGLI 20 PT | BCL2L12 | BCL2-like 12 (proline rich) | CCDS12776.1 | chr19_50169232-50169232_G_A | 51R>K | Substitution | Nonsynonymous coding | 14% | 18 | 151 |
| CGLI 20 PT | SEPT1 | septin 1 | CCDS10678.1 | chr16_30389771-30389771_T_C | 363Q>R | Substitution | Nonsynonymous coding | 14% | 50 | 260 |
| CGLI 20 PT | LRRC15 | leucine rich repeat containing 15 | CCDS3306.1 | chr3_194080233-194080233_C_ | NA | Deletion | Frameshift | 12% | 74 | 371 |
| CGLI 22 PT | CC2D2A | coiled-coil and C2 domain-containing protein 2A isoform a | NM_001080522 | chr4_15539694-15539694_G_A | 646W>X | Substitution | Nonsense | 54% | 39 | 129 |
| CGLI 22 PT | C13orf23 | protein phosphatase 3, catalytic subunit, alpha isozyme | CCDS34037.1 | chr4_102015021-102015021__ACAGG | NA | Insertion | Frameshift | 35% | 32 | 126 |
| CGLI 22 PT | MTUS2 | microtubule-associated tumor suppressor | NM_001033602 | chr13_29608197-29608197_C_T | 604A>V | Substitution | Nonsynonymous coding | 25% | 17 | 355 |
| CGLI 25 PT | CDH5 | cadherin 5, type 2 (vascular endothelium) | CCDS10804.1 | chr16_68426280-68426280_G_A | 404S>N | Substitution | Nonsynonymous coding | 50% | 92 | 174 |
| CGLI 25 PT | RALYL | RNA-binding Raly-like protein isoform 1 | NM_001100391 | chr8_85774584-85774584_T_C | 169L>P | Substitution | Nonsynonymous coding | 50% | 61 | 144 |
| CGLI 25 PT | POLR2E | polymerase (RNA) II (DNA directed) polypeptide E, 25kDa | CCDS12056.1 | chr19_1090975-1090975_T_C | 121M>V | Substitution | Nonsynonymous coding | 48% | 88 | 181 |
| CGLI 25 PT | RP1 | retinitis pigmentosa 1 (autosomal dominant) | CCDS6160.1 | chr8_55541396-55541396_C_T | 1652R>C | Substitution | Nonsynonymous coding | 47% | 111 | 243 |
| CGLI 25 PT | ADRA1B | adrenergic, alpha-1B-, receptor | CCDS4347.1 | chr5_159344705-159344705_C_A | 265L>I | Substitution | Nonsynonymous coding | 45% | 211 | 434 |
| CGLI 25 PT | THUMPD2 | THUMP domain containing 2 | CCDS1805.1 | chr2_39964086-39964086_T_C | 404D>G | Substitution | Nonsynonymous coding | 43% | 72 | 186 |
| CGLI 25 PT | SIPA1L1 | signal-induced proliferation-associated 1 like 1 | CCDS9807.1 | chr14_72191469-72191469_A_G | 1532T>A | Substitution | Nonsynonymous coding | 40% | 45 | 107 |
| CGLI 25 PT | RNMT | RNA (guanine-7-) methyltransferase | CCDS11867.1 | chr18_13742491-13742491_C_T | 327R>C | Substitution | Nonsynonymous coding | 38% | 22 | 58 |
| CGLI 25 PT | ESX1 | ESX homeobox 1 | CCDS14516.1 | chrX_103495190-103495190_T_G | 314I>P | Substitution | Nonsynonymous coding | 22% | 20 | 24 |
| CGLI 25 PT | PKD1L2 | polycystic kidney disease 1-like 2 | CCDS42202.1 | chr16_81224278-81224278_C_A | 555G>X | Substitution | Nonsense | 18% | 14 | 64 |
| CGLI 25 PT | MYOM2 | myomesin (M-protein) 2, 165kDa | CCDS5957.1 | chr8_2017605-2017605_T_C | 261L>P | Substitution | Nonsynonymous coding | 16% | 39 | 223 |
| CGLI 25 PT | TMEM117 | transmembrane protein 117 | CCDS8745.1 | chr12_44238546-44238546_C_T | 31A>V | Substitution | Nonsynonymous coding | 15% | 26 | 167 |
| CGLI 25 PT | TMEM26 | transmembrane protein 26 | ENST00000399293 | chr10_63175849-63175849_T_G | 213H>P | Substitution | Nonsynonymous coding | 12% | 9 | 73 |
| CGLI 25 PT | UNC13C | protein unc-13 homolog C | NM_001080534 | chr15_54786899-54786899_C_T | 1676P>L | Substitution | Nonsynonymous coding | 11% | 14 | 122 |
| CGLI 29 PT | CCT3 | T-complex protein 1 subunit gamma;CCT3;ortholog | CCDS30888.1 | chr1_156279037-156279037_C_A | D493Y | Substitution | nonsynonymous SNV | 63% | 34 | 71 |
| CGLI 29 PT | TP53 | Cellular tumor antigen p53;TP53;ortholog | CCDS11118.1 | chr17_7577539-7577539_G_A | R248W | Substitution | nonsynonymous SNV | 62% | 33 | 77 |
| CGLI 29 PT | CCNC | Cyclin-C;CCNC;ortholog | CCDS47461.1 | chr6_99998120-99998120_T_G | Q83H | Substitution | nonsynonymous SNV | 45% | 30 | 77 |
| CGLI 29 PT | SLFN5 | Schlafen family member 5;SLFN5;ortholog | CCDS32619.1 | chr17_33586308-33586308_T_G | F200C | Substitution | nonsynonymous SNV | 39% | 55 | 71 |
| CGLI 29 PT | KIR3DL3 | Killer cell immunoglobulin-like receptor 3DL3;KIR3DL3;ortholog | CCDS12903.1 | chr19_55247543-55247543_C_A | P405T | Substitution | nonsynonymous SNV | 31% | 75 | 71 |
| CGLI 29 PT | NLRP8 | NACHT, LRR and PYD domains-containing protein 8;NLRP8;ortholog | CCDS12937.1 | chr19_56466565-56466565_A_G | S381G | Substitution | nonsynonymous SNV | 29% | 40 | 77 |
| CGLI 29 PT | ACSL6 | Long-chain-fatty-acid--CoA ligase 6;ACSL6;ortholog | CCDS56381.1 | chr5_131326851-131326851_C_T | G89R | Substitution | nonsynonymous SNV | 29% | 20 | 71 |
| CGLI 29 PT | ACOXL | Acyl-coenzyme A oxidase-like protein;ACOXL;ortholog | CCDS46369.1 | chr2_111561707-111561707_G_A | A101T | Substitution | nonsynonymous SNV | 26% | 47 | 71 |
| CGLI 29 PT | CTSZ | Cathepsin Z;CTSZ;ortholog | CCDS13474.1 | chr20_57576589-57576589_C_T | V140M | Substitution | nonsynonymous SNV | 25% | 44 | 77 |
| CGLI 29 PT | FOXP2 | Forkhead box protein P2;FOXP2;ortholog | CCDS55154.1 | chr7_114268687-114268687_C_A | Q117H | Substitution | nonsynonymous SNV | 21% | 44 | 71 |
| CGLI 29 PT | COL18A1 | Collagen alpha-1(XVIII) chain;COL18A1;ortholog | NULL | chr21_46916413-46916413_G_T | splicing | Substitution | NULL | 20% | 12 | 71 |

Fig. 8 (continued)

| Sample | Gene | Description | CCDS | Location | Change | Type | Mutation | VAF | Reads | Coverage |
|---|---|---|---|---|---|---|---|---|---|---|
| CGLI 29 PT | PRX | Periaxin;PRX;ortholog | CCDS33028.1 | chr19_40900839-40900839_G_C | D1140E | Substitution | nonsynonymous SNV | 20% | 27 | 71 |
| CGLI 29 PT | GPR52 | Probable G-protein coupled receptor 52;GPR52;ortholog | CCDS30941.1 | chr1_174417815-174417815_T_C | I189T | Substitution | nonsynonymous SNV | 19% | 33 | 71 |
| CGLI 29 PT | DVL3 | Segment polarity protein dishevelled homolog DVL-3;DVL3;ortholog | CCDS3253.1 | chr3_183865844-183865844_C_T | L497F | Substitution | nonsynonymous SNV | 16% | 25 | 71 |
| CGLI 29 PT | CCDC28B | Coiled-coil domain-containing protein 28B;CCDC28B;ortholog | CCDS254.2 | chr1_32669496-32669496_T_C | C61R | Substitution | nonsynonymous SNV | 16% | 12 | 71 |
| CGLI 29 PT | OR2T1 | Olfactory receptor 2T1;OR2T1;ortholog | CCDS31115.1 | chr1_248570311-248570311_T_C | I339T | Substitution | nonsynonymous SNV | 16% | 14 | 71 |
| CGLI 29 PT | FAT4 | Protocadherin Fat 4;FAT4;ortholog | CCDS3732.3 | chr4_126328129-126328129_G_A | R1604Q | Substitution | nonsynonymous SNV | 16% | 17 | 71 |
| CGLI 29 PT | IL4 | Interleukin-4;IL4;ortholog | CCDS4159.1 | chr5_132015545-132015545_A_T | K92I | Substitution | nonsynonymous SNV | 15% | 11 | 71 |
| CGLI 29 PT | FAT4 | Protocadherin Fat 4;FAT4;ortholog | CCDS3732.3 | chr4_126411775-126411775_C_A | R1601Q | Substitution | nonsynonymous SNV | 15% | 19 | 71 |
| CGLI 29 PT | LAMA2 | Laminin subunit alpha-2;LAMA2;ortholog | CCDS5136.1 | chr6_129511454-129511454_A_ | S524fs | Deletion | frameshift deletion | 15% | 16 | 71 |
| CGLI 29 PT | SMURF1 | E3 ubiquitin-protein ligase SMURF1;SMURF1;ortholog | CCDS34689.1 | chr7_98649837-98649837_C_G | E238Q | Substitution | nonsynonymous SNV | 15% | 26 | 77 |
| CGLI 29 PT | ZNF287 | Zinc finger protein 287;ZNF287;ortholog | CCDS11179.2 | chr17_16470784-16470764_T_ | I88fs | Deletion | frameshift deletion | 15% | 15 | 71 |
| CGLI 29 PT | FGA | Fibrinogen alpha chain;FGA;ortholog | CCDS3787.1 | chr4_155507259-155507259_T_C | E441G | Substitution | nonsynonymous SNV | 15% | 24 | 71 |
| CGLI 29 PT | HCK | Tyrosine-protein kinase HCK;HCK;ortholog | CCDS54455.1 | chr20_30672276-30672276_A_G | E235G | Substitution | nonsynonymous SNV | 14% | 10 | 71 |
| CGLI 29 PT | KIFC1 | Kinesin-like protein KIFC1;KIFC1;ortholog | CCDS34430.1 | chr6_33373327-33373327_T_G | C465W | Substitution | nonsynonymous SNV | 14% | 28 | 71 |
| CGLI 29 PT | TXK | Tyrosine-protein kinase TXK;TXK;ortholog | CCDS3480.1 | chr4_48114360-48114360_T_C | Y115C | Substitution | nonsynonymous SNV | 14% | 15 | 71 |
| CGLI 29 PT | PLXNB1 | Plexin-B1;PLXNB1;ortholog | CCDS2765.1 | chr3_48445929-48445929_A_C | I2124M | Substitution | nonsynonymous SNV | 14% | 10 | 71 |
| CGLI 29 PT | KIFC1 | Kinesin-like protein KIFC1;KIFC1;ortholog | CCDS34430.1 | chr6_33373329-33373329_A_T | C465W | Substitution | nonsynonymous SNV | 14% | 29 | 71 |
| CGLI 29 PT | KIFC1 | Kinesin-like protein KIFC1;KIFC1;ortholog | CCDS34430.1 | chr6_33373328-33373328_G_T | C465W | Substitution | stopgain | 13% | 26 | 71 |
| CGLI 29 PT | CYP2B6 | Cytochrome P450 2B6;CYP2B6;ortholog | CCDS12570.1 | chr19_41518239-41518239_C_A | P334Q | Substitution | nonsynonymous SNV | 13% | 10 | 71 |
| CGLI 29 PT | IARS | Isoleucine--tRNA ligase, cytoplasmic;IARS;ortholog | CCDS6694.1 | chr9_95005508-95005508_A_C | L997R | Substitution | nonsynonymous SNV | 13% | 22 | 77 |
| CGLI 29 PT | CASKIN1 | Caskin-1;CASKIN1;ortholog | CCDS42103.1 | chr16_2231860-2231860_T_A | Y567F | Substitution | nonsynonymous SNV | 13% | 18 | 71 |
| CGLI 29 PT | GPR162 | Probable G-protein coupled receptor 162;GPR162;ortholog | CCDS44819.1 | chr12_6936028-6936028_C_A | L192M | Substitution | nonsynonymous SNV | 12% | 34 | 77 |
| CGLI 29 PT | TRAF4 | TNF receptor-associated factor 4;TRAF4;ortholog | CCDS11243.1 | chr17_27075574-27075574_C_A | Q224K | Substitution | nonsynonymous SNV | 12% | 20 | 71 |
| CGLI 29 PT | AKAP13 | A-kinase anchor protein 13;AKAP13;ortholog | CCDS32319.1 | chr15_86265463-86265463_G_C | K2127N | Substitution | nonsynonymous SNV | 12% | 21 | 77 |
| CGLI 29 PT | OR5M9 | Olfactory receptor 5M9;OR5M9;ortholog | CCDS31531.1 | chr11_56230270-56230270_A_G | I203T | Substitution | nonsynonymous SNV | 11% | 15 | 77 |
| CGLI 29 PT | PLB1 | Phospholipase B1, membrane-associated;PLB1;ortholog | CCDS33155.1 | chr2_28789670-28789670_G_A | G430R | Substitution | nonsynonymous SNV | 10% | 35 | 71 |
| CGLI 29 PT | FGD6 | FYVE, RhoGEF and PH domain-containing protein 6;FGD6;ortholog | CCDS31976.1 | chr12_95603268-95603268_G_T | L598I | Substitution | nonsynonymous SNV | 10% | 20 | 77 |
| CGLI 29 PT | NPM3 | Nucleoplasmin-3;NPM3;ortholog | CCDS7519.1 | chr10_103542299-103542299_C_T | R87Q | Substitution | nonsynonymous SNV | 10% | 24 | 71 |
| CGLI 29 PT | KCNV1 | Potassium voltage-gated channel subfamily V member 1;KCNV1;ortholog | CCDS6314.1 | chr8_110980417-110980417_A_C | L488W | Substitution | nonsynonymous SNV | 10% | 11 | 71 |
| CGLI 29 PT | LRP2 | Low-density lipoprotein receptor-related protein 2;LRP2;ortholog | CCDS2332.1 | chr2_170030642-170030642_A_G | C3601R | Substitution | nonsynonymous SNV | 10% | 10 | 71 |
| CGLI 29 PT | AP4B1 | AP-4 complex subunit beta-1;AP4B1;ortholog | CCDS865.1 | chr1_114439060-114439060_C_T | G444S | Substitution | nonsynonymous SNV | 9% | 10 | 71 |
| CGLI 29 PT | FOXM1 | Forkhead box protein M1;FOXM1;ortholog | CCDS8517.1 | chr12_2968522-2968522_C_T | R510Q | Substitution | nonsynonymous SNV | 9% | 22 | 71 |
| CGLI 29 PT | AGRN | Agrin;AGRN;ortholog | CCDS30551.1 | chr1_985049-985049_A_ | T1540fs | Deletion | frameshift deletion | 8% | 13 | 77 |
| CGLI 29 PT | SDC1 | Syndecan-1;SDC1;ortholog | CCDS1697.1 | chr2_20402672-20402672_C_G | G263A | Substitution | nonsynonymous SNV | 8% | 23 | 71 |
| CGLI 29 PT | SYBU | Syntabulin;SYBU;ortholog | CCDS55271.1 | chr8_110587728-110587728_C_A | V348F | Substitution | nonsynonymous SNV | 8% | 20 | 71 |
| CGLI 29 PT | SLC12A9 | Solute carrier family 12 member 9;SLC12A9;ortholog | CCDS59069.1 | chr7_100469055-100469055_G_T | G373V | Substitution | nonsynonymous SNV | 8% | 13 | 71 |
| CGLI 29 PT | CALR | Calreticulin;CALR;ortholog | CCDS12288.1 | chr19_13051217-13051217_A_G | D218G | Substitution | nonsynonymous SNV | 8% | 12 | 71 |
| CGLI 29 PT | SLC10A4 | Sodium/bile acid cotransporter 4;SLC10A4;ortholog | CCDS3482.1 | chr4_48487121-48487121_C_G | R255G | Substitution | nonsynonymous SNV | 7% | 12 | 71 |
| CGLI 29 PT | CDC14B | Dual specificity protein phosphatase CDC14B;CDC14B;ortholog | CCDS43853.1 | chr9_99285647-99285647_G_T | Q344K | Substitution | nonsynonymous SNV | 7% | 12 | 77 |

Fig. 8 (continued)

| Sample | Gene | Description | CCDS | Location | Change | Type | Effect | % | Reads | Total |
|---|---|---|---|---|---|---|---|---|---|---|
| CGLI 29 PT | DDX11 | Probable ATP-dependent RNA helicase DDX11;DDX11;ortholog | CCDS8721.1 | chr12_31255384-31255384_G_C | Q715H | Substitution | nonsynonymous SNV | 7% | 14 | 71 |
| CGLI 29 PT | CCDC8 | Coiled-coil domain-containing protein 8;CCDC8;ortholog | CCDS12685.1 | chr19_48915212-48915212_C_A | G268C | Substitution | nonsynonymous SNV | 7% | 26 | 71 |
| CGLI 29 PT | DDX11 | Probable ATP-dependent RNA helicase DDX11;DDX11;ortholog | CCDS8721.1 | chr12_31255383-31255383_A_C | Q715P | Substitution | nonsynonymous SNV | 6% | 13 | 71 |
| CGLI 36 CSF | TP53 | Cellular tumor antigen p53;TP53;ortholog | CCDS11118.1 | chr17_7577539-7577539_G_A | R248W | Substitution | nonsynonymous SNV | 9% | 6 | 77 |
| CGLI 36 PT | TP53 | Cellular tumor antigen p53;TP53;ortholog | CCDS11118.1 | chr17_7577539-7577539_G_A | R248W | Substitution | nonsynonymous SNV | 66% | 17 | 77 |
| CGLI 36 PT | TP53 | tumor protein p53 | CCDS11118.1 | chr17_7577539-7577539_G_A | 248R>W | Substitution | Nonsynonymous coding | 65% | 32 | 84 |
| CGLI 36 PT | MYT1 | myelin transcription factor 1 | CCDS13558.1 | chr20_62854466-62854466_G_T | 800C>F | Substitution | Nonsynonymous coding | 45% | 77 | 115 |
| CGLI 36 PT | CYP4A11 | cytochrome P450, family 4, subfamily A, polypeptide 11 | CCDS543.1 | chr1_47398493-47398493_C_T | 435R>H | Substitution | Nonsynonymous coding | 42% | 95 | 193 |
| CGLI 36 PT | PRKCA | protein kinase C, alpha | CCDS11664.1 | chr17_64784981-64784981_C_T | 580R>W | Substitution | Nonsynonymous coding | 42% | 109 | 196 |
| CGLI 36 PT | KCNH7 | potassium voltage-gated channel, subfamily H (eag-related), member 7 | CCDS2219.1 | chr2_163256863-163256863_C_T | 748G>E | Substitution | Nonsynonymous coding | 40% | 72 | 165 |
| CGLI 36 PT | WNT4 | wingless-type MMTV integration site family, member 4 | CCDS223.1 | chr1_22446991-22446991_C_T | 203R>Q | Substitution | Nonsynonymous coding | 39% | 99 | 151 |
| CGLI 36 PT | COL2A1 | collagen, type II, alpha 1 | CCDS41778.1 | chr12_48376911-48376911_C_T | 687G>S | Substitution | Nonsynonymous coding | 38% | 65 | 127 |
| CGLI 36 PT | VAX1 | ventral anterior homeobox 1 | CCDS7597.1 | chr10_118991757-118991757_C_T | 17SR>H | Substitution | Nonsynonymous coding | 36% | 112 | 239 |
| CGLI 36 PT | KCNH7 | Potassium voltage-gated channel subfamily H member 7;KCNH7;ortholog | CCDS2219.1 | chr2_163256863-163256863_C_T | G748E | Substitution | nonsynonymous SNV | 34% | 26 | 77 |
| CGLI 36 PT | MYT1 | Myelin transcription factor 1;MYT1;ortholog | CCDS13558.1 | chr20_62854466-62854466_G_T | C800F | Substitution | nonsynonymous SNV | 34% | 38 | 77 |
| CGLI 36 PT | MYOM1 | myomesin-1 isoform a | NM_003803 | chr18_3215068-3215068_C_T | 52A>T | Substitution | Nonsynonymous coding | 32% | 31 | 80 |
| CGLI 36 PT | OR2A14 | Olfactory receptor 2A14;OR2A14;ortholog | CCDS43672.1 | chr7_143826872-143826872_G_A | A223T | Substitution | nonsynonymous SNV | 31% | 11 | 77 |
| CGLI 36 PT | WNT4 | Protein Wnt-4;WNT4;ortholog | CCDS223.1 | chr1_22446991-22446991_C_T | R203Q | Substitution | nonsynonymous SNV | 30% | 26 | 77 |
| CGLI 36 PT | PRKCA | Protein kinase C alpha type;PRKCA;ortholog | CCDS11664.1 | chr17_64784981-64784981_C_T | R580W | Substitution | nonsynonymous SNV | 30% | 13 | 77 |
| CGLI 36 PT | COL2A1 | Collagen alpha-1(II) chain;COL2A1;ortholog | CCDS8759.1 | chr12_48376911-48376911_C_T | G616S | Substitution | nonsynonymous SNV | 28% | 22 | 77 |
| CGLI 36 PT | CDK17 | cyclin-dependent kinase 17 | CCDS9081.1 | chr12_96717791-96717791_G_A | 73P>L | Substitution | Nonsynonymous coding | 27% | 38 | 100 |
| CGLI 36 PT | CDK17 | Cyclin-dependent kinase 17;CDK17;ortholog | CCDS53819.1 | chr12_96717791-96717791_G_A | P73L | Substitution | nonsynonymous SNV | 21% | 16 | 77 |
| CGLI 36 PT | COL3A1 | collagen, type III, alpha 1 | CCDS2297.1 | chr2_189850389-189850389_A_ | NA | Deletion | Splice site acceptor | 15% | 4 | 20 |
| CGLI 39 PT | PDLIM4 | PDZ and LIM domain 4 | CCDS4152.1 | chr5_131607916-131607916_T_A | 296L>Q | Substitution | Nonsynonymous coding | 91% | 208 | 349 |
| CGLI 39 PT | NF2 | neurofibromin 2 (merlin) | CCDS13861.1 | chr22_30051658-30051658_C_T | 188R>X | Substitution | Nonsense | 80% | 8 | 34 |
| CGLI 39 PT | CKAP2 | cytoskeleton associated protein 2 | CCDS41893.1 | chr13_53035922-53035922_G_A | 322V>I | Substitution | Nonsynonymous coding | 43% | 51 | 298 |
| CGLI 39 PT | ALPK1 | alpha-kinase 1 | CCDS3697.1 | chr4_113362132-113362132_G_A | 1200V>I | Substitution | Nonsynonymous coding | 35% | 86 | 233 |
| CGLI 40 PT | CASR | calcium-sensing receptor | CCDS3010.1 | chr3_122003350-122003350_C_T | 850A>V | Substitution | Nonsynonymous coding | 45% | 59 | 167 |
| CGLI 40 PT | PKHD1L1 | polycystic kidney and hepatic disease 1 (autosomal recessive)-like 1 | CCDS47911.1 | chr8_110476637-110476637_T_ | NA | Deletion | Frameshift | 41% | 17 | 88 |
| CGLI 40 PT | TDRD6 | tudor domain containing 6 | CCDS34470.1 | chr6_46656656-46656656_G_A | 264R>H | Substitution | Nonsynonymous coding | 40% | 43 | 119 |
| CGLI 42 PT | COL6A1 | collagen, type VI, alpha 1 | CCDS13727.1 | chr21_47417353-47417353_G_A | 473G>R | Substitution | Nonsynonymous coding | 39% | 31 | 92 |
| CGLI 42 PT | GPR137C | G protein-coupled receptor 137C | CCDS45106.1 | chr14_53019944-53019944_A_G | 27S>G | Substitution | Nonsynonymous coding | 31% | 5 | 13 |
| CGLI 42 PT | GPR139 | G protein-coupled receptor 139 | CCDS32398.1 | chr16_20043965-20043965_A_ | NA | Deletion | Frameshift | 20% | 12 | 68 |
| CGLI 43 PT | NF2 | neurofibromin 2 (merlin) | CCDS13861.1 | chr22_30067824-30067824_C_T | 337Q>X | Substitution | Nonsense | 61% | 20 | 56 |
| CGLI 43 PT | C17orf51 | chromosome 17 open reading frame 51 | CCDS45626.1 | chr17_21454373-21454373_G_A | 105Q>X | Substitution | Nonsense | 23% | 7 | 41 |
| CGLI 43 PT | LARP7 | La ribonucleoprotein domain family, member 7 | CCDS3701.2 | chr4_113578483-113578483__A | NA | Insertion | Frameshift | 23% | 5 | 19 |
| CGLI 43 PT | ATP10B | ATPase, class V, type 10B | CCDS43394.1 | chr5_160049471-160049471_G_A | 581A>V | Substitution | Nonsynonymous coding | 22% | 14 | 64 |
| CGLI 43 PT | GUSBP12 | glucuronidase, beta pseudogene 12 | ENST00000 45142 | chr7_57271195-57271195_G_A | 25Q>X | Substitution | Nonsense | 21% | 8 | 38 |
| CGLI 43 PT | ANP32E | acidic (leucine-rich) nuclear phosphoprotein 32 family, member E | CCDS946.1 | chr1_150193045-150193045_C_T | 252G>E | Substitution | Nonsynonymous coding | 21% | 31 | 162 |

Fig. 8 (continued)

| | | | | | | | | | |
|---|---|---|---|---|---|---|---|---|---|
| CGLI 43 PT | SLC5A5 | solute carrier family 5 (sodium iodide symporter), member 5 | CCDS12368.1 | chr19_17983246-17983246_G_A | 40G>R | Substitution | Nonsynonymous coding | 19% | 13 | 91 |
| CGLI 43 PT | FSIP2 | fibrous sheath interacting protein 2 | ENST00000424728 | chr2_186670792-186670792_T_A | 556S>T | Substitution | Nonsynonymous coding | 17% | 4 | 65 |
| CGLI 43 PT | ZNF788 | zinc finger family member 788 | ENST00000339302 | chr19_12223616-12223616_T_A | 418Y>X | Substitution | Nonsense | 16% | 15 | 78 |
| CGLI 43 PT | CD2BP2 | CD2 (cytoplasmic tail) binding protein 2 | CCDS10675.1 | chr16_30364913-30364917_GAACT_ | NA | Deletion | Frameshift | 16% | 15 | 130 |
| CGLI 43 PT | AHRR | aryl-hydrocarbon receptor repressor | CCDS43297.1 | chr5_434824-434824_C_T | 679R>W | Substitution | Nonsynonymous coding | 14% | 10 | 97 |
| CGLI 43 PT | RNF112 | ring finger protein 112 | NM_007148 | chr17_19319013-19319014_CA_ | NA | Deletion | Splice site acceptor | 13% | 16 | 244 |
| CGLI 43 PT | EPHA7 | EPH receptor A7 | CCDS5031.1 | chr6_93979352-93979355_TGTT_ | NA | Deletion | Frameshift | 13% | 10 | 124 |
| CGLI 43 PT | HNRNPH2 | heterogeneous nuclear ribonucleoprotein H2 (H') | ENST00000392994 | chrX_100650478-100650478_T_G | 111F>L | Substitution | Nonsynonymous coding | 13% | 7 | 48 |
| CGLI 43 PT | FGF23 | fibroblast growth factor 23 | CCDS8628.1 | chr12_4488693-4488693_A_C | 19M>R | Substitution | Nonsynonymous coding | 13% | 5 | 84 |
| CGLI 43 PT | TTLL12 | tubulin tyrosine ligase-like family, member 12 | CCDS14047.1 | chr22_43575994-43575994_T_C | 197K>E | Substitution | Nonsynonymous coding | 12% | 25 | 393 |
| CGLI 43 PT | NRAP | nebulin-related anchoring protein | CCDS7579.1 | chr10_115409874-115409874_T_ | NA | Deletion | Frameshift | 12% | 8 | 78 |
| CGLI 43 PT | ANO2 | anoctamin 2 | CCDS44807.1 | chr12_5941690-5941690_G_A | 234P>L | Substitution | Nonsynonymous coding | 12% | 8 | 77 |
| CGLI 43 PT | TTLL12 | tubulin tyrosine ligase-like family, member 12 | CCDS14047.1 | chr22_43575990-43575993_ATCT_ | NA | Deletion | Frameshift | 11% | 22 | 383 |
| CGLI 43 PT | COL9A1 | collagen, type IX, alpha 1 | CCDS4871.1 | chr6_71003947-71003947_T_A | 207K>X | Substitution | Nonsense | 11% | 15 | 193 |
| CGLI 43 PT | C17orf53 | chromosome 17 open reading frame 53 | CCDS11877.1 | chr17_42230040-42230040_T_ | NA | Deletion | Frameshift | 11% | 7 | 87 |
| CGLI 43 PT | PRR14 | proline rich 14 | CCDS10687.1 | chr16_30664363-30664363_C_ | NA | Deletion | Frameshift | 11% | 7 | 143 |
| CGLI 43 PT | C2orf43 | chromosome 2 open reading frame 43 | ENST00000381090 | chr2_20865345-20865346_AG_ | NA | Deletion | Frameshift | 11% | 10 | 140 |
| CGLI 43 PT | HSPA14 | heat shock 70kDa protein 14 | CCDS7103.1 | chr10_14909870-14909870_G_ | NA | Deletion | Frameshift | 11% | 9 | 108 |
| CGLI 43 PT | LLGL2 | lethal giant larvae homolog 2 (Drosophila) | CCDS32733.1 | chr17_73567789-73567789_G_A | 740G>S | Substitution | Nonsynonymous coding | 11% | 4 | 63 |
| CGLI 44 PT | ALOX15 | arachidonate 15-lipoxygenase | CCDS11049.1 | chr17_4541604-4541604_C_T | 239V>M | Substitution | Nonsynonymous coding | 44% | 4 | 14 |
| CGLI 44 PT | ITGA11 | integrin, alpha 11 | CCDS45291.1 | chr15_68619063-68619063_G_A | 714R>X | Substitution | Nonsense | 16% | 16 | 124 |
| CGLI 44 PT | RASSF2 | Ras association (RalGDS/AF-6) domain family member 2 | CCDS13063.1 | chr20_4771131-4771131_C_T | 168R>H | Substitution | Nonsynonymous coding | 13% | 12 | 147 |
| CGLI 55 CSF | PTEN | Phosphatidylinositol 3,4,5-trisphosphate 3-phosphatase and dual-specificity protein phosphatase PTEN;PTEN;ortholog | CCDS31238.1 | chr10_89692904-89692904_C_T | R130X | Substitution | stopgain | 40% | 23 | 63 |
| CGLI 55 PT | CACNA1F | calcium channel, voltage-dependent, L type, alpha 1F subunit | CCDS35253.1 | chrX_49061742-49061742_C_T | 1939R>H | Substitution | Nonsynonymous coding | 100% | 93 | 219 |
| CGLI 55 PT | CILP | cartilage intermediate layer protein, nucleotide pyrophosphohydrolase | CCDS10203.1 | chr15_65494212-65494212_A_G | 395I>T | Substitution | Nonsynonymous coding | 100% | 22 | 33 |
| CGLI 55 PT | HLA-C | major histocompatibility complex, class I, C | CCDS34394.1 | chr6_31324536-31324536_T_C | 91Y>C | Substitution | Nonsynonymous coding | 100% | 40 | 135 |
| CGLI 55 PT | IRS4 | insulin receptor substrate 4 | CCDS14544.1 | chrX_107976940-107976940_G_C | 873H>D | Substitution | Nonsynonymous coding | 100% | 44 | 227 |
| CGLI 55 PT | MLC1 | megalencephalic leukoencephalopathy with subcortical cysts 1 | CCDS14083.1 | chr22_50502491-50502491_T_C | 344N>S | Substitution | Nonsynonymous coding | 100% | 21 | 21 |
| CGLI 55 PT | USH2A | Usher syndrome 2A (autosomal recessive, mild) | CCDS31025.1 | chr1_216258213-216258213_A_G | 1565I>T | Substitution | Nonsynonymous coding | 100% | 42 | 42 |
| CGLI 55 PT | ZNF275 | zinc finger protein 275 | ENST00000095634 | chrX_152610226-152610226_A_G | 64T>A | Substitution | Nonsynonymous coding | 100% | 7 | 154 |
| CGLI 55 PT | ZNF275 | zinc finger protein 275 | ENST00000095634 | chrX_152610229-152610229_C_G | 64T>S | Substitution | Nonsynonymous coding | 100% | 7 | 156 |
| CGLI 55 PT | ZNF275 | zinc finger protein 275 | ENST00000095634 | chrX_152610231-152610231_T_A | 65S>T | Substitution | Nonsynonymous coding | 100% | 4 | 154 |
| CGLI 55 PT | ZNF275 | zinc finger protein 275 | ENST00000095634 | chrX_152610232-152610232_C_A | 65S>Y | Substitution | Nonsynonymous coding | 100% | 4 | 152 |
| CGLI 55 PT | SFTPA1 | surfactant protein A1 | CCDS44445.1 | chr10_81373777-81373777_C_T | 219R>W | Substitution | Nonsynonymous coding | 99% | 94 | 97 |
| CGLI 55 PT | SLC45A2 | solute carrier family 45, member 2 | CCDS3901.1 | chr5_33951693-33951693_C_G | 374L>F | Substitution | Nonsynonymous coding | 98% | 54 | 115 |
| CGLI 55 PT | DARC | Duffy blood group, chemokine receptor | CCDS44252.1 | chr1_159175354-159175354_G_A | 44G>D | Substitution | Nonsynonymous coding | 97% | 512 | 516 |
| CGLI 55 PT | ANXA11 | annexin A11 | CCDS7364.1 | chr10_81926702-81926702_G_A | 230R>C | Substitution | Nonsynonymous coding | 97% | 29 | 77 |
| CGLI 55 PT | USP9X | Probable ubiquitin carboxyl-terminal hydrolase FAF-X;USP9X;ortholog | CCDS43930.1 | chrX_41022065-41022065_A_C | Q640H | Substitution | nonsynonymous SNV | 97% | 29 | 22 |
| CGLI 55 PT | C1orf86 | chromosome 1 open reading frame 86 | ENST00000378558 | chr1_2116901-2116901_G_C | 170P>R | Substitution | Nonsynonymous coding | 96% | 27 | 126 |
| CGLI 55 PT | TSC2 | tuberous sclerosis 2 | CCDS10458.1 | chr16_2105400-2105400_C_T | NA | Substitution | Splice site acceptor | 96% | 27 | 88 |

Fig. 8 (continued)

| Sample | Gene | Description | Accession | Location | Change | Type | Effect | % | Alt | Total |
|---|---|---|---|---|---|---|---|---|---|---|
| CGLI 55 PT | PTCHD1 | Patched domain containing protein 1;PTCHD1;ortholog | CCDS35215.2 | chrX_23410789-23410789_C_T | T385I | Substitution | nonsynonymous SNV | 96% | 25 | 83 |
| CGLI 55 PT | OTC | ornithine carbamoyltransferase | CCDS14247.1 | chrX_38226603-38226603_A_G | 48K>R | Substitution | Nonsynonymous coding | 96% | 25 | 100 |
| CGLI 55 PT | COMT | catechol-O-methyltransferase | CCDS13770.1 | chr22_19951271-19951271_G_A | 158V>M | Substitution | Nonsynonymous coding | 96% | 228 | 117 |
| CGLI 55 PT | ADCY9 | adenylate cyclase 9 | CCDS32382.1 | chr16_4033436-4033436_T_C | 772I>M | Substitution | Nonsynonymous coding | 95% | 90 | 103 |
| CGLI 55 PT | PTCHD1 | patched domain containing 1 | CCDS35215.2 | chrX_23410789-23410789_C_T | 385T>I | Substitution | Nonsynonymous coding | 94% | 29 | 269 |
| CGLI 55 PT | GUCY2F | guanylate cyclase 2F, retinal | CCDS14545.1 | chrX_108641850-108641850_T_C | 735S>G | Substitution | Nonsynonymous coding | 92% | 23 | 352 |
| CGLI 55 PT | TUBAL3 | tubulin, alpha-like 3 | CCDS7066.2 | chr10_5435790-5435790_G_A | 344S>L | Substitution | Nonsynonymous coding | 91% | 124 | 403 |
| CGLI 55 PT | ZC3H12B | zinc finger CCCH-type containing 12B | CCDS48131.1 | chrX_64717009-64717009__A | NA | Insertion | Splice site acceptor | 89% | 8 | 85 |
| CGLI 55 PT | USP9X | ubiquitin specific peptidase 9, X-linked | CCDS43930.1 | chrX_41022065-41022065_A_C | 640Q>H | Substitution | Nonsynonymous coding | 88% | 23 | 29 |
| CGLI 55 PT | HAVCR1 | hepatitis A virus cellular receptor 1 | CCDS43392.1 | chr5_156479569-156479569__GTT | NA | Insertion | In-frame insertion | 88% | 151 | 150 |
| CGLI 55 PT | KIAA0319L | KIAA0319-like | CCDS390.1 | chr1_35921709-35921709_T_G | 521T>P | Substitution | Nonsynonymous coding | 86% | 49 | 148 |
| CGLI 55 PT | SLC25A45 | solute carrier family 25, member 45 | ENST00000332723 | chr11_65143702-65143702_T_ | NA | Deletion | Frameshift | 88% | 56 | 144 |
| CGLI 55 PT | EXO5 | exonuclease 5 | CCDS453.1 | chr1_40980800-40980800_C_T | 195A>V | Substitution | Nonsynonymous coding | 87% | 41 | 176 |
| CGLI 55 PT | WDFY4 | WDFY family member 4 | CCDS44385.1 | chr10_50040723-50040723_G_A | 2211R>Q | Substitution | Nonsynonymous coding | 87% | 59 | 96 |
| CGLI 55 PT | WDR96 | WD repeat domain 96 | CCDS31281.1 | chr10_105953628-105953628_C_T | 480V>I | Substitution | Nonsynonymous coding | 87% | 52 | 111 |
| CGLI 55 PT | KHDC1 | KH homology domain containing 1 | ENST00000370380 | chr2_232317403-232317403_A_ | NA | Deletion | Frameshift | 86% | 44 | 195 |
| CGLI 55 PT | PCDH15 | protocadherin-related 15 | CCDS44404.1 | chr10_56287569-56287569_T_C | NA | Substitution | Splice site donor | 86% | 6 | 59 |
| CGLI 55 PT | CDH23 | cadherin-related 23 | NM_022124 | chr10_73537814-73537814_G_A | 1675V>I | Substitution | Nonsynonymous coding | 85% | 75 | 289 |
| CGLI 55 PT | SLC22A15 | solute carrier family 22, member 15 | CCDS44198.1 | chr1_116609219-116609219_C_A | 482P>T | Substitution | Nonsynonymous coding | 85% | 22 | 162 |
| CGLI 55 PT | MDP1 | magnesium-dependent phosphatase 1 | CCDS9620.1 | chr14_24683267-24683267_A_ | NA | Deletion | Frameshift | 84% | 54 | 262 |
| CGLI 55 PT | INPP5B | inositol polyphosphate-5-phosphatase, 75kDa | ENST00000373023 | chr1_38397372-38397372_C_A | 249A>S | Substitution | Nonsynonymous coding | 84% | 123 | 358 |
| CGLI 55 PT | NM_001100111 | Uncharacterized protein | NM_001100111 | chr9_91262344-91262344__TGG | NA | Insertion | In-frame insertion | 84% | 37 | 61 |
| CGLI 55 PT | FUCA1 | fucosidase, alpha-L- 1, tissue | CCDS244.2 | chr1_24180962-24180962_T_C | 286Q>R | Substitution | Nonsynonymous coding | 84% | 37 | 74 |
| CGLI 55 PT | AK5 | adenylate kinase 5 | CCDS675.1 | chr1_78024348-78024348__TAT | NA | Insertion | In-frame insertion | 83% | 5 | 171 |
| CGLI 55 PT | DCLRE1B | DNA cross-link repair 1B | CCDS866.1 | chr1_114453974-114453974_A_G | 254I>V | Substitution | Nonsynonymous coding | 83% | 158 | 438 |
| CGLI 55 PT | MRPS34 | mitochondrial ribosomal protein S34 | CCDS10444.1 | chr16_1822798-1822798__ACCT | NA | Insertion | Splice site donor | 82% | 28 | 147 |
| CGLI 55 PT | ITGA8 | integrin, alpha 8 | CCDS31155.1 | chr10_15814323-15814323_C_T | 842V>M | Substitution | Nonsynonymous coding | 82% | 18 | 66 |
| CGLI 55 PT | OR52A1 | olfactory receptor, family 52, subfamily A, member 1 | CCDS31374.1 | chr11_5172796-5172796__C | NA | Insertion | Frameshift | 82% | 72 | 249 |
| CGLI 55 PT | GUCY2F | Retinal guanylyl cyclase 2;GUCY2F;ortholog | CCDS14545.1 | chrX_108641850-108641850_T_C | S735G | Substitution | nonsynonymous SNV | 81% | 21 | 63 |
| CGLI 55 PT | FHOD3 | formin homology 2 domain containing 3 | CCDS32816.1 | chr18_33935547-33935547_G_A | 71D>N | Substitution | Nonsynonymous coding | 81% | 84 | 100 |
| CGLI 55 PT | CDH23 | cadherin-related 23 | NM_022124 | chr10_73550117-73550117_C_G | 1999T>S | Substitution | Nonsynonymous coding | 80% | 86 | 101 |
| CGLI 55 PT | CPS1 | carbamoyl-phosphate synthase 1, mitochondrial | CCDS46505.1 | chr2_211421453-211421453__TCT | NA | Insertion | In-frame insertion | 80% | 28 | 103 |
| CGLI 55 PT | USP54 | ubiquitin specific peptidase 54 | CCDS7329.2 | chr10_75258443-75258443_C_T | 1687D>N | Substitution | Nonsynonymous coding | 79% | 31 | 329 |
| CGLI 55 PT | EBLN2 | endogenous Bornavirus-like nucleoprotein 2 | NM_018029 | chr3_73111504-73111504__TGG | NA | Insertion | In-frame insertion | 79% | 114 | 156 |
| CGLI 55 PT | TCF4 | Transcription factor 4;TCF4;ortholog | CCDS58623.1 | chr18_52946848-52946848_C_T | D37N | Substitution | nonsynonymous SNV | 79% | 44 | 34 |
| CGLI 55 PT | PARP1 | poly (ADP-ribose) polymerase 1 | ENST00000366791 | chr1_226580652-226580652_T_A | 108M>L | Substitution | Nonsynonymous coding | 78% | 7 | 39 |
| CGLI 55 PT | CSDE1 | Cold shock domain-containing protein E1;CSDE1;ortholog | CCDS30811.1 | chr1_115272935-115272935_T_G | K403Q | Substitution | nonsynonymous SNV | 78% | 35 | 63 |
| CGLI 55 PT | CSDE1 | cold shock domain containing E1, RNA-binding | CCDS44197.1 | chr1_115272935-115272935_T_G | 449K>Q | Substitution | Nonsynonymous coding | 77% | 34 | 161 |
| CGLI 55 PT | BBS5 | Bardet-Biedl syndrome 5 | CCDS2233.1 | chr2_170358065-170358065_A_G | 251N>D | Substitution | Nonsynonymous coding | 77% | 10 | 100 |
| CGLI 55 PT | ARHGEF10L | Rho guanine nucleotide exchange factor (GEF) 10-like | ENST00000375408 | chr1_17944885-17944885_C_T | 13R>X | Substitution | Nonsense | 76% | 35 | 56 |
| CGLI 55 PT | FOXD3 | forkhead box D3 | CCDS624.1 | chr1_63788890-63788890_G_A | 54R>H | Substitution | Nonsynonymous coding | 76% | 38 | 52 |
| CGLI 55 PT | ADRB1 | adrenoceptor beta 1 | CCDS7586.1 | chr10_115805230-115805230_C_G | 447P>A | Substitution | Nonsynonymous coding | 75% | 6 | 41 |
| CGLI 55 PT | TUBAL3 | Tubulin alpha chain-like 3;TUBAL3;ortholog | CCDS53491.1 | chr10_5435790-5435790_G_A | S304L | Substitution | nonsynonymous SNV | 74% | 46 | 34 |
| CGLI 55 PT | CDCP2 | CUB domain containing protein 2 | CCDS568.2 | chr1_54605320-54605320__C | NA | Insertion | Frameshift | 74% | 89 | 77 |

Fig. 8 (continued)

| Sample | Gene | Description | CCDS/NM | Location | Change | Type | Effect | % | Var reads | Total reads |
|---|---|---|---|---|---|---|---|---|---|---|
| CGLI 55 PT | TCF4 | transcription factor 4 | CCDS42438.1 | chr18_52946848-52946848_C_T | 197D>N | Substitution | Nonsynonymous coding | 74% | 43 | 87 |
| CGLI 55 PT | FHOD3 | FH1/FH2 domain-containing protein 3;FHOD3;ortholog | CCDS32818.1 | chr18_33935547-33935547_G_A | D71N | Substitution | nonsynonymous SNV | 72% | 46 | 63 |
| CGLI 55 PT | BCOR | BCL-6 corepressor;BCOR;ortholog | CCDS48092.1 | chrX_39922069-39922069__A | L1316fs | Insertion | frameshift insertion | 71% | 35 | 63 |
| CGLI 55 PT | KIAA0319L | Dyslexia-associated protein KIAA0319-like protein;KIAA0319L;ortholog | CCDS390.1 | chr1_35921709-35921709_T_G | T521P | Substitution | nonsynonymous SNV | 71% | 36 | 63 |
| CGLI 55 PT | DCLRE1B | 5' exonuclease Apollo;DCLRE1B;ortholog | CCDS866.1 | chr1_114453974-114453974_A_G | I254V | Substitution | nonsynonymous SNV | 70% | 80 | 63 |
| CGLI 55 PT | E2F8 | E2F transcription factor 8 | CCDS7849.1 | chr11_19251410-19251410_C_T | 486G>E | Substitution | Nonsynonymous coding | 70% | 54 | 104 |
| CGLI 55 PT | AMPH | amphiphysin | CCDS5456.1 | chr7_38514968-38514968_C_T | 185V>I | Substitution | Nonsynonymous coding | 70% | 7 | 109 |
| CGLI 55 PT | CLSTN3 | calsyntenin 3 | CCDS8575.1 | chr12_7283287-7283287_G_T | 15A>S | Substitution | Nonsynonymous coding | 69% | 9 | 28 |
| CGLI 55 PT | PRB2 | proline-rich protein BstNI subfamily 2 | CCDS8642.1 | chr12_11506066-11506066_C_T | 191G>D | Substitution | Nonsynonymous coding | 69% | 11 | 30 |
| CGLI 55 PT | USP26 | Ubiquitin carboxyl-terminal hydrolase 26;USP26;ortholog | CCDS14635.1 | chrX_132161880-132161880__TGT | T123delinsTQ | Insertion | nonframeshift insertion | 68% | 27 | 63 |
| CGLI 55 PT | SOD2 | superoxide dismutase 2, mitochondrial | CCDS5265.1 | chr6_160113872-160113872_A_G | 16V>A | Substitution | Nonsynonymous coding | 67% | 74 | 216 |
| CGLI 55 PT | BCOR | BCL6 corepressor | CCDS48093.1 | chrX_39922069-39922069__A | NA | Insertion | Frameshift | 66% | 71 | 176 |
| CGLI 55 PT | TCHH | trichohyalin | CCDS41396.1 | chr1_152083325-152083325_A_T | 790L>M | Substitution | Nonsynonymous coding | 66% | 370 | 529 |
| CGLI 55 PT | PTEN | phosphatase and tensin homolog | NM_000314 | chr10_89692904-89692904_C_T | 130R>X | Substitution | Nonsense | 66% | 29 | 250 |
| CGLI 55 PT | PTEN | Phosphatidylinositol 3,4,5-bisphosphate 3-phosphatase and dual-specificity protein phosphatase PTEN;PTEN;ortholog | CCDS31238.1 | chr10_89692904-89692904_C_T | R130X | Substitution | stopgain | 65% | 34 | 34 |
| CGLI 55 PT | VPS72 | vacuolar protein sorting 72 homolog (S. cerevisiae) | CCDS989.1 | chr1_151149427-151149427_C_T | 263R>H | Substitution | Nonsynonymous coding | 65% | 63 | 106 |
| CGLI 55 PT | CFTR | cystic fibrosis transmembrane conductance regulator (ATP-binding cassette sub-family C, member 7) | CCDS5773.1 | chr7_117199533-117199533_G_A | 470V>M | Substitution | Nonsynonymous coding | 63% | 24 | 117 |
| CGLI 55 PT | LYST | lysosomal trafficking regulator | CCDS31062.1 | chr1_235973189-235973189_C_T | 317E>K | Substitution | Nonsynonymous coding | 63% | 102 | 313 |
| CGLI 55 PT | CEP290 | centrosomal protein 290kDa | NM_025114 | chr12_88462336-88462336_T_C | 2033E>G | Substitution | Nonsynonymous coding | 63% | 5 | 103 |
| CGLI 55 PT | COL22A1 | collagen, type XXII, alpha 1 | CCDS6376.1 | chr8_139649029-139649029_C_T | 1171G>R | Substitution | Nonsynonymous coding | 62% | 51 | 178 |
| CGLI 55 PT | SPTA1 | spectrin, alpha, erythrocytic 1 (elliptocytosis 2) | CCDS41423.1 | chr1_158624528-158624528_G_T | 970A>D | Substitution | Nonsynonymous coding | 62% | 55 | 42 |
| CGLI 55 PT | PEAR1 | platelet endothelial aggregation receptor 1 | CCDS30892.1 | chr1_156876618-156876618_C_T | 197P>L | Substitution | Nonsynonymous coding | 61% | 200 | 186 |
| CGLI 55 PT | CCDC159 | coiled-coil domain containing 159 | ENST00000327804 | chr19_11459267-11459267_G_A | 153R>H | Substitution | Nonsynonymous coding | 60% | 49 | 266 |
| CGLI 55 PT | RPGRIP1 | retinitis pigmentosa GTPase regulator interacting protein 1 | CCDS45080.1 | chr14_21769193-21769193_C_A | 96P>Q | Substitution | Nonsynonymous coding | 60% | 88 | 170 |
| CGLI 55 PT | RANBP3L | RAN binding protein 3-like | CCDS3918.1 | chr5_36257108-36257108_G_A | 260R>X | Substitution | Nonsense | 60% | 15 | 100 |
| CGLI 55 PT | RECQL5 | RecQ protein-like 5 | CCDS42390.1 | chr17_73826919-73826919__TG | NA | Insertion | Splice site acceptor | 59% | 68 | 152 |
| CGLI 55 PT | OBSCN | obscurin, cytoskeletal calmodulin and titin-interacting RhoGEF | NM_001098623 | chr1_228503722-228503722_G_A | 4396R>H | Substitution | Nonsynonymous coding | 59% | 135 | 143 |
| CGLI 55 PT | CA14 | Carbonic anhydrase 14;CA14;ortholog | CCDS947.1 | chr1_150234988-150234988_A_T | Q155L | Substitution | nonsynonymous SNV | 59% | 28 | 63 |
| CGLI 55 PT | RANBP3L | Ran-binding protein 3-like;RANBP3L;ortholog | CCDS3918.1 | chr5_36257108-36257108_G_A | R260X | Substitution | stopgain | 59% | 23 | 63 |
| CGLI 55 PT | MYO15A | myosin XVA | CCDS42271.1 | chr17_18082172-18082172_C_ | NA | Deletion | Frameshift | 59% | 83 | 262 |
| CGLI 55 PT | FMO6P | flavin containing monooxygenase 6 pseudogene | ENST00000236166 | chr1_171118739-171118739_G_A | 223R>Q | Substitution | Nonsynonymous coding | 59% | 41 | 80 |
| CGLI 55 PT | CR2 | complement component (3d/Epstein Barr virus) receptor 2 | CCDS31007.1 | chr1_207648424-207648424_A_G | 880K>R | Substitution | Nonsynonymous coding | 59% | 106 | 222 |
| CGLI 55 PT | MYO15A | Unconventional myosin-XV;MYO15A;ortholog | CCDS42271.1 | chr17_18082172-18082172_C_ | Y236C | Deletion | frameshift deletion | 59% | 24 | 63 |
| CGLI 55 PT | PP13004 | Uncharacterized protein | ENST00000381493 | chr7_36124232-36124232__T | NA | Insertion | Frameshift | 58% | 66 | 132 |
| CGLI 55 PT | RAD51AP2 | RAD51 associated protein 2 | CCDS42656.1 | chr2_17697216-17697216_C_T | 823E>K | Substitution | Nonsynonymous coding | 58% | 14 | 233 |
| CGLI 55 PT | RFX6 | regulatory factor X, 6 | CCDS5113.1 | chr6_117199661-117199661_G_C | 75E>Q | Substitution | Nonsynonymous coding | 58% | 45 | 54 |
| CGLI 55 PT | VPS72 | Vacuolar protein sorting-associated protein 72 homolog;VPS72;ortholog | CCDS59201.1 | chr1_151149427-151149427_C_T | R274H | Substitution | nonsynonymous SNV | 58% | 49 | 63 |

Fig. 8 (continued)

| | | | | | | | | | |
|---|---|---|---|---|---|---|---|---|---|
| CGLI 55 PT | RHBG | Rh family, B glycoprotein (gene/pseudogene) | ENST00000255013 | chr1_156354348-156354348_C_ | NA | Deletion | Splice site acceptor | 57% | 245 | 272 |
| CGLI 55 PT | FMO3 | flavin containing monooxygenase 3 | CCDS1292.1 | chr1_171076966-171076966_G_A | 158E>K | Substitution | Nonsynonymous coding | 57% | 59 | 149 |
| CGLI 55 PT | GIN1 | gypsy retrotransposon integrase 1 | CCDS43349.1 | chr5_102444333-102444333_T_C | 27T>A | Substitution | Nonsynonymous coding | 57% | 12 | 135 |
| CGLI 55 PT | POLR2D | polymerase (RNA) II (DNA directed) polypeptide D | CCDS2161.1 | chr2_128610553-128610553_T_C | 67Y>C | Substitution | Nonsynonymous coding | 57% | 24 | 291 |
| CGLI 55 PT | TPMT | thiopurine S-methyltransferase | CCDS4543.1 | chr6_18139228-18139228_C_T | 154A>T | Substitution | Nonsynonymous coding | 57% | 8 | 86 |
| CGLI 55 PT | TRPV6 | transient receptor potential cation channel, subfamily V, member 6 | CCDS5874.1 | chr7_142572908-142572908_T_C | 378M>V | Substitution | Nonsynonymous coding | 57% | 28 | 152 |
| CGLI 55 PT | UTP6 | UTP6, small subunit (SSU) processome component, homolog (yeast) | CCDS11269.1 | chr17_30216347-30216347_C_G | 167R>P | Substitution | Nonsynonymous coding | 57% | 8 | 89 |
| CGLI 55 PT | TRAPPC11 | trafficking protein particle complex 11 | CCDS34112.1 | chr4_184615880-184615880__T | NA | Insertion | Splice site donor | 57% | 4 | 31 |
| CGLI 55 PT | CDAN1 | codanin 1 | CCDS32209.1 | chr15_43020983-43020983_G_A | 891R>C | Substitution | Nonsynonymous coding | 57% | 73 | 248 |
| CGLI 55 PT | OR4S2 | olfactory receptor, family 4, subfamily S, member 2 | CCDS31505.1 | chr11_55418453-55418453_G_C | 25C>S | Substitution | Nonsynonymous coding | 57% | 37 | 117 |
| CGLI 55 PT | TEKT5 | tektin 5 | CCDS10542.1 | chr16_10783809-10783809_T_C | 213N>S | Substitution | Nonsynonymous coding | 57% | 37 | 234 |
| CGLI 55 PT | DNHD1 | dynein heavy chain domain 1 | CCDS44532.1 | chr11_6587907-6587907_T_G | 3766L>W | Substitution | Nonsynonymous coding | 57% | 112 | 184 |
| CGLI 55 PT | BSN | bassoon presynaptic cytomatrix protein | CCDS2800.1 | chr3_49680041-49680041_C_T | 325P>L | Substitution | Nonsynonymous coding | 58% | 138 | 369 |
| CGLI 55 PT | TRMT5 | tRNA (guanine(37)-N1)-methyltransferase;TRMT5 ;ortholog | CCDS32092.1 | chr14_61442592-61442592_C_T | V349M | Substitution | nonsynonymous SNV | 56% | 49 | 34 |
| CGLI 55 PT | EDC4 | enhancer of mRNA decapping 4 | CCDS10848.1 | chr16_67814054-67814054_C_T | 878R>C | Substitution | Nonsynonymous coding | 56% | 49 | 189 |
| CGLI 55 PT | TMEM209 | transmembrane protein 209 | CCDS47712.1 | chr7_129843690-129843690__A | NA | insertion | Splice site acceptor | 56% | 9 | 148 |
| CGLI 55 PT | GOLGB1 | golgin B1 | CCDS3004.1 | chr3_121417710-121417710_C_G | 549E>Q | Substitution | Nonsynonymous coding | 56% | 14 | 119 |
| CGLI 55 PT | ITGB6 | integrin, beta 6 | CCDS2212.1 | chr2_160993992-160993992_T_C | 538Q>R | Substitution | Nonsynonymous coding | 56% | 52 | 168 |
| CGLI 55 PT | TMEM37 | transmembrane protein 37 | CCDS33281.1 | chr2_120194652-120194652_C_G | 70T>R | Substitution | Nonsynonymous coding | 56% | 20 | 427 |
| CGLI 55 PT | CDK5RAP1 | CDK5 regulatory subunit associated protein 1 | CCDS13219.1 | chr20_31958393-31958393_T_C | 435E>G | Substitution | Nonsynonymous coding | 55% | 37 | 152 |
| CGLI 55 PT | RASGRF2 | Ras-specific guanine nucleotide-releasing factor 2;RASGRF2;ortholog | CCDS4052.1 | chr5_80419475-80419475_G_C | A829P | Substitution | nonsynonymous SNV | 55% | 16 | 34 |
| CGLI 55 PT | PYCR2 | pyrroline-5-carboxylate reductase family, member 2 | CCDS31043.1 | chr1_226110062-226110062_G_A | 54R>C | Substitution | Nonsynonymous coding | 55% | 161 | 187 |
| CGLI 55 PT | AKAP8 | A kinase (PRKA) anchor protein 8 | CCDS12329.1 | chr19_15484762-15484762_G_C | 89A>G | Substitution | Nonsynonymous coding | 55% | 54 | 17 |
| CGLI 55 PT | PRRX1 | paired related homeobox 1 | CCDS1290.1 | chr1_170705313-170705313_C_T | 242P>S | Substitution | Nonsynonymous coding | 55% | 54 | 19 |
| CGLI 55 PT | HEXIM2 | hexamethylene bis-acetamide inducible 2 | CCDS11496.1 | chr17_43246907-43246907_C_G | 198E>Q | Substitution | Nonsynonymous coding | 55% | 120 | 221 |
| CGLI 55 PT | DICER1 | dicer 1, ribonuclease type III | CCDS9931.1 | chr14_95584087-95584087_T_C | 461I>V | Substitution | Nonsynonymous coding | 55% | 11 | 77 |
| CGLI 55 PT | TAP1 | transporter 1, ATP-binding cassette, sub-family B (MDR/TAP) | CCDS4758.1 | chr6_32814975-32814975_T_C | 697D>G | Substitution | Nonsynonymous coding | 55% | 56 | 88 |
| CGLI 55 PT | DISC1 | disrupted in schizophrenia 1 | CCDS31055.1 | chr1_231854101-231854101_C_T | 807L>F | Substitution | Nonsynonymous coding | 55% | 45 | 24 |
| CGLI 55 PT | WDR43 | WD repeat domain 43 | CCDS46251.1 | chr2_29135488-29135488_C_G | 173S>C | Substitution | Nonsynonymous coding | 55% | 34 | 62 |
| CGLI 55 PT | COG6 | Conserved oligomeric Golgi complex subunit 6;COG6;ortholog | CCDS9370.1 | chr13_40325093-40325093_G_A | V613I | Substitution | nonsynonymous SNV | 55% | 23 | 63 |
| CGLI 55 PT | MSL2 | male-specific lethal 2 homolog (Drosophila) | CCDS33861.1 | chr3_135870440-135870440_A_G | 426L>P | Substitution | Nonsynonymous coding | 54% | 37 | 440 |
| CGLI 55 PT | THOC5 | THO complex 5 | CCDS13859.1 | chr22_29945063-29945063_C_T | 25R>Q | Substitution | Nonsynonymous coding | 54% | 37 | 112 |
| CGLI 55 PT | TEKT5 | Tektin-5;TEKT5;ortholog | CCDS10542.1 | chr16_10783809-10783809_T_C | N213S | Substitution | nonsynonymous SNV | 54% | 37 | 63 |
| CGLI 55 PT | UNK | unkempt homolog (Drosophila) | CCDS45778.1 | chr17_73819472-73819472_C_G | 792E>Q | Substitution | Nonsynonymous coding | 54% | 56 | 119 |
| CGLI 55 PT | RYR1 | ryanodine receptor 1 (skeletal) | CCDS33011.1 | chr19_38933022-38933022_G_A | 87V>I | Substitution | Nonsynonymous coding | 54% | 13 | 73 |
| CGLI 55 PT | E2F8 | Transcription factor E2F8;E2F8;ortholog | CCDS7849.1 | chr11_19251410-19251410_C_T | G495E | Substitution | nonsynonymous SNV | 54% | 27 | 63 |
| CGLI 55 PT | ADAMTSL3 | ADAMTS-like 3 | CCDS10326.1 | chr15_84651394-84651394_G_A | 1005R>H | Substitution | Nonsynonymous coding | 54% | 116 | 260 |
| CGLI 55 PT | KIAA1024 | KIAA1024 | CCDS32306.1 | chr15_79760682-79760682_G_A | 803V>I | Substitution | Nonsynonymous coding | 54% | 21 | 75 |
| CGLI 55 PT | LANCL2 | LanC lantibiotic synthetase component C-like 2 (bacterial) | CCDS5517.1 | chr7_55496118-55496118_C_G | 412D>E | Substitution | Nonsynonymous coding | 54% | 42 | 49 |
| CGLI 55 PT | RASGRF2 | Ras protein-specific guanine nucleotide-releasing factor 2 | CCDS4052.1 | chr5_80419475-80419475_G_C | 829A>P | Substitution | Nonsynonymous coding | 54% | 14 | 72 |

Fig. 8 (continued)

| Sample | Gene | Description | CCDS | Location | Change | Type | Coding Effect | % | Alt | Total |
|---|---|---|---|---|---|---|---|---|---|---|
| CGLI 55 PT | TRMT5 | tRNA methyltransferase 5 homolog (S. cerevisiae) | CCDS32092.1 | chr14_61442592-61442592_C_T | 349V>M | Substitution | Nonsynonymous coding | 54% | 65 | 273 |
| CGLI 55 PT | MZF1 | myeloid zinc finger 1 | CCDS12988.1 | chr19_59074226-59074226__G | NA | Insertion | Frameshift | 54% | 52 | 80 |
| CGLI 55 PT | TP53 | tumor protein p53 | CCDS11118.1 | chr17_7579472-7579472_G_C | 72P>R | Substitution | Nonsynonymous coding | 53% | 31 | 93 |
| CGLI 55 PT | CYP1A1 | Cytochrome P450 1A1;CYP1A1;ortholog | CCDS10268.1 | chr15_75015123-75015123_G_ | R106fs | Deletion | frameshift deletion | 53% | 31 | 34 |
| CGLI 55 PT | MEFV | Mediterranean fever | CCDS10498.1 | chr16_3293407-3293407_T_C | 694M>V | Substitution | Nonsynonymous coding | 53% | 98 | 425 |
| CGLI 55 PT | MSL2 | E3 ubiquitin-protein ligase MSL2;MSL2;ortholog | CCDS46922.1 | chr3_135870440-135870440_A_G | L354P | Substitution | nonsynonymous SNV | 53% | 33 | 63 |
| CGLI 55 PT | GPR149 | Probable G-protein coupled receptor 149;GPR149;ortholog | CCDS43162.1 | chr3_154146926-154146926_G_A | A160V | Substitution | nonsynonymous SNV | 53% | 17 | 63 |
| CGLI 55 PT | ANKRD11 | ankyrin repeat domain 11 | CCDS32513.1 | chr16_89346885-89346885_G_A | 2022P>L | Substitution | Nonsynonymous coding | 53% | 43 | 86 |
| CGLI 55 PT | USP26 | ubiquitin specific peptidase 26 | CCDS14635.1 | chrX_132161880-132161880__TGT | NA | Insertion | in-frame insertion | 53% | 26 | 390 |
| CGLI 55 PT | ARID3C | AT-rich interactive domain-containing protein 3C;ARID3C;ortholog | CCDS35006.1 | chr9_34621480-34621480_G_A | P412S | Substitution | nonsynonymous SNV | 53% | 18 | 63 |
| CGLI 55 PT | SEMA6A | sema domain, transmembrane domain (TM), and cytoplasmic domain, (semaphorin) 6A | CCDS47256.1 | chr5_115762611-115762611_C_G | 931A>P | Substitution | Nonsynonymous coding | 53% | 110 | 445 |
| CGLI 55 PT | LACC1 | laccase (multicopper oxidoreductase) domain containing 1 | CCDS59391.1 | chr13_44457925-44457925_A_G | 254I>V | Substitution | Nonsynonymous coding | 53% | 28 | 60 |
| CGLI 55 PT | CA14 | carbonic anhydrase XIV | CCDS947.1 | chr1_150234988-150234988_A_T | 155Q>L | Substitution | Nonsynonymous coding | 53% | 57 | 272 |
| CGLI 55 PT | DCTN1 | Dynactin subunit 1;DCTN1;ortholog | CCDS46342.1 | chr2_74598840-74598840_T_C | S23G | Substitution | nonsynonymous SNV | 53% | 19 | 34 |
| CGLI 55 PT | RTFDC1 | Protein RTF2 homolog;RTFDC1;ortholog | CCDS13453.1 | chr20_55088381-55088381_C_T | A183V | Substitution | nonsynonymous SNV | 53% | 19 | 34 |
| CGLI 55 PT | C9orf37 | chromosome 9 open reading frame 37 | CCDS35186.1 | chr9_140510219-140510219_C_A | 145V>F | Substitution | Nonsynonymous coding | 53% | 100 | 257 |
| CGLI 55 PT | CYP1B1 | cytochrome P450, family 1, subfamily B, polypeptide 1 | CCDS1793.1 | chr2_38302177-38302177_C_A | 119A>S | Substitution | Nonsynonymous coding | 53% | 73 | 92 |
| CGLI 55 PT | EDC4 | Enhancer of mRNA-decapping protein 4;EDC4;ortholog | CCDS10849.1 | chr16_67914054-67914054_C_T | R678C | Substitution | nonsynonymous SNV | 53% | 21 | 34 |
| CGLI 55 PT | AOAH | acyloxyacyl hydrolase (neutrophil) | CCDS5448.1 | chr7_36763728-36763728_G_A | 9T>M | Substitution | Nonsynonymous coding | 52% | 45 | 131 |
| CGLI 55 PT | DNAH6 | dynein, axonemal, heavy chain 6 | CCDS46348.1 | chr2_84777063-84777063_C_T | 456T>M | Substitution | Nonsynonymous coding | 52% | 12 | 214 |
| CGLI 55 PT | FSIP2 | fibrous sheath interacting protein 2 | ENST00000424728 | chr2_186672469-186672469_G_C | 6146V>L | Substitution | Nonsynonymous coding | 52% | 26 | 153 |
| CGLI 55 PT | OR5P2 | olfactory receptor, family 5, subfamily P, member 2 | CCDS7782.1 | chr11_7818383-7818383_G_C | 36S>C | Substitution | Nonsynonymous coding | 52% | 13 | 50 |
| CGLI 55 PT | RAB11FIP5 | RAB11 family interacting protein 5 (class I) | CCDS1923.1 | chr2_73315658-73315658_G_A | 383P>L | Substitution | Nonsynonymous coding | 52% | 139 | 290 |
| CGLI 55 PT | ESPNL | espin-like | CCDS2525.1 | chr2_239038949-239038949_C_T | 532R>W | Substitution | Nonsynonymous coding | 52% | 101 | 116 |
| CGLI 55 PT | ZFP28 | ZFP28 zinc finger protein | CCDS12946.1 | chr19_57060359-57060359_C_T | 158P>S | Substitution | Nonsynonymous coding | 52% | 16 | 91 |
| CGLI 55 PT | NELFA | negative elongation factor complex member A | CCDS3358.2 | chr4_1985627-1985627_G_A | 426P>L | Substitution | Nonsynonymous coding | 52% | 82 | 237 |
| CGLI 55 PT | DNAH10 | dynein, axonemal, heavy chain 10 | CCDS9255.2 | chr12_124397795-124397795_G_A | 3311E>K | Substitution | Nonsynonymous coding | 52% | 33 | 90 |
| CGLI 55 PT | TRPV6 | transient receptor potential cation channel, subfamily V, member 6 | CCDS55874.1 | chr7_142569596-142569596_A_G | 681M>T | Substitution | Nonsynonymous coding | 52% | 100 | 431 |
| CGLI 55 PT | COG6 | component of oligomeric golgi complex 6 | CCDS9370.1 | chr13_40325093-40325093_G_A | 613V>I | Substitution | Nonsynonymous coding | 52% | 17 | 161 |
| CGLI 55 PT | COPB2 | Coatomer subunit beta';COPB2;ortholog | CCDS3198.1 | chr3_139081332-139081332_A_T | 563I>T | Substitution | nonsynonymous SNV | 52% | 17 | 83 |
| CGLI 55 PT | USE1 | unconventional SNARE in the ER 1 homolog (S. cerevisiae) | CCDS46011.1 | chr17_17330066-17330066_C_T | 156A>V | Substitution | Nonsynonymous coding | 51% | 71 | 95 |
| CGLI 55 PT | DNAH6 | dynein, axonemal, heavy chain 6 | CCDS46348.1 | chr2_84924774-84924774_G_A | 2534D>N | Substitution | Nonsynonymous coding | 51% | 38 | 105 |
| CGLI 55 PT | FSIP2 | Fibrous sheath-interacting protein 2;FSIP2;ortholog | CCDS54426.1 | chr2_186672469-186672469_G_C | V6235L | Substitution | nonsynonymous SNV | 51% | 38 | 83 |
| CGLI 55 PT | RP3-402G11.5 | selenoprotein O | ENST00000400018 | chr22_50649274-50649274_G_A | 429V>M | Substitution | Nonsynonymous coding | 51% | 97 | 169 |
| CGLI 55 PT | PSMD13 | proteasome (prosome, macropain) 26S subunit, non-ATPase, 13 | CCDS44504.1 | chr11_244127-244127_G_A | 61R>Q | Substitution | Nonsynonymous coding | 51% | 20 | 78 |
| CGLI 55 PT | SMG6 | smg-6 homolog, nonsense mediated mRNA decay factor (C. elegans) | CCDS11016.1 | chr17_2203212-2203212_G_A | 279R>C | Substitution | Nonsynonymous coding | 51% | 141 | 729 |
| CGLI 55 PT | MLH1 | mutL homolog 1, colon cancer, nonpolyposis type 2 (E. coli) | CCDS2663.1 | chr3_37035130-37035130_C_G | 31A>G | Substitution | Nonsynonymous coding | 51% | 81 | 138 |

Fig. 8 (continued)

| | | | | | | | | | |
|---|---|---|---|---|---|---|---|---|---|
| CGLI 55 PT | MRI1 | methylthioribose-1-phosphate isomerase homolog (S. cerevisiae) | CCDS32923.1 | chr19_13879797-13879797_T_A | 295I>N | Substitution | Nonsynonymous coding | 51% | 109 | 345 |
| CGLI 55 PT | OR7E24 | olfactory receptor, family 7, subfamily E, member 24 | CCDS45955.1 | chr19_9362285-9362285_A_C | 189D>A | Substitution | Nonsynonymous coding | 51% | 68 | 432 |
| CGLI 55 PT | GAS6 | growth arrest-specific 6 | CCDS45072.1 | chr13_114526409-114526409_C_T | 521R>H | Substitution | Nonsynonymous coding | 51% | 94 | 137 |
| CGLI 55 PT | BSN | bassoon presynaptic cytomatrix protein | CCDS2860.1 | chr3_49689585-49689585_G_A | 666G>R | Substitution | Nonsynonymous coding | 51% | 132 | 117 |
| CGLI 55 PT | INPP5J | inositol polyphosphate-5-phosphatase J | ENST00000331075 | chr22_31520993-31520993_T_G | 90C>G | Substitution | Nonsynonymous coding | 51% | 186 | 439 |
| CGLI 55 PT | MLH1 | mutL homolog 1, colon cancer, nonpolyposis type 2 (E. coli) | CCDS2663.1 | chr3_37035129-37035129_G_T | 31A>S | Substitution | Nonsynonymous coding | 51% | 62 | 143 |
| CGLI 55 PT | SLC9A3 | solute carrier family 9, subfamily A (NHE3, cation proton antiporter 3), member 3 | CCDS3855.1 | chr5_478734-478734_C_T | 805R>Q | Substitution | Nonsynonymous coding | 51% | 56 | 285 |
| CGLI 55 PT | SLC10A2 | solute carrier family 10 (sodium/bile acid cotransporter family), member 2 | CCDS9506.1 | chr13_103718463-103718463_A_G | 46M>T | Substitution | Nonsynonymous coding | 51% | 57 | 354 |
| CGLI 55 PT | ZNF610 | zinc finger protein 610 | CCDS12851.1 | chr19_52869721-52869721_A_G | 364I>V | Substitution | Nonsynonymous coding | 51% | 37 | 249 |
| CGLI 55 PT | ZNF513 | zinc finger protein 513 | CCDS1751.1 | chr2_27601988-27601988_C_T | 317R>Q | Substitution | Nonsynonymous coding | 51% | 205 | 170 |
| CGLI 55 PT | DAAM2 | dishevelled associated activator of morphogenesis 2 | NM_015345 | chr6_39889812-39889812_G_T | 1068?>L | Substitution | Nonsynonymous coding | 50% | 53 | 84 |
| CGLI 55 PT | FURIN | furin (paired basic amino acid cleaving enzymes) | CCDS10364.1 | chr15_91420189-91420189_G_A | 148G>S | Substitution | Nonsynonymous coding | 50% | 113 | 253 |
| CGLI 55 PT | COL4A2 | collagen, type IV, alpha 2 | CCDS41907.1 | chr13_111156592-111156592_G_T | 1461Q>H | Substitution | Nonsynonymous coding | 50% | 59 | 136 |
| CGLI 55 PT | DAPK3 | death-associated protein kinase 3 | CCDS12116.1 | chr19_3959299-3959299_C_T | 389E>K | Substitution | Nonsynonymous coding | 50% | 121 | 268 |
| CGLI 55 PT | OTOF | otoferlin | CCDS1725.1 | chr2_26717944-26717944_G_A | NA | Substitution | Splice site acceptor | 50% | 68 | 171 |
| CGLI 55 PT | OBSL1 | obscurin-like 1 | CCDS46520.1 | chr2_220422963-220422963_C_T | 1149G>R | Substitution | Nonsynonymous coding | 50% | 105 | 220 |
| CGLI 55 PT | EPYC | Epiphycan;EPYC;ortholog | CCDS31870.1 | chr12_91365698-91365698_C_T | R194Q | Substitution | nonsynonymous SNV | 50% | 12 | 34 |
| CGLI 55 PT | CKAP4 | Cytoskeleton-associated protein 4;CKAP4;ortholog | CCDS9193.1 | chr12_106641268-106641268_G_A | A121V | Substitution | nonsynonymous SNV | 50% | 10 | 83 |
| CGLI 55 PT | ADAM23 | Disintegrin and metalloproteinase domain-containing protein 23;ADAM23;ortholog | CCDS2369.1 | chr2_207345965-207345965_G_T | Q154H | Substitution | nonsynonymous SNV | 50% | 26 | 80 |
| CGLI 55 PT | GIN1 | Gypsy retrotransposon integrase-like protein 1;GIN1;ortholog | CCDS43349.1 | chr5_102444333-102444333_T_C | T27A | Substitution | nonsynonymous SNV | 50% | 30 | 63 |
| CGLI 55 PT | ABO | ABO blood group (transferase A, alpha 1-3-N-acetylgalactosaminyltransferase; transferase B, alpha 1-3-galactosyltransferase) | ENST00000319878 | chr9_136132909-136132909__C | NA | Insertion | Splice site acceptor | 50% | 33 | 249 |
| CGLI 55 PT | ACHE | acetylcholinesterase | CCDS5719.1 | chr7_100490797-100490797_G_T | 353H>N | Substitution | Nonsynonymous coding | 50% | 94 | 146 |
| CGLI 55 PT | BDP1 | B double prime 1, subunit of RNA polymerase III transcription initiation factor IIIB | ENST00000437938 | chr5_70807017-70807017_T_ | NA | Deletion | Frameshift | 50% | 14 | 142 |
| CGLI 55 PT | EPYC | epiphycan | CCDS31870.1 | chr12_91365698-91365698_C_T | 194R>Q | Substitution | Nonsynonymous coding | 50% | 11 | 65 |
| CGLI 55 PT | GPATCH4 | G patch domain containing 4 | ENST00000334568 | chr1_156567679-156567679__T | NA | Insertion | Frameshift | 50% | 66 | 293 |
| CGLI 55 PT | INPP5J | inositol polyphosphate-5-phosphatase J | ENST00000331075 | chr22_31520994-31520994_G_C | 90C>S | Substitution | Nonsynonymous coding | 50% | 186 | 429 |
| CGLI 55 PT | USH2A | Usher syndrome 2A (autosomal recessive, mild) | CCDS31025.1 | chr1_216011408-216011408_T_C | 3099N>S | Substitution | Nonsynonymous coding | 50% | 30 | 36 |
| CGLI 55 PT | DNAJB8 | DnaJ (Hsp40) homolog, subfamily B, member 8 | CCDS53048.1 | chr3_128181847-128181847_G_A | 81T>M | Substitution | Nonsynonymous coding | 50% | 142 | 281 |
| CGLI 55 PT | ARHGEF17 | Rho guanine nucleotide exchange factor (GEF) 17 | CCDS8221.1 | chr11_73021754-73021754_G_A | 691G>R | Substitution | Nonsynonymous coding | 50% | 127 | 219 |
| CGLI 55 PT | FAM193A | family with sequence similarity 193, member A | CCDS33943.1 | chr4_2661700-2661700_C_T | 264S>L | Substitution | Nonsynonymous coding | 50% | 103 | 285 |
| CGLI 55 PT | ZNF526 | zinc finger protein 526 | CCDS12599.1 | chr19_42728658-42728658_A_G | 35T>A | Substitution | Nonsynonymous coding | 50% | 146 | 168 |
| CGLI 55 PT | SLC26A1 | solute carrier family 26 (sulfate transporter), member 1 | CCDS33934.1 | chr4_983483-983483_G_A | 415S>F | Substitution | Nonsynonymous coding | 50% | 63 | 62 |
| CGLI 55 PT | ELL3 | elongation factor RNA polymerase II-like 3 | CCDS10102.1 | chr15_44067975-44067975_G_A | 143T>I | Substitution | Nonsynonymous coding | 50% | 55 | 609 |
| CGLI 55 PT | C21orf2 | chromosome 21 open reading frame 2 | CCDS13709.1 | chr21_45752951-45752951_C_T | 113R>H | Substitution | Nonsynonymous coding | 50% | 50 | 87 |
| CGLI 55 PT | NOS3 | nitric oxide synthase 3 (endothelial cell) | CCDS5912.1 | chr7_150709453-150709453_G_A | 1000R>Q | Substitution | Nonsynonymous coding | 49% | 49 | 80 |

Fig. 8 (continued)

| | | | | | | | | | |
|---|---|---|---|---|---|---|---|---|---|
| CGLI 55 PT | CR2 | Complement receptor type 2;CR2;ortholog | CCDS1478.1 | chr1_207648424-207648424_A_G | K801R | Substitution | nonsynonymous SNV | 49% | 78 | 63 |
| CGLI 55 PT | RASSF8 | Ras association (RalGDS/AF-6) domain family (N-terminal) member 8 | CCDS8705.1 | chr12_26216182-26216182_C_T | 279R>W | Substitution | Nonsynonymous coding | 49% | 73 | 137 |
| CGLI 55 PT | SH3TC1 | SH3 domain and tetratricopeptide repeats 1 | CCDS3399.1 | chr4_8229850-8229850_C_T | 810T>M | Substitution | Nonsynonymous coding | 49% | 174 | 315 |
| CGLI 55 PT | PSMD3 | proteasome (prosome, macropain) 26S subunit, non-ATPase, 3 | CCDS11355.1 | chr17_38151742-38151742_T_G | 426L>V | Substitution | Nonsynonymous coding | 49% | 100 | 156 |
| CGLI 55 PT | CKAP4 | cytoskeleton-associated protein 4 | CCDS9103.1 | chr12_106641266-106641266_G_A | 121A>V | Substitution | Nonsynonymous coding | 49% | 32 | 50 |
| CGLI 55 PT | MLPH | melanophilin | CCDS2518.1 | chr2_238461048-238461048_G_A | 582A>T | Substitution | Nonsynonymous coding | 49% | 31 | 35 |
| CGLI 55 PT | C3 | complement component 3 | CCDS32883.1 | chr19_6713262-6713262_G_A | 314P>L | Substitution | Nonsynonymous coding | 49% | 82 | 247 |
| CGLI 55 PT | INTS2 | integrator complex subunit 2 | CCDS45750.1 | chr17_59984917-59984917_T_C | 353T>A | Substitution | Nonsynonymous coding | 49% | 27 | 292 |
| CGLI 55 PT | GRXCR2 | glutaredoxin, cysteine rich 2 | CCDS34263.1 | chr5_145252312-145252312_G_C | 74Q>E | Substitution | Nonsynonymous coding | 49% | 52 | 349 |
| CGLI 55 PT | HTR3E | 5-hydroxytryptamine (serotonin) receptor 3E, ionotropic | CCDS3251.1 | chr3_183818222-183818222_G_ | NA | Deletion | Frameshift | 49% | 51 | 430 |
| CGLI 55 PT | CABP1 | calcium binding protein 1 | CCDS9205.1 | chr12_121093911-121093911_C_G | 21Q>E | Substitution | Nonsynonymous coding | 49% | 76 | 332 |
| CGLI 55 PT | CD180 | CD180 molecule | CCDS3992.1 | chr5_66479635-66479635_A_G | 346S>P | Substitution | Nonsynonymous coding | 49% | 100 | 215 |
| CGLI 55 PT | SHANK1 | SH3 and multiple ankyrin repeat domains 1 | CCDS12799.1 | chr19_51170685-51170685_G_A | 1511P>L | Substitution | Nonsynonymous coding | 49% | 45 | 141 |
| CGLI 55 PT | VIL1 | villin 1 | CCDS2417.1 | chr2_219299262-219299262_G_A | 505R>Q | Substitution | Nonsynonymous coding | 49% | 45 | 263 |
| CGLI 55 PT | COL27A1 | Collagen alpha-1(XXVII) chain;COL27A1;ortholog | CCDS6802.1 | chr9_116930104-116930104_T_C | I90T | Substitution | nonsynonymous SNV | 49% | 57 | 63 |
| CGLI 55 PT | SETD1A | SET domain containing 1A | CCDS32435.1 | chr16_30975475-30975475_G_T | 234V>L | Substitution | Nonsynonymous coding | 49% | 186 | 367 |
| CGLI 55 PT | TECPR1 | tectonin beta-propeller repeat containing 1 | CCDS47648.1 | chr7_97861169-97861169_C_T | 641G>S | Substitution | Nonsynonymous coding | 49% | 74 | 156 |
| CGLI 55 PT | OBSCN | obscurin, cytoskeletal calmodulin and titin-interacting RhoGEF | ENST00000366707 | chr1_228487177-228487178_AT_ | NA | Deletion | Frameshift | 49% | 181 | 179 |
| CGLI 55 PT | C11orf63 | Uncharacterized protein C11orf63;C11orf63;ortholog | CCDS8438.1 | chr11_122774942-122774944_GGA_ | 218_219del | Deletion | nonframeshift deletion | 48% | 32 | 63 |
| CGLI 55 PT | STRN | Striatin;STRN;ortholog | NULL | chr2_37129726-37129726_C_T | splicing | Substitution | NULL | 48% | 32 | 63 |
| CGLI 55 PT | HSD17B2 | hydroxysteroid (17-beta) dehydrogenase 2 | CCDS10936.1 | chr16_82069197-82069197_G_C | 56W>C | Substitution | Nonsynonymous coding | 48% | 45 | 447 |
| CGLI 55 PT | OSBP2 | Oxysterol-binding protein 2;OSBP2;ortholog | CCDS43002.1 | chr22_31137305-31137305_G_A | A268T | Substitution | nonsynonymous SNV | 48% | 15 | 63 |
| CGLI 55 PT | LPIN3 | lipin 3 | CCDS33469.1 | chr20_39980772-39980772_A_T | 425E>D | Substitution | Nonsynonymous coding | 48% | 103 | 337 |
| CGLI 55 PT | CCDC159 | coiled-coil domain containing 159 | ENST00000427879 | chr19_11459666-11459666__A_ | NA | Insertion | Frameshift | 48% | 131 | 323 |
| CGLI 55 PT | COL22A1 | Collagen alpha-1(XXII) chain;COL22A1;ortholog | CCDS6378.1 | chr8_139649029-139649029_C_T | G1171R | Substitution | nonsynonymous SNV | 48% | 29 | 63 |
| CGLI 55 PT | MYH7B | myosin, heavy chain 7B, cardiac muscle, beta | CCDS42869.1 | chr20_33588193-33588193_G_A | 1669G>S | Substitution | Nonsynonymous coding | 48% | 43 | 91 |
| CGLI 55 PT | DNAH6 | Dynein heavy chain 6, axonemal;DNAH6;ortholog | CCDS46348.1 | chr2_84777063-84777063_C_T | T456M | Substitution | nonsynonymous SNV | 48% | 14 | 34 |
| CGLI 55 PT | NELFA | Negative elongation factor A;NELFA;ortholog | CCDS3358.2 | chr4_1985627-1985627_G_A | P428L | Substitution | nonsynonymous SNV | 48% | 42 | 63 |
| CGLI 55 PT | GLI3 | GLI family zinc finger 3 | CCDS5465.1 | chr7_42004062-42004062_G_A | 1537R>C | Substitution | Nonsynonymous coding | 48% | 92 | 218 |
| CGLI 55 PT | PRB1 | Basic peptide IB-6;PRB1;ortholog | CCDS55805.1 | chr12_11506066-11506066_C_T | G171D | Substitution | nonsynonymous SNV | 48% | 13 | 63 |
| CGLI 55 PT | NEDD4 | E3 ubiquitin-protein ligase NEDD4;NEDD4;ortholog | CCDS10156.1 | chr15_56125236-56125236_C_A | V1180L | Substitution | nonsynonymous SNV | 48% | 13 | 34 |
| CGLI 55 PT | SLC4A2 | solute carrier family 4, anion exchanger, member 2 (erythrocyte membrane protein band 3-like 1) | CCDS5917.1 | chr7_150773112-150773112_C_T | 1162R>C | Substitution | Nonsynonymous coding | 48% | 140 | 164 |
| CGLI 55 PT | STAC | SH3 and cysteine rich domain | CCDS2662.1 | chr3_36526512-36526512_A_G | 178H>R | Substitution | Nonsynonymous coding | 48% | 38 | 378 |
| CGLI 55 PT | MAPK15 | mitogen-activated protein kinase 15 | CCDS6409.2 | chr8_144803727-144803727_C_T | 405R>C | Substitution | Nonsynonymous coding | 48% | 258 | 712 |
| CGLI 55 PT | HECW2 | HECT, C2 and WW domain containing E3 ubiquitin protein ligase 2 | CCDS33354.1 | chr2_197184364-197184364_T_C | 417N>S | Substitution | Nonsynonymous coding | 48% | 61 | 382 |
| CGLI 55 PT | OR52D1 | olfactory receptor, family 52, subfamily D, member 1 | CCDS31384.1 | chr11_5510541-5510541__GGCT | NA | Insertion | Frameshift | 48% | 85 | 597 |
| CGLI 55 PT | MTBP | Mdm2, transformed 3T3 cell double minute 2, p53 binding protein (mouse) binding protein, 104kDa | CCDS6333.1 | chr8_121530200-121530200_C_T | 786P>S | Substitution | Nonsynonymous coding | 48% | 36 | 141 |

Fig. 8 (continued)

| | | | | | | | | | |
|---|---|---|---|---|---|---|---|---|---|
| CGL 55 PT | SARDH | sarcosine dehydrogenase | CCDS6978.1 | chr9_136578159-136578159_C_A | NA | Substitution | Splice site donor | 48% | 58 | 23 |
| CGL 55 PT | SEMA6B | sema domain, transmembrane domain (TM), and cytoplasmic domain, (semaphorin) 6B | CCDS12131.1 | chr19_4552639-4552639_G_A | 262R>C | Substitution | Nonsynonymous coding | 48% | 57 | 54 |
| CGL 55 PT | TTN | Titin;TTN;ortholog | CCDS33337.1 | chr2_179610119-179610119_C_G | V4670L | Substitution | nonsynonymous SNV | 48% | 34 | 63 |
| CGL 55 PT | PCDHA3 | Protocadherin alpha-3;PCDHA3;ortholog | CCDS4915.1 | chr5_140181341-140181341_G_A | E187K | Substitution | nonsynonymous SNV | 48% | 34 | 63 |
| CGL 55 PT | COL27A1 | collagen, type XXVII, alpha 1 | CCDS6802.1 | chr9_116930104-116930104_T_C | 90I>T | Substitution | Nonsynonymous coding | 48% | 135 | 165 |
| CGL 55 PT | TF | transferrin | CCDS3080.1 | chr3_133494354-133494354_C_T | 589P>S | Substitution | Nonsynonymous coding | 48% | 45 | 195 |
| CGL 55 PT | CASR | calcium-sensing receptor | CCDS3010.1 | chr3_122003757-122003757_G_T | 986A>S | Substitution | Nonsynonymous coding | 48% | 201 | 190 |
| CGL 55 PT | IGF2BP2 | insulin-like growth factor 2 mRNA binding protein 2 | CCDS3273.2 | chr3_185376164-185376164_G_A | 412H>Y | Substitution | Nonsynonymous coding | 48% | 78 | 31 |
| CGL 55 PT | OR5P2 | olfactory receptor, family 5, subfamily P, member 2 | CCDS7782.1 | chr11_7818381-7818381_C_T | 37G>S | Substitution | Nonsynonymous coding | 48% | 11 | 52 |
| CGL 55 PT | SETD3 | SET domain containing 3 | CCDS9852.1 | chr14_99876545-99876545_T_G | 286E>A | Substitution | Nonsynonymous coding | 48% | 22 | 18 |
| CGL 55 PT | UNC13C | unc-13 homolog C (C. elegans) | CCDS45264.1 | chr15_54305383-54305383_C_T | 95R>X | Substitution | Nonsense | 48% | 54 | 226 |
| CGL 55 PT | NAT2 | N-acetyltransferase 2 (arylamine N-acetyltransferase) | CCDS58008.1 | chr8_18258103-18258103_G_A | 197R>Q | Substitution | Nonsynonymous coding | 48% | 32 | 292 |
| CGL 55 PT | CCL27 | chemokine (C-C motif) ligand 27 | CCDS6569.1 | chr9_34662623-34662623_C_T | 3G>E | Substitution | Nonsynonymous coding | 48% | 72 | 511 |
| CGL 55 PT | ABO | ABO blood group (transferase A, alpha 1-3-N-acetylgalactosaminyltransferase; transferase B, alpha 1-3-galactosyltransferase) | ENST00000319878 | chr9_136131322-136131322_G_T | 265L>M | Substitution | Nonsynonymous coding | 48% | 133 | 360 |
| CGL 55 PT | GDF6 | growth differentiation factor 6 | CCDS34926.1 | chr8_97172732-97172732_C_G | 63E>D | Substitution | Nonsynonymous coding | 48% | 91 | 299 |
| CGL 55 PT | MFAP1 | microfibrillar-associated protein 1 | CCDS10105.1 | chr15_44102084-44102084_G_A | 306R>C | Substitution | Nonsynonymous coding | 48% | 30 | 368 |
| CGL 55 PT | B3GAT3 | Galactosylgalactosylxylosylprotein 3-beta-glucuronosyltransferase 3;B3GAT3;ortholog | CCDS8025.1 | chr11_62384779-62384779_TCAG_ | L100fs | Deletion | frameshift deletion | 48% | 49 | 34 |
| CGL 55 PT | SPATC1L | Speriolin-like protein;SPATC1L;ortholog | CCDS13732.1 | chr21_47588266-47588266_C_A | S131 | Substitution | nonsynonymous SNV | 48% | 67 | 34 |
| CGL 55 PT | BTBD3 | BTB/POZ domain-containing protein 3;BTBD3;ortholog | CCDS13113.1 | chr20_11903461-11903461_A_T | D239V | Substitution | nonsynonymous SNV | 48% | 38 | 63 |
| CGL 55 PT | TRIM32 | E3 ubiquitin-protein ligase TRIM32;TRIM32;ortholog | CCDS6817.1 | chr9_119461951-119461951_A_G | S644G | Substitution | nonsynonymous SNV | 48% | 19 | 63 |
| CGL 55 PT | GPR149 | G protein-coupled receptor 149 | CCDS43162.1 | chr3_154146926-154146926_G_A | 160A>V | Substitution | Nonsynonymous coding | 48% | 38 | 186 |
| CGL 55 PT | IFNE | interferon, epsilon | NM_176891 | chr9_21461231-21461231_G_C | 155L>V | Substitution | Nonsynonymous coding | 48% | 38 | 314 |
| CGL 55 PT | OR6B2 | olfactory receptor, family 6, subfamily B, member 2 | CCDS46556.1 | chr2_240969483-240969483_G_A | 122R>C | Substitution | Nonsynonymous coding | 48% | 76 | 15 |
| CGL 55 PT | FAN1 | FANCD2/FANCI-associated nuclease 1 | CCDS32186.1 | chr15_31196959-31196959_T_G | 31I>M | Substitution | Nonsynonymous coding | 47% | 28 | 204 |
| CGL 55 PT | TTC28 | tetratricopeptide repeat domain 28 | CCDS46878.1 | chr22_28693825-28693825_G_C | 162T>S | Substitution | Nonsynonymous coding | 47% | 18 | 92 |
| CGL 55 PT | TTC3 | tetratricopeptide repeat domain 3 | CCDS13651.1 | chr21_38569135-38569135_G_C | 1793G>R | Substitution | Nonsynonymous coding | 47% | 81 | 188 |
| CGL 55 PT | APOL1 | apolipoprotein L, 1 | CCDS13925.1 | chr22_36661376-36661376_T_C | 181V>A | Substitution | Nonsynonymous coding | 47% | 69 | 344 |
| CGL 55 PT | ABP1 | amiloride binding protein 1 (amine oxidase (copper-containing)) | CCDS43679.1 | chr7_150555005-150555005_G_A | 483G>S | Substitution | Nonsynonymous coding | 47% | 86 | 270 |
| CGL 55 PT | CCDC107 | Coiled-coil domain-containing protein 107;CCDC107;ortholog | CCDS6583.1 | chr9_35660968-35660968_T_A | C212X | Substitution | stopgain | 47% | 24 | 63 |
| CGL 55 PT | RP11-46C24.3 | lncRNA | ENST00000376340 | chr16_89234740-89234740_C_T | 19R>C | Substitution | Nonsynonymous coding | 47% | 86 | 178 |
| CGL 55 PT | C9orf64 | chromosome 9 open reading frame 64 | CCDS6868.2 | chr9_86571379-86571379_A_G | 13F>L | Substitution | Nonsynonymous coding | 47% | 70 | 292 |
| CGL 55 PT | NLRP12 | NLR family, pyrin domain containing 12 | CCDS12864.1 | chr19_54310810-54310810_G_A | 728R>W | Substitution | Nonsynonymous coding | 47% | 62 | 246 |
| CGL 55 PT | LRP2 | low density lipoprotein receptor-related protein 2 | CCDS2232.1 | chr2_170009390-170009390_C_T | 4127R>H | Substitution | Nonsynonymous coding | 47% | 23 | 158 |
| CGL 55 PT | RP1 | retinitis pigmentosa 1 (autosomal dominant) | CCDS6180.1 | chr8_55539395-55539395_A_T | 985N>Y | Substitution | Nonsynonymous coding | 47% | 38 | 163 |
| CGL 55 PT | PTPN18 | protein tyrosine phosphatase, non-receptor type 18 (brain-derived) | CCDS2161.1 | chr2_131127695-131127695_G_T | 207M>I | Substitution | Nonsynonymous coding | 47% | 91 | 168 |
| CGL 55 PT | APBA1 | amyloid beta (A4) precursor protein-binding, family A, member 1 | CCDS6630.1 | chr9_72086584-72086584_T_C | 442T>A | Substitution | Nonsynonymous coding | 47% | 37 | 244 |
| CGL 55 PT | SH2B1 | SH2B adaptor protein 1 | CCDS32424.1 | chr16_28883241-28883241_A_G | 484T>A | Substitution | Nonsynonymous coding | 47% | 36 | 139 |

Fig. 8 (continued)

| | | | | | | | | | |
|---|---|---|---|---|---|---|---|---|---|
| CGLI 55 PT | SLC17A5 | solute carrier family 17 (anion/sugar transporter), member 5 | CCDS4981.1 | chr6_74320172-74320172_C_A | 404G>C | Substitution | Nonsynonymous coding | 47% | 36 | 138 |
| CGLI 55 PT | GTSE1 | G-2 and S-phase expressed 1 | CCDS14074.2 | chr22_46722517-46722517_C_T | 584R>C | Substitution | Nonsynonymous coding | 47% | 79 | 274 |
| CGLI 55 PT | MLN | motilin | CCDS4786.1 | chr6_33768867-33768867_G_C | 25A>G | Substitution | Nonsynonymous coding | 47% | 121 | 112 |
| CGLI 55 PT | GAD1 | glutamate decarboxylase 1 (brain, 67kDa) | ENST00000375273 | chr2_171705284-171705284_A_G | 404Y>C | Substitution | Nonsynonymous coding | 47% | 64 | 162 |
| CGLI 55 PT | PRUNE2 | prune homolog 2 (Drosophila) | CCDS47982.1 | chr9_79321904-79321904_G_C | 1762S>R | Substitution | Nonsynonymous coding | 47% | 47 | 232 |
| CGLI 55 PT | MAGEF1 | melanoma antigen family F, 1 | CCDS3269.1 | chr3_184429332-184429332_T_C | 93K>R | Substitution | Nonsynonymous coding | 47% | 134 | 847 |
| CGLI 55 PT | UHRF1BP1 | UHRF1 binding protein 1 | CCDS43455.1 | chr6_34791089-34791089_A_G | 101N>S | Substitution | Nonsynonymous coding | 47% | 40 | 114 |
| CGLI 55 PT | ZAN | zonadhesin | ENST00000419263 | chr7_100346012-100346012_G_C | 390G>R | Substitution | Nonsynonymous coding | 46% | 33 | 119 |
| CGLI 55 PT | DBF4B | DBF4 homolog B (S. cerevisiae) | CCDS11485.1 | chr17_42818710-42818710_T_G | 240F>L | Substitution | Nonsynonymous coding | 46% | 26 | 126 |
| CGLI 55 PT | DENND1C | DENN/MADD domain containing 1C | CCDS45936.1 | chr19_6475368-6475368_G_A | 324P>S | Substitution | Nonsynonymous coding | 46% | 160 | 219 |
| CGLI 55 PT | FGFR4 | fibroblast growth factor receptor 4 | CCDS4410.1 | chr5_176520503-176520503_G_T | 450V>L | Substitution | Nonsynonymous coding | 46% | 210 | 332 |
| CGLI 55 PT | PLSCR2 | phospholipid scramblase 2 | CCDS3134.1 | chr3_146167019-146167019_C_T | 207V>M | Substitution | Nonsynonymous coding | 46% | 19 | 186 |
| CGLI 55 PT | SEMA6B | Semaphorin-6B,SEMA6B;ortholog | CCDS12131.1 | chr19_4552639-4552639_G_A | R262C | Substitution | nonsynonymous SNV | 46% | 25 | 34 |
| CGLI 55 PT | ZFYVE20 | zinc finger, FYVE domain containing 20 | CCDS2623.1 | chr3_15118441-15118441_G_A | NA | Substitution | Splice site acceptor | 46% | 56 | 130 |
| CGLI 55 PT | NLRP12 | NACHT, LRR and PYD domains-containing protein 12,NLRP12;ortholog | CCDS12864.1 | chr19_54310810-54310810_G_A | R728W | Substitution | nonsynonymous SNV | 46% | 37 | 34 |
| CGLI 55 PT | SMIM2 | small integral membrane protein 2 | ENST00000400419 | chr13_44734772-44734772_C_T | 74A>T | Substitution | Nonsynonymous coding | 46% | 55 | 142 |
| CGLI 55 PT | TTC3 | E3 ubiquitin-protein ligase TTC3,TTC3;ortholog | CCDS13651.1 | chr21_38566106-38566106_G_C | G1793R | Substitution | nonsynonymous SNV | 46% | 42 | 63 |
| CGLI 55 PT | CAPN7 | calpain 7 | CCDS2624.1 | chr3_15253626-15253626_A_C | 40L>F | Substitution | Nonsynonymous coding | 46% | 6 | 55 |
| CGLI 55 PT | CCDC107 | coiled-coil domain containing 107 | CCDS6583.1 | chr9_35660966-35660966_T_A | 212C>X | Substitution | Nonsense | 46% | 54 | 137 |
| CGLI 55 PT | GBE1 | glucan (1,4-alpha-), branching enzyme 1 | NM_000158 | chr3_81695617-81695617_C_G | 236Q>H | Substitution | Nonsynonymous coding | 46% | 12 | 57 |
| CGLI 55 PT | RAPGEF5 | Rap guanine nucleotide exchange factor (GEF) 5 | NM_012294 | chr7_22190048-22190048_G_A | 468R>W | Substitution | Nonsynonymous coding | 46% | 23 | 59 |
| CGLI 55 PT | SI | sucrase-isomaltase (alpha-glucosidase) | CCDS3196.1 | chr3_164735825-164735825_C_T | 1168R>H | Substitution | Nonsynonymous coding | 46% | 23 | 132 |
| CGLI 55 PT | LATS2 | LATS, large tumor suppressor, homolog 2 (Drosophila) | CCDS9294.1 | chr13_21563350-21563350_G_C | 190P>R | Substitution | Nonsynonymous coding | 46% | 102 | 320 |
| CGLI 55 PT | LRP6 | low density lipoprotein receptor-related protein 6 | CCDS8647.1 | chr12_12279793-12279793_C_A | 1382V>F | Substitution | Nonsynonymous coding | 46% | 34 | 198 |
| CGLI 55 PT | ANKZF1 | ankyrin repeat and zinc finger domain containing 1 | CCDS42821.1 | chr2_220097286-220097286_G_A | 147E>K | Substitution | Nonsynonymous coding | 46% | 50 | 239 |
| CGLI 55 PT | MMP2 | matrix metallopeptidase 2 (gelatinase A, 72kDa gelatinase, 72kDa type IV collagenase) | CCDS10752.1 | chr16_55513515-55513515_G_T | 42A>S | Substitution | Nonsynonymous coding | 46% | 94 | 94 |
| CGLI 55 PT | ABO | ABO blood group (transferase A, alpha 1-3-N-acetylgalactosaminyltransferase; transferase B, alpha 1-3-galactosyltransferase) | ENST00000319876 | chr9_136131315-136131315_C_G | 287G>A | Substitution | Nonsynonymous coding | 46% | 125 | 368 |
| CGLI 55 PT | AP1S3 | adaptor-related protein complex 1, sigma 3 subunit | ENST00000444408 | chr2_224640804-224640804__AA | NA | Insertion | Frameshift | 46% | 36 | 264 |
| CGLI 55 PT | GIGYF2 | GRB10 interacting GYF protein 2 | CCDS46542.1 | chr2_233709083-233709083_C_G | 1056S>C | Substitution | Nonsynonymous coding | 46% | 81 | 195 |
| CGLI 55 PT | ZNF667 | zinc finger protein 667 | ENST00000342634 | chr19_56973777-56973777_G_A | 81A>V | Substitution | Nonsynonymous coding | 46% | 106 | 118 |
| CGLI 55 PT | GAMT | guanidinoacetate N-methyltransferase | CCDS12064.1 | chr19_1397443-1397443_G_A | 299T>M | Substitution | Nonsynonymous coding | 46% | 76 | 225 |
| CGLI 55 PT | ABO | ABO blood group (transferase A, alpha 1-3-N-acetylgalactosaminyltransferase; transferase B, alpha 1-3-galactosyltransferase) | ENST00000319879 | chr9_136131415-136131415_C_T | 234G>S | Substitution | Nonsynonymous coding | 45% | 131 | 329 |
| CGLI 55 PT | HEXIM2 | Protein HEXIM2,HEXIM2;ortholog | CCDS11496.1 | chr17_43246907-43246907_G_C | E198Q | Substitution | nonsynonymous SNV | 45% | 30 | 34 |
| CGLI 55 PT | FSTL4 | follistatin-like 4 | CCDS34236.1 | chr5_132552917-132552917_G_A | NA | Substitution | Splice site donor | 45% | 40 | 112 |
| CGLI 55 PT | TANGO6 | transport and golgi organization 6 homolog (Drosophila) | CCDS45516.1 | chr16_68943199-68943199_A_G | 823H>R | Substitution | Nonsynonymous coding | 45% | 30 | 89 |
| CGLI 55 PT | LRSAM1 | leucine rich repeat and sterile alpha motif containing 1 | CCDS6873.1 | chr9_130258350-130258350_A_T | 602Q>H | Substitution | Nonsynonymous coding | 45% | 49 | 77 |

Fig. 8 (continued)

| | | | | | | | | | |
|---|---|---|---|---|---|---|---|---|---|
| CGL1 55 PT | MYO15A | myosin XVA | CCDS42271.1 | chr17_18022821-18022821_A_G | 236Y>C | Substitution | Nonsynonymous coding | 45% | 189 | 449 |
| CGL1 55 PT | MAATS1 | MYCBP-associated, testis expressed 1 | CCDS2894.1 | chr3_119449081-119449081_G_T | 292R>L | Substitution | Nonsynonymous coding | 45% | 33 | 65 |
| CGL1 55 PT | CD68 | CD68 molecule | CCDS11114.1 | chr17_7484336-7484336_C_G | 295L>V | Substitution | Nonsynonymous coding | 45% | 193 | 250 |
| CGL1 55 PT | ANXA2R | annexin A2 receptor | CCDS34153.1 | chr5_43040115-43040115_C_G | 12A>P | Substitution | Nonsynonymous coding | 45% | 47 | 394 |
| CGL1 55 PT | ARID3C | AT rich interactive domain 3C (BRIGHT-like) | CCDS35006.1 | chr9_34621460-34621460_C_A | 412P>S | Substitution | Nonsynonymous coding | 45% | 14 | 63 |
| CGL1 55 PT | C11orf40 | Putative uncharacterized protein C11orf40;C11orf40;ortholog | CCDS31354.1 | chr11_4593488-4593489_AG_ | S115fs | Deletion | frameshift deletion | 45% | 23 | 34 |
| CGL1 55 PT | GAS6 | Growth arrest-specific protein 6;GAS6;ortholog | CCDS45074.1 | chr13_114526409-114526409_C_T | R232H | Substitution | nonsynonymous SNV | 45% | 41 | 63 |
| CGL1 55 PT | C9orf152 | chromosome 9 open reading frame 152 | CCDS35102.2 | chr9_112963307-112963307_G_T | 214A>D | Substitution | Nonsynonymous coding | 45% | 41 | 311 |
| CGL1 55 PT | ABCC6 | ATP-binding cassette, sub-family C (CFTR/MRP), member 6 | CCDS10568.1 | chr16_16278863-16278863_G_T | 932H>Q | Substitution | Nonsynonymous coding | 45% | 59 | 91 |
| CGL1 55 PT | HAPLN3 | hyaluronan and proteoglycan link protein 3 | CCDS10346.1 | chr15_89424870-89424870_G_T | 71R>S | Substitution | Nonsynonymous coding | 45% | 44 | 123 |
| CGL1 55 PT | ZP3 | zona pellucida glycoprotein 3 (sperm receptor) | CCDS47618.1 | chr7_76062783-76062783_T_A | NA | Substitution | Splice site acceptor | 45% | 35 | 162 |
| CGL1 55 PT | MRPS34 | mitochondrial ribosomal protein S34 | ENST00006177742 | chr16_1822539-1822539_C_T | NA | Substitution | Splice site acceptor | 45% | 104 | 742 |
| CGL1 55 PT | N4BP2 | NEDD4 binding protein 2 | CCDS3457.1 | chr4_40123540-40123540_T_C | 1270V>A | Substitution | Nonsynonymous coding | 45% | 13 | 105 |
| CGL1 55 PT | CAPN7 | Calpain-7;CAPN7;ortholog | CCDS2624.1 | chr3_15253628-15253628_A_C | L40F | Substitution | nonsynonymous SNV | 45% | 13 | 63 |
| CGL1 55 PT | SLC17A5 | Sialin;SLC17A5;ortholog | CCDS4981.1 | chr6_74320172-74320172_C_A | G404C | Substitution | nonsynonymous SNV | 45% | 43 | 34 |
| CGL1 55 PT | DSP | desmoplakin | CCDS4501.1 | chr6_7581384-7581384_T_C | I654L>P | Substitution | Nonsynonymous coding | 45% | 76 | 163 |
| CGL1 55 PT | TAAR9 | trace amine associated receptor 9 (gene/pseudogene) | NM_175057 | chr6_132859701-132859701_G_ | NA | Deletion | Frameshift | 45% | 59 | 470 |
| CGL1 55 PT | AOC1 | tRNA | CCDS43679.1 | chr7_150555005-150555005_G_A | G483S | Substitution | nonsynonymous SNV | 45% | 42 | 63 |
| CGL1 55 PT | SCN1B | sodium channel, voltage-gated, type I, beta subunit | CCDS46047.1 | chr19_35524688-35524688_G_A | 165A>T | Substitution | Nonsynonymous coding | 45% | 130 | 305 |
| CGL1 55 PT | RARRES2 | retinoic acid receptor responder (tazarotene induced) 2 | CCDS5902.1 | chr7_150035721-150035721_C_T | 162R>H | Substitution | Nonsynonymous coding | 45% | 54 | 199 |
| CGL1 55 PT | MIR611 | microRNA 611 | hsa-mir-611 | chr11_61560021-61560021_C_A | NA | Substitution | NA | 45% | 112 | 162 |
| CGL1 55 PT | STAC | SH3 and cysteine-rich domain-containing protein;STAC;ortholog | CCDS2662.1 | chr3_36526512-36526512_A_G | H178R | Substitution | nonsynonymous SNV | 45% | 33 | 63 |
| CGL1 55 PT | NOD2 | nucleotide-binding oligomerization domain containing 2 | CCDS10746.1 | chr16_50746154-50746154_G_A | 778E>K | Substitution | Nonsynonymous coding | 45% | 70 | 222 |
| CGL1 55 PT | LRRC4B | leucine rich repeat containing 4B | CCDS42595.1 | chr19_51022602-51022602_C_T | 123R>H | Substitution | Nonsynonymous coding | 44% | 137 | 112 |
| CGL1 55 PT | TMEM67 | transmembrane protein 67 | CCDS6258.2 | chr8_94768069-94768070_TT_ | NA | Deletion | Frameshift | 44% | 4 | 62 |
| CGL1 55 PT | NWD1 | NACHT and WD repeat domain containing 1 | ENST00000438489 | chr19_16855374-16855374_C_T | 114A>V | Substitution | Nonsynonymous coding | 44% | 100 | 261 |
| CGL1 55 PT | MAPK12 | mitogen-activated protein kinase 12 | CCDS14089.1 | chr22_50695397-50695397_C_G | NA | Substitution | Splice site acceptor | 44% | 83 | 315 |
| CGL1 55 PT | ADA | adenosine deaminase | CCDS13335.1 | chr20_43255220-43255220_T_C | 80K>R | Substitution | Nonsynonymous coding | 44% | 27 | 100 |
| CGL1 55 PT | BTBD3 | BTB (POZ) domain containing 3 | CCDS13113.1 | chr20_11903461-11903461_A_T | 239D>V | Substitution | Nonsynonymous coding | 44% | 54 | 113 |
| CGL1 55 PT | CDK5RAP1 | CDK5 regulatory subunit-associated protein 1;CDK5RAP1;ortholog | CCDS63255.1 | chr20_31958393-31958393_T_C | E358G | Substitution | nonsynonymous SNV | 44% | 27 | 63 |
| CGL1 55 PT | BSN | Protein bassoon;BSN;ortholog | CCDS2800.1 | chr3_49689585-49689585_G_A | G868R | Substitution | nonsynonymous SNV | 44% | 54 | 34 |
| CGL1 55 PT | ELL3 | RNA polymerase II elongation factor ELL3;ELL3;ortholog | CCDS10102.1 | chr15_44067975-44067975_G_A | T143I | Substitution | nonsynonymous SNV | 44% | 46 | 34 |
| CGL1 55 PT | LOXL1 | lysyl oxidase-like 1 | CCDS10253.1 | chr15_74219546-74219546_G_T | 141R>L | Substitution | Nonsynonymous coding | 44% | 42 | 264 |
| CGL1 55 PT | SLC38A10 | solute carrier family 38, member 10 | CCDS42397.1 | chr17_79244731-79244731_G_A | 373A>V | Substitution | Nonsynonymous coding | 44% | 42 | 44 |
| CGL1 55 PT | KDM6B | lysine (K)-specific demethylase 6B | CCDS32552.1 | chr17_7751531-7751531_C_T | 642P>L | Substitution | Nonsynonymous coding | 44% | 61 | 302 |
| CGL1 55 PT | TULP1 | tubby like protein 1 | CCDS4907.1 | chr6_35477032-35477032_A_G | 259I>T | Substitution | Nonsynonymous coding | 44% | 53 | 224 |
| CGL1 55 PT | PTPN18 | Tyrosine-protein phosphatase non-receptor type 18;PTPN18;ortholog | CCDS46410.1 | chr2_131127695-131127695_G_T | M100I | Substitution | nonsynonymous SNV | 44% | 34 | 63 |
| CGL1 55 PT | NCAN | neurocan | CCDS12397.1 | chr19_19337469-19337469_C_A | 418T>N | Substitution | Nonsynonymous coding | 44% | 83 | 239 |
| CGL1 55 PT | CADPS2 | Ca++-dependent secretion activator 2 | CCDS47891.1 | chr7_122114544-122114544_A_G | 627M>T | Substitution | Nonsynonymous coding | 44% | 15 | 43 |
| CGL1 55 PT | ADAM23 | ADAM metallopeptidase domain 23 | CCDS52389.1 | chr2_207345985-207345985_G_T | 154Q>H | Substitution | Nonsynonymous coding | 44% | 26 | 92 |

Fig. 8 (continued)

| | | | | | | | | | |
|---|---|---|---|---|---|---|---|---|---|
| CGLI 55 PT | CYP1A1 | cytochrome P450, family 1, subfamily A, polypeptide 1 | CCDS10268.1 | chr15_75015123-75015123_G_ | NA | Deletion | Frameshift | 44% | 78 | 249 |
| CGLI 55 PT | CELSR3 | cadherin, EGF LAG seven-pass G-type receptor 3 (flamingo homolog, Drosophila) | CCDS43087.1 | chr3_48667381-48667381_T_G | 485I>L | Substitution | Nonsynonymous coding | 44% | 89 | 174 |
| CGLI 55 PT | TUSC1 | tumor suppressor candidate 1 | CCDS34999.1 | chr9_25677696-25677696_A_C | 208S>A | Substitution | Nonsynonymous coding | 44% | 37 | 83 |
| CGLI 55 PT | BCAM | basal cell adhesion molecule (Lutheran blood group) | CCDS12644.1 | chr19_45322744-45322744_A_G | 539T>A | Substitution | Nonsynonymous coding | 44% | 143 | 179 |
| CGLI 55 PT | PROM1 | prominin 1 | CCDS47029.1 | chr4_15982164-15982164__G | NA | Insertion | Splice site acceptor | 44% | 11 | 119 |
| CGLI 55 PT | SLC12A9 | solute carrier family 12 (potassium/chloride transporters), member 9 | CCDS5797.1 | chr7_100454513-100454513_C_T | 158R>W | Substitution | Nonsynonymous coding | 44% | 77 | 208 |
| CGLI 55 PT | KRT3 | keratin 3 | CCDS44895.1 | chr12_53184620-53184620__A | NA | Insertion | Splice site donor | 44% | 40 | 160 |
| CGLI 55 PT | PEX6 | peroxisomal biogenesis factor 6 | CCDS4877.1 | chr6_42933464-42933464_G_A | 809A>V | Substitution | Nonsynonymous coding | 44% | 87 | 317 |
| CGLI 55 PT | SLC4A2 | Anion exchange protein 2;SLC4A2;ortholog | CCDS56520.1 | chr7_150773112-150773112_C_T | R1153C | Substitution | nonsynonymous SNV | 44% | 47 | 63 |
| CGLI 55 PT | CABP4 | calcium binding protein 4 | CCDS8166.1 | chr11_67223850-67223850_A_G | 160T>A | Substitution | Nonsynonymous coding | 44% | 97 | 256 |
| CGLI 55 PT | TRIM32 | tripartite motif containing 32 | CCDS6817.1 | chr9_119461951-119461951_A_G | 644S>G | Substitution | Nonsynonymous coding | 44% | 43 | 142 |
| CGLI 55 PT | DCTN1 | dynactin 1 | CCDS1939.1 | chr2_74598840-74598840_T_C | 157S>G | Substitution | Nonsynonymous coding | 44% | 25 | 36 |
| CGLI 55 PT | LYRM4 | LYR motif containing 4 | NM_020408 | chr6_5109716-5109716_C_T | 73G>S | Substitution | Nonsynonymous coding | 44% | 32 | 20 |
| CGLI 55 PT | SYTL2 | synaptotagmin-like 2 | CCDS31649.1 | chr11_85468708-85468708_G_A | 21R>W | Substitution | Nonsynonymous coding | 44% | 32 | 82 |
| CGLI 55 PT | MLH1 | DNA mismatch repair protein Mlh1;MLH1;ortholog | CCDS2663.1 | chr3_37035130-37035130_C_G | A31S | Substitution | nonsynonymous SNV | 44% | 39 | 83 |
| CGLI 55 PT | SLC22A4 | solute carrier family 22 (organic cation/ergothioneine transporter), member 4 | CCDS4153.1 | chr5_131676320-131676320_C_T | 503L>F | Substitution | Nonsynonymous coding | 44% | 46 | 82 |
| CGLI 55 PT | STX16 | syntaxin 16 | CCDS13468.1 | chr20_57244409-57244409_G_T | 152E>D | Substitution | Nonsynonymous coding | 44% | 35 | 142 |
| CGLI 55 PT | TMPRSS11E | transmembrane protease, serine 11E | CCDS33993.1 | chr4_69332450-69332450_A_G | 80S>G | Substitution | Nonsynonymous coding | 44% | 7 | 246 |
| CGLI 55 PT | OR1J2 | olfactory receptor, family 1, subfamily J, member 2 | CCDS35121.1 | chr9_125273386-125273386__T | NA | Insertion | Frameshift | 44% | 38 | 649 |
| CGLI 55 PT | SIL1 | SIL1 homolog, endoplasmic reticulum chaperone (S. cerevisiae) | CCDS4209.1 | chr5_138456753-138456753_G_A | 72P>L | Substitution | Nonsynonymous coding | 44% | 31 | 58 |
| CGLI 55 PT | ZNF610 | Zinc finger protein 610;ZNF610;ortholog | CCDS54309.1 | chr19_52869721-52869721_A_G | I321V | Substitution | nonsynonymous SNV | 44% | 31 | 34 |
| CGLI 55 PT | MFAP1 | Microfibrillar-associated protein 1;MFAP1;ortholog | CCDS10105.1 | chr15_44102984-44102984_G_A | R308C | Substitution | nonsynonymous SNV | 44% | 51 | 34 |
| CGLI 55 PT | CDAN1 | codanin 1 | CCDS32209.1 | chr15_43023482-43023482_T_C | 596Q>R | Substitution | Nonsynonymous coding | 44% | 51 | 225 |
| CGLI 55 PT | WWC2 | WW and C2 domain containing 2 | CCDS34109.2 | chr4_184114748-184114748_G_A | NA | Substitution | Splice site acceptor | 44% | 17 | 126 |
| CGLI 55 PT | ITGB5 | integrin, beta 5 | CCDS3030.1 | chr3_124592303-124592303_C_T | 49C>Y | Substitution | Nonsynonymous coding | 43% | 20 | 81 |
| CGLI 55 PT | OR5P2 | olfactory receptor, family 5, subfamily P, member 2 | CCDS7782.1 | chr11_7818387-7818387_G_T | 35L>I | Substitution | Nonsynonymous coding | 43% | 10 | 49 |
| CGLI 55 PT | RTFDC1 | replication termination factor 2 domain containing 1 | CCDS13453.1 | chr20_56088381-56088381_C_T | 193A>V | Substitution | Nonsynonymous coding | 43% | 30 | 119 |
| CGLI 55 PT | DTX3L | E3 ubiquitin-protein ligase DTX3L;DTX3L;ortholog | CCDS3015.1 | chr3_122284745-122284747_TTG_ | 76_77del | Deletion | nonframeshift deletion | 43% | 30 | 83 |
| CGLI 55 PT | ANXA2R | Annexin-2 receptor;ANXA2R;ortholog | CCDS34193.1 | chr5_43040115-43040115_C_G | A12P | Substitution | nonsynonymous SNV | 43% | 23 | 34 |
| CGLI 55 PT | KANK2 | KN motif and ankyrin repeat domains 2 | CCDS12255.1 | chr19_11303830-11303830_C_T | 309R>Q | Substitution | Nonsynonymous coding | 43% | 85 | 120 |
| CGLI 55 PT | C9orf43 | chromosome 9 open reading frame 43 | CCDS6796.1 | chr9_116186582-116186582_C_T | 285R>C | Substitution | Nonsynonymous coding | 43% | 29 | 141 |
| CGLI 55 PT | SQRDL | sulfide quinone reductase-like (yeast) | CCDS10127.1 | chr15_45951224-45951224_G_A | 35G>R | Substitution | Nonsynonymous coding | 43% | 19 | 153 |
| CGLI 55 PT | ERAP2 | endoplasmic reticulum aminopeptidase 2 | CCDS4086.1 | chr5_96222432-96222433_TT_ | NA | Deletion | Frameshift | 43% | 22 | 122 |
| CGLI 55 PT | SMPD2 | sphingomyelin phosphodiesterase 2, neutral membrane (neutral sphingomyelinase) | ENST00000458497 | chr6_109763948-109763948_C_ | NA | Deletion | Frameshift | 43% | 103 | 420 |
| CGLI 55 PT | LANCL2 | LanC-like protein 2;LANCL2;ortholog | CCDS55517.1 | chr7_55496118-55496118_G_G | D412E | Substitution | nonsynonymous SNV | 43% | 28 | 34 |
| CGLI 55 PT | MYO7B | myosin VIIB | CCDS46405.1 | chr2_128393336-128393336_C_T | 1928R>W | Substitution | Nonsynonymous coding | 43% | 84 | 216 |
| CGLI 55 PT | OR6C4 | olfactory receptor, family 6, subfamily C, member 4 | CCDS31827.1 | chr12_55945662-55945662_T_C | 218Y>H | Substitution | Nonsynonymous coding | 43% | 31 | 297 |

Fig. 8 (continued)

| | | | | | | | | | |
|---|---|---|---|---|---|---|---|---|---|
| CGLI 55 PT | GRIN3B | glutamate receptor, ionotropic, N-methyl-D-aspartate 3B | CCDS32861.1 | chr19_1004897-1004897__CGTT | NA | Insertion | Frameshift | 43% | 115 | 305 |
| CGLI 55 PT | C2orf71 | chromosome 2 open reading frame 71 | CCDS42669.1 | chr2_29287927-29287927__GCT | NA | Insertion | in-frame insertion | 43% | 57 | 71 |
| CGLI 55 PT | UNC13A | unc-13 homolog A (C. elegans) | CCDS46013.1 | chr19_17738409-17738411_AAG__ | NA | Deletion | Splice site acceptor | 43% | 51 | 199 |
| CGLI 55 PT | CDPF1 | cysteine-rich, DPF motif domain containing 1 | CCDS33670.1 | chr22_46641077-46641077_T_C | 95N>S | Substitution | Nonsynonymous coding | 43% | 75 | 519 |
| CGLI 55 PT | HSPA4L | heat shock 70kDa protein 4-like | CCDS3734.1 | chr4_128743978-128743978_G_A | 623A>T | Substitution | Nonsynonymous coding | 43% | 6 | 33 |
| CGLI 55 PT | MOGAT1 | monoacylglycerol O-acyltransferase 1 | CCDS46524.1 | chr2_223559875-223559875_G_A | 241G>R | Substitution | Nonsynonymous coding | 43% | 33 | 32 |
| CGLI 55 PT | PAICS | phosphoribosylaminoimidazole carboxylase, phosphoribosylaminoimidazole succinocarboxamide synthetase | CCDS47060.1 | chr4_57307916-57307916_C_T | 36S>F | Substitution | Nonsynonymous coding | 43% | 15 | 31 |
| CGLI 55 PT | PNKP | polynucleotide kinase 3'-phosphatase | CCDS12763.1 | chr19_50364891-50364891_G_T | 454L>M | Substitution | Nonsynonymous coding | 43% | 9 | 59 |
| CGLI 55 PT | TPBG | trophoblast glycoprotein | CCDS4995.1 | chr6_83075442-83075442_G_A | 255R>H | Substitution | Nonsynonymous coding | 43% | 87 | 389 |
| CGLI 55 PT | ZC3H12C | zinc finger CCCH-type containing 12C | CCDS44727.1 | chr11_110035467-110035467_C_G | 553Q>E | Substitution | Nonsynonymous coding | 43% | 111 | 204 |
| CGLI 55 PT | SPATS2L | spermatogenesis associated, serine-rich 2-like | CCDS46483.1 | chr2_201303950-201303950_C_A | 184P>H | Substitution | Nonsynonymous coding | 43% | 32 | 205 |
| CGLI 55 PT | CASP8 | caspase 8, apoptosis-related cysteine peptidase | CCDS42798.1 | chr2_202149589-202149589_G_C | 344D>H | Substitution | Nonsynonymous coding | 43% | 57 | 317 |
| CGLI 55 PT | MAN2A2 | mannosidase, alpha, class 2A, member 2 | CCDS32332.1 | chr15_91456592-91456592_A_G | 892I>V | Substitution | Nonsynonymous coding | 43% | 37 | 255 |
| CGLI 55 PT | FAM98C | family with sequence similarity 98, member C | CCDS42562.1 | chr19_38899502-38899502__AAG | NA | Insertion | in-frame insertion | 43% | 17 | 90 |
| CGLI 55 PT | JAK3 | Janus kinase 3 | CCDS12366.1 | chr19_17945896-17945896_C_T | 722V>I | Substitution | Nonsynonymous coding | 42% | 79 | 231 |
| CGLI 55 PT | DBNDD1 | Dysbindin domain-containing protein 1;DBNDD1;ortholog | CCDS10991.2 | chr16_90075243-90075243_C_T | E110K | Substitution | nonsynonymous SNV | 42% | 14 | 34 |
| CGLI 55 PT | THOC5 | THO complex subunit 5 homolog;THOC5;ortholog | CCDS13859.1 | chr22_29945063-29945063_C_T | R25Q | Substitution | nonsynonymous SNV | 42% | 30 | 63 |
| CGLI 55 PT | MLH1 | DNA mismatch repair protein Mlh1;MLH1;ortholog | CCDS2663.1 | chr3_37035129-37035129_G_T | A31S | Substitution | nonsynonymous SNV | 42% | 36 | 83 |
| CGLI 55 PT | LRSAM1 | E3 ubiquitin-protein ligase LRSAM1;LRSAM1;ortholog | CCDS55347.1 | chr9_130258350-130258350_A_T | Q575H | Substitution | nonsynonymous SNV | 42% | 27 | 63 |
| CGLI 55 PT | RIMS2 | Regulating synaptic membrane exocytosis protein 2;RIMS2;ortholog | CCDS64948.1 | chr8_105025770-105025770_C_T | R868C | Substitution | nonsynonymous SNV | 42% | 43 | 83 |
| CGLI 55 PT | ADAMTS13 | ADAM metallopeptidase with thrombospondin type 1 motif, 13 | CCDS56970.1 | chr9_136301982-136301982_C_G | 448Q>E | Substitution | Nonsynonymous coding | 42% | 32 | 148 |
| CGLI 55 PT | ITGB6 | Integrin beta-6;ITGB6;ortholog | CCDS2212.1 | chr2_160993992-160993992_T_C | Q538R | Substitution | nonsynonymous SNV | 42% | 32 | 83 |
| CGLI 55 PT | GDF6 | Growth/differentiation factor 6;GDF6;ortholog | CCDS34926.1 | chr8_97172732-97172732_C_G | E63D | Substitution | nonsynonymous SNV | 42% | 37 | 34 |
| CGLI 55 PT | USP1 | upstream binding protein 1 (LBP-1a) | CCDS2659.1 | chr3_33453135-33453135_T_C | 165S>G | Substitution | Nonsynonymous coding | 42% | 42 | 81 |
| CGLI 55 PT | RIMS2 | regulating synaptic membrane exocytosis 2 | CCDS40761.1 | chr8_105025770-105025770_C_T | 863R>C | Substitution | Nonsynonymous coding | 42% | 47 | 156 |
| CGLI 55 PT | PLXNB2 | plexin B2 | CCDS43035.1 | chr22_50716644-50716644_C_T | 1597E>K | Substitution | Nonsynonymous coding | 42% | 117 | 263 |
| CGLI 55 PT | UGDH | UDP-glucose 6-dehydrogenase | CCDS3455.1 | chr4_39511531-39511531__A | NA | Insertion | Splice site acceptor | 42% | 13 | 184 |
| CGLI 55 PT | MZF1 | Myeloid zinc finger 1;MZF1;ortholog | CCDS12986.1 | chr19_59074226-59074226__G | P473fs | Insertion | frameshift insertion | 42% | 13 | 34 |
| CGLI 55 PT | KCNJ16 | potassium inwardly-rectifying channel, subfamily J, member 16 | CCDS11687.1 | chr17_68128332-68128332_G_A | 35R>Q | Substitution | Nonsynonymous coding | 42% | 70 | 377 |
| CGLI 55 PT | KLKB1 | kallikrein B, plasma (Fletcher factor) 1 | CCDS34120.1 | chr4_187158034-187158034_G_A | 143S>N | Substitution | Nonsynonymous coding | 42% | 31 | 155 |
| CGLI 55 PT | BIN3 | bridging integrator 3 | CCDS47825.1 | chr8_22481483-22481483_T_C | 187Y>C | Substitution | Nonsynonymous coding | 42% | 36 | 110 |
| CGLI 55 PT | LINC00577 | long intergenic non-protein coding RNA 577 | ENST00000436382 | chr6_105388263-105388264_GA__ | NA | Deletion | NA | 42% | 55 | 59 |
| CGLI 55 PT | FAN1 | Fanconi-associated nuclease 1;FAN1;ortholog | CCDS32186.1 | chr15_31196959-31196959_T_G | I31M | Substitution | nonsynonymous SNV | 42% | 20 | 83 |
| CGLI 55 PT | PSMD3 | 26S proteasome non-ATPase regulatory subunit 3;PSMD3;ortholog | CCDS11356.1 | chr17_38151742-38151742_T_G | L428V | Substitution | nonsynonymous SNV | 42% | 45 | 63 |
| CGLI 55 PT | MC1R | melanocortin 1 receptor (alpha melanocyte stimulating hormone receptor) | NM_002386 | chr16_89986469-89986469_C_G | 268P>R | Substitution | Nonsynonymous coding | 42% | 289 | 796 |

Fig. 8 (continued)

| | | | | | | | | | | |
|---|---|---|---|---|---|---|---|---|---|---|
| CGL1 55 PT | SGPP2 | sphingosine-1-phosphate phosphatase 2 | CCDS2453.1 | chr2_223423283-223423283_T_C | 269I>T | Substitution | Nonsynonymous coding | 42% | 72 | 719 |
| CGL1 55 PT | OR6C4 | Olfactory receptor 6C4;OR6C4;ortholog | CCDS31827.1 | chr12_55945682-55945682_T_C | Y218H | Substitution | nonsynonymous SNV | 42% | 32 | 34 |
| CGL1 55 PT | AC087289.1 | Uncharacterized protein; cDNA FLJ40144 fis, clone TESTI2013012 | ENST00000326348 | chr17_73817670-73817670_G_ | NA | Deletion | Frameshift | 41% | 73 | 313 |
| CGL1 55 PT | R3HDM1 | R3H domain containing 1 | CCDS2177.1 | chr2_136418898-136418898_C_T | 661P>L | Substitution | Nonsynonymous coding | 41% | 60 | 255 |
| CGL1 55 PT | PEAR1 | Platelet endothelial aggregation receptor 1;PEAR1;ortholog | CCDS30892.1 | chr1_156876818-156876818_C_T | P197L | Substitution | Nonsynonymous SNV | 41% | 52 | 83 |
| CGL1 55 PT | CILP2 | cartilage intermediate layer protein 2 | CCDS12405.1 | chr19_19651058-19651058_G_A | 70G>D | Substitution | Nonsynonymous coding | 41% | 66 | 335 |
| CGL1 55 PT | AGAP1 | ArfGAP with GTPase domain, ankyrin repeat and PH domain 1 | ENST00000409457 | chr2_236761415-236761415__CAGG | NA | Insertion | Frameshift | 41% | 47 | 218 |
| CGL1 55 PT | XYLB | Xylulose kinase;XYLB;ortholog | CCDS2678.1 | chr3_38407109-38407109_C_T | S130F | Substitution | nonsynonymous SNV | 41% | 37 | 63 |
| CGL1 55 PT | MKS1 | Meckel syndrome, type 1 | CCDS11603.2 | chr17_56293498-56293498_C_T | 123R>Q | Substitution | Nonsynonymous coding | 41% | 23 | 177 |
| CGL1 55 PT | MLL | myeloid/lymphoid or mixed-lineage leukemia (trithorax homolog, Drosophila) | CCDS31686.1 | chr11_118344275-118344275_C_T | 901H>Y | Substitution | Nonsynonymous coding | 41% | 46 | 827 |
| CGL1 55 PT | SHANK1 | SH3 and multiple ankyrin repeat domains protein 1;SHANK1;ortholog | CCDS12799.1 | chr19_51170685-51170685_G_A | P1511L | Substitution | nonsynonymous SNV | 41% | 16 | 34 |
| CGL1 55 PT | C21orf2 | Protein C21orf2;C21orf2;ortholog | CCDS13709.1 | chr21_45752951-45752951_C_T | R113H | Substitution | nonsynonymous SNV | 41% | 16 | 34 |
| CGL1 55 PT | B3GAT3 | beta-1,3-glucuronyltransferase 3 (glucuronosyltransferase I) | CCDS8025.1 | chr11_62384779-62384779_TCAG_ | NA | Deletion | Frameshift | 41% | 115 | 158 |
| CGL1 55 PT | MCHR2 | melanin-concentrating hormone receptor 2 | CCDS5044.1 | chr6_100390984-100390984_C_T | 143R>H | Substitution | Nonsynonymous coding | 41% | 27 | 47 |
| CGL1 55 PT | NACC2 | NACC family member 2, BEN and BTB (POZ) domain containing | CCDS6993.1 | chr9_138908135-138908135_C_T | 343G>R | Substitution | Nonsynonymous coding | 41% | 9 | 24 |
| CGL1 55 PT | TANGO6 | transport and golgi organization 6 homolog (Drosophila) | CCDS45516.1 | chr16_68909192-68909192_A_C | 377Q>P | Substitution | Nonsynonymous coding | 41% | 9 | 91 |
| CGL1 55 PT | EDN1 | endothelin 1 | CCDS4522.1 | chr6_12296255-12296255_G_T | 198K>N | Substitution | Nonsynonymous coding | 41% | 47 | 277 |
| CGL1 55 PT | DNAH11 | dynein, axonemal, heavy chain 11 | ENST00000328843 | chr7_21730477-21730477_G_A | 2014E>K | Substitution | Nonsynonymous coding | 41% | 31 | 130 |
| CGL1 55 PT | C9orf84 | UPF0565 protein C9orf84;C9orf84;ortholog | CCDS6686.2 | chr9_86571379-86571379_A_G | F13L | Substitution | nonsynonymous SNV | 41% | 33 | 34 |
| CGL1 55 PT | KCNN2 | potassium intermediate/small conductance calcium-activated channel, subfamily N, member 2 | CCDS54114.1 | chr5_113698632-113698632__GCC | NA | Insertion | In-frame insertion | 41% | 46 | 291 |
| CGL1 55 PT | GBA2 | Non-lysosomal glucosylceramidase;GBA2;ortholog | CCDS6589.1 | chr9_35748379-35748379_A_C | L108R | Substitution | nonsynonymous SNV | 41% | 24 | 63 |
| CGL1 55 PT | TTC3 | tetratricopeptide repeat domain 3 | CCDS13651.1 | chr21_38570287-38570287_G_T | 1931V>F | Substitution | Nonsynonymous coding | 41% | 39 | 72 |
| CGL1 55 PT | TRMU | tRNA 5-methylaminomethyl-2-thiouridylate methyltransferase | CCDS14075.1 | chr22_46731689-46731689_G_T | 10A>S | Substitution | Nonsynonymous coding | 41% | 41 | 58 |
| CGL1 55 PT | SARDH | Sarcosine dehydrogenase, mitochondrial;SARDH;ortholog | NULL | chr9_136578159-136578159_C_A | splicing | Substitution | NULL | 41% | 28 | 83 |
| CGL1 55 PT | SPATC1L | spermatogenesis and centriole associated 1-like | CCDS46953.1 | chr21_47588266-47588266_C_A | 187S>I | Substitution | Nonsynonymous coding | 41% | 84 | 168 |
| CGL1 55 PT | TTN | titin | NM_133379 | chr2_179613119-179613119_C_G | 4670V>L | Substitution | Nonsynonymous coding | 41% | 15 | 322 |
| CGL1 55 PT | MYO15A | Unconventional myosin-XV;MYO15A;ortholog | CCDS42271.1 | chr17_18022821-18022821_A_G | Y236C | Substitution | nonsynonymous SNV | 40% | 74 | 83 |
| CGL1 55 PT | OR4S2 | Olfactory receptor 4S2;OR4S2;ortholog | CCDS31505.1 | chr11_55418453-55418453_G_C | C25S | Substitution | Substitution | 40% | 19 | 34 |
| CGL1 55 PT | CDKN1A | cyclin-dependent kinase inhibitor 1A (p21, Cip1) | CCDS4824.1 | chr6_36651971-36651971_C_A | 31S>R | Substitution | Nonsynonymous coding | 40% | 97 | 130 |
| CGL1 55 PT | DBNDD1 | dysbindin (dystrobrevin binding protein 1) domain containing 1 | CCDS10991.2 | chr16_90075243-90075243_C_T | 110E>K | Substitution | Nonsynonymous coding | 40% | 23 | 33 |
| CGL1 55 PT | ABCG8 | ATP-binding cassette, sub-family G (WHITE), member 8 | CCDS1815.1 | chr2_44101597-44101597_C_A | 488T>N | Substitution | Nonsynonymous coding | 40% | 27 | 218 |
| CGL1 55 PT | C3 | Complement C3;C3;ortholog | CCDS32883.1 | chr19_6693022-6693022_G_T | C1101X | Substitution | stopgain | 40% | 35 | 34 |
| CGL1 55 PT | RECQL4 | RecQ protein-like 4 | ENST00000428558 | chr8_145739380-145739380_G_A | 664L>F | Substitution | Nonsynonymous coding | 40% | 43 | 130 |
| CGL1 55 PT | MMP2 | 72 kDa type IV collagenase;MMP2;ortholog | CCDS10752.1 | chr16_55513515-55513515_G_T | A42S | Substitution | nonsynonymous SNV | 40% | 57 | 34 |
| CGL1 55 PT | USH1C | Usher syndrome 1C (autosomal recessive, severe) | CCDS7825.1 | chr11_17519742-17519742_C_G | 819E>D | Substitution | Nonsynonymous coding | 40% | 142 | 332 |

Fig. 8 (continued)

| | | | | | | | | | | |
|---|---|---|---|---|---|---|---|---|---|---|
| CGLI 55 PT | HOXC13 | Homeobox protein Hox-C13;HOXC13;ortholog | CCDS8865.1 | chr2_54332734-54332734__TTA | L15delinsLY | Insertion | nonframeshift insertion | 40% | 10 | 34 |
| CGLI 55 PT | NGLY1 | N-glycanase 1 | CCDS33719.1 | chr3_25824865-25824865_A_G | 6L>S | Substitution | Nonsynonymous coding | 40% | 6 | 31 |
| CGLI 55 PT | PSORS1C1 | Psoriasis susceptibility 1 candidate gene 1 protein;PSORS1C1;ortholog | CCDS34390.1 | chr6_31106501-31106501__C | P38fs | Insertion | frameshift insertion | 40% | 47 | 63 |
| CGLI 55 PT | C3 | complement component 3 | CCDS32883.1 | chr19_6718387-6718387_G_C | 102R>G | Substitution | Nonsynonymous coding | 40% | 68 | 271 |
| CGLI 55 PT | UAP1L1 | UDP-N-acetylglucosamine pyrophosphorylase 1-like 1 | CCDS7028.2 | chr9_139975229-139975229_G_A | 423A>T | Substitution | Nonsynonymous coding | 40% | 64 | 94 |
| CGLI 55 PT | UNC80 | unc-80 homolog (C. elegans) | CCDS46504.1 | chr2_210804245-210804245_C_G | 2106S>C | Substitution | Nonsynonymous coding | 40% | 29 | 147 |
| CGLI 55 PT | C6orf123 | chromosome 6 open reading frame 123 | ENST00000340619 | chr6_168191698-168191698_G_A | 20A>V | Substitution | Nonsynonymous coding | 40% | 36 | 214 |
| CGLI 55 PT | ABI3BP | ABI family, member 3 (NESH) binding protein | ENST00000398284 | chr3_100583652-100583652_A_ | NA | Deletion | Splice site acceptor | 40% | 17 | 28 |
| CGLI 55 PT | EPHX1 | epoxide hydrolase 1, microsomal (xenobiotic) | CCDS1547.1 | chr1_226019633-226019633_T_C | 113Y>H | Substitution | Nonsynonymous coding | 40% | 32 | 192 |
| CGLI 55 PT | HIST1H3C | histone cluster 1, H3c | CCDS4578.1 | chr6_26045721-26045721_A_T | 28K>M | Substitution | Nonsynonymous coding | 40% | 64 | 164 |
| CGLI 55 PT | PMS2 | PMS2 postmeiotic segregation increased 2 (S. cerevisiae) | CCDS5343.1 | chr7_6026708-6026708_C_A | 563R>L | Substitution | Nonsynonymous coding | 40% | 32 | 425 |
| CGLI 55 PT | HHATL | hedgehog acyltransferase-like | CCDS2704.1 | chr3_42739670-42739672_GAA__ | NA | Deletion | in-frame deletion | 39% | 47 | 39 |
| CGLI 55 PT | LRRC4B | Leucine-rich repeat-containing protein 4B;LRRC4B;ortholog | CCDS42595.1 | chr19_51022602-51022602_C_T | R123H | Substitution | nonsynonymous SNV | 39% | 58 | 34 |
| CGLI 55 PT | PLA2R1 | phospholipase A2 receptor 1, 180kDa | CCDS33369.1 | chr2_160833821-160833821_C_T | 792R>H | Substitution | Nonsynonymous coding | 39% | 11 | 84 |
| CGLI 55 PT | TYR | tyrosinase | CCDS8284.1 | chr11_88911696-88911696_C_A | 192S>Y | Substitution | Nonsynonymous coding | 39% | 75 | 509 |
| CGLI 55 PT | RASSF8 | Ras association domain-containing protein 8;RASSF8;ortholog | CCDS53765.1 | chr12_26218182-26218182_C_T | R279W | Substitution | nonsynonymous SNV | 39% | 53 | 83 |
| CGLI 55 PT | FAM65B | family with sequence similarity 65, member B | CCDS47363.1 | chr6_24806653-24806653_T_A | 1052D>V | Substitution | Nonsynonymous coding | 39% | 20 | 72 |
| CGLI 55 PT | FAM194B | family with sequence similarity 194, member B | CCDS45045.1 | chr13_46135629-46135629_A_C | 428F>V | Substitution | Nonsynonymous coding | 39% | 29 | 394 |
| CGLI 55 PT | C3 | complement component 3 | CCDS32883.1 | chr19_6693022-6693022_G_T | 1101C>X | Substitution | Nonsense | 39% | 67 | 321 |
| CGLI 55 PT | C2orf71 | chromosome 2 open reading frame 71 | CCDS42669.1 | chr2_29294084-29294084_G_T | 1015S>Y | Substitution | Nonsynonymous coding | 39% | 38 | 76 |
| CGLI 55 PT | OR5P2 | olfactory receptor, family 5, subfamily P, member 2 | CCDS7762.1 | chr11_7818380-7818380_C_A | 37G>V | Substitution | Nonsynonymous coding | 39% | 9 | 55 |
| CGLI 55 PT | ACVR1 | activin A receptor, type I | CCDS2206.1 | chr2_158622516-158622516_C_T | 328G>E | Substitution | Nonsynonymous coding | 39% | 32 | 181 |
| CGLI 55 PT | XYLB | xylulokinase homolog (H. influenzae) | CCDS2678.1 | chr3_38407109-38407109_C_T | 130S>F | Substitution | Nonsynonymous coding | 39% | 60 | 180 |
| CGLI 55 PT | PTPRJ | protein tyrosine phosphatase, receptor type, J | CCDS7945.1 | chr11_48152063-48152063_C_G | 470I>M | Substitution | Nonsynonymous coding | 39% | 23 | 68 |
| CGLI 55 PT | SERPINI1 | serpin peptidase inhibitor, clade I (neuroserpin), member 1 | CCDS3203.1 | chr3_167508358-167508358_A_T | 150Y>F | Substitution | Nonsynonymous coding | 39% | 23 | 184 |
| CGLI 55 PT | LPIN3 | lipin 3 | CCDS33469.1 | chr20_39976284-39976284_T_A | 95D>E | Substitution | Nonsynonymous coding | 39% | 28 | 51 |
| CGLI 55 PT | MICA | MHC class I polypeptide-related sequence A | ENST00000376219 | chr6_31380162-31380162__CT | NA | Insertion | Frameshift | 39% | 21 | 102 |
| CGLI 55 PT | CDKL4 | Cyclin-dependent kinase-like 4;CDKL4;ortholog | CCDS33184.1 | chr2_39458601-39458601_T_C | T25A | Substitution | nonsynonymous SNV | 39% | 14 | 63 |
| CGLI 55 PT | MCHR2 | Melanin-concentrating hormone receptor 2;MCHR2;ortholog | CCDS5044.1 | chr6_100390984-100390984_C_T | R143H | Substitution | nonsynonymous SNV | 39% | 28 | 83 |
| CGLI 55 PT | OR1B1 | olfactory receptor, family 1, subfamily B, member 1 | CCDS35126.1 | chr9_125391771-125391771__A | NA | Insertion | Frameshift | 39% | 31 | 193 |
| CGLI 55 PT | TMPRSS11E | Transmembrane protease, serine 11E;TMPRSS11E;ortholog | CCDS33993.1 | chr4_69332450-69332450_A_G | S80G | Substitution | nonsynonymous SNV | 39% | 41 | 34 |
| CGLI 55 PT | TTC3 | E3 ubiquitin-protein ligase TTC3;TTC3;ortholog | CCDS13651.1 | chr21_38570267-38570267_G_T | G1793R | Substitution | nonsynonymous SNV | 39% | 17 | 63 |
| CGLI 55 PT | NEFH | neurofilament, heavy polypeptide | CCDS13858.1 | chr22_29876996-29876996_G_A | 249G>S | Substitution | Nonsynonymous coding | 39% | 22 | 39 |
| CGLI 55 PT | OR1J2 | Olfactory receptor 1J2;OR1J2;ortholog | CCDS35121.1 | chr9_125273386-125273386__T | Y102fs | Insertion | frameshift insertion | 38% | 15 | 83 |
| CGLI 55 PT | TMEM37 | transmembrane protein 37 | CCDS33261.1 | chr2_120194651-120194651_A_C | 70T>P | Substitution | Nonsynonymous coding | 38% | 15 | 425 |
| CGLI 55 PT | DSP | Desmoplakin;DSP;ortholog | CCDS4501.1 | chr6_7581384-7581384_T_C | L1654P | Substitution | nonsynonymous SNV | 38% | 33 | 34 |

Fig. 8 (continued)

| Sample | Gene | Description | CCDS/ENST | Location | AA Change | Type | Effect | % | Reads1 | Reads2 |
|---|---|---|---|---|---|---|---|---|---|---|
| CGLI 55 PT | TMEM151A | transmembrane protein 151A | CCDS8130.1 | chr11_66061946-66061946_G_A | 77A>T | Substitution | Nonsynonymous coding | 38% | 64 | 166 |
| CGLI 55 PT | NCAN | Neurocan core protein;NCAN;ortholog | CCDS12397.1 | chr19_19337469-19337469_C_A | T416N | Substitution | nonsynonymous SNV | 38% | 31 | 63 |
| CGLI 55 PT | CYP2A7P1 | cytochrome P450, family 2, subfamily A, polypeptide 7 pseudogene 1 | ENST00000301171 | chr19_41533462-41533462_C_T | 56D>N | Substitution | Nonsynonymous coding | 38% | 31 | 21 |
| CGLI 55 PT | SERPINI1 | Neuroserpin;SERPINI1;ortholog | CCDS3203.1 | chr3_167508358-167508358_A_T | Y150F | Substitution | nonsynonymous SNV | 38% | 28 | 63 |
| CGLI 55 PT | PRKCH | protein kinase C, eta | CCDS9752.1 | chr14_62014518-62014518_G_A | 607A>T | Substitution | Nonsynonymous coding | 38% | 42 | 406 |
| CGLI 55 PT | KRT24 | keratin 24 | CCDS11372.1 | chr17_38858135-38858135_A_ | NA | Deletion | Frameshift | 38% | 29 | 188 |
| CGLI 55 PT | ABCC6 | ATP-binding cassette, sub-family C (CFTR/MRP), member 6 | CCDS10568.1 | chr16_16281007-16281007_A_G | 614V>A | Substitution | Nonsynonymous coding | 38% | 27 | 14 |
| CGLI 55 PT | F5 | coagulation factor V (proaccelerin, labile factor) | CCDS1281.1 | chr1_169487696-169487696_C_T | 2100R>H | Substitution | Nonsynonymous coding | 38% | 19 | 18 |
| CGLI 55 PT | PDE5A | phosphodiesterase 5A, cGMP-specific | CCDS3713.1 | chr4_120463726-120463726_T_C | 487N>S | Substitution | Nonsynonymous coding | 38% | 30 | 277 |
| CGLI 55 PT | SMG6 | Telomerase-binding protein EST1A;SMG6;ortholog | CCDS11016.1 | chr17_2203212-2203212_G_A | R279C | Substitution | nonsynonymous SNV | 38% | 41 | 63 |
| CGLI 55 PT | AOAH | Acyloxyacyl hydrolase;AOAH;ortholog | CCDS5446.1 | chr7_36763728-36763728_G_A | T9M | Substitution | nonsynonymous SNV | 38% | 22 | 63 |
| CGLI 55 PT | QRICH2 | Glutamine-rich protein 2;QRICH2;ortholog | CCDS32741.1 | chr17_74289276-74289276_T_C | D345G | Substitution | nonsynonymous SNV | 38% | 48 | 34 |
| CGLI 55 PT | HNMT | histamine N-methyltransferase | CCDS2181.1 | chr2_138759649-138759649_C_T | 105T>I | Substitution | Nonsynonymous coding | 38% | 17 | 88 |
| CGLI 55 PT | DOCK6 | dedicator of cytokinesis 6 | CCDS45975.1 | chr19_11339660-11339660_A_T | 927I>N | Substitution | Nonsynonymous coding | 38% | 35 | 20 |
| CGLI 55 PT | SLC38A10 | Putative sodium-coupled neutral amino acid transporter 10;SLC38A10;ortholog | CCDS11780.1 | chr17_79244731-79244731_G_A | A373V | Substitution | nonsynonymous SNV | 38% | 21 | 34 |
| CGLI 55 PT | CCDC39 | coiled-coil domain containing 39 | CCDS46964.1 | chr3_180332813-180332813_C_T | 908E>K | Substitution | Nonsynonymous coding | 38% | 9 | 33 |
| CGLI 55 PT | GOLGA4 | golgin A4 | CCDS2666.1 | chr3_37360621-37360621_A_G | 494Q>R | Substitution | Nonsynonymous coding | 38% | 16 | 62 |
| CGLI 55 PT | OR5P2 | olfactory receptor, family 5, subfamily P, member 2 | CCDS7782.1 | chr11_7818389-7818389_A_G | 34I>T | Substitution | Nonsynonymous coding | 38% | 9 | 51 |
| CGLI 55 PT | C11orf40 | chromosome 11 open reading frame 40 | CCDS31354.1 | chr11_4593486-4593489_AG_ | NA | Deletion | Frameshift | 37% | 19 | 98 |
| CGLI 55 PT | OR51G2 | olfactory receptor, family 51, subfamily G, member 2 | CCDS31365.1 | chr11_4936212-4936212_G_A | 228R>C | Substitution | Nonsynonymous coding | 37% | 57 | 193 |
| CGLI 55 PT | RELT | RELT tumor necrosis factor receptor | ENST00000438119 | chr11_73104843-73104843__C | NA | Insertion | Frameshift | 37% | 61 | 114 |
| CGLI 55 PT | PLXNB2 | Plexin-B2;PLXNB2;ortholog | CCDS43035.1 | chr22_50716644-50716644_C_T | E1597K | Substitution | nonsynonymous SNV | 37% | 42 | 34 |
| CGLI 55 PT | BZRAP1 | benzodiazepine receptor (peripheral) associated protein 1 | ENST00000355701 | chr17_56379766-56379766_C_T | 1863G>R | Substitution | Nonsynonymous coding | 37% | 20 | 133 |
| CGLI 55 PT | C11orf63 | chromosome 11 open reading frame 63 | CCDS8438.1 | chr11_122774942-122774944_GGA_ | NA | Deletion | In-frame deletion | 37% | 44 | 405 |
| CGLI 55 PT | LYRM4 | LYR motif-containing protein 4;LYRM4;ortholog | CCDS4493.1 | chr6_5109716-5109716_C_T | G73S | Substitution | nonsynonymous SNV | 37% | 17 | 34 |
| CGLI 55 PT | SLC22A1 | solute carrier family 22 (organic cation transporter), member 1 | CCDS5274.1 | chr6_160560861-160560863_ATG_ | NA | Deletion | In-frame deletion | 37% | 14 | 117 |
| CGLI 55 PT | DNAH8 | dynein, axonemal, heavy chain 8 | CCDS4838.1 | chr6_38885011-38885011_A_ | NA | Deletion | Frameshift | 37% | 7 | 144 |
| CGLI 55 PT | GBA2 | glucosidase, beta (bile acid) 2 | CCDS6589.1 | chr9_35748379-35748379_A_C | 108L>R | Substitution | Nonsynonymous coding | 37% | 28 | 339 |
| CGLI 55 PT | MEA1 | male-enhanced antigen 1 | CCDS4879.1 | chr6_42980709-42980711_CCT_ | NA | Deletion | In-frame deletion | 37% | 81 | 436 |
| CGLI 55 PT | OSBP2 | oxysterol binding protein 2 | CCDS43002.1 | chr22_31137305-31137305_G_A | 268A>T | Substitution | Nonsynonymous coding | 37% | 22 | 89 |
| CGLI 55 PT | NEFH | neurofilament, heavy polypeptide | CCDS13858.1 | chr22_29886043-29886043_A_C | 205E>A | Substitution | Nonsynonymous coding | 37% | 74 | 93 |
| CGLI 55 PT | MUC19 | mucin 19, oligomeric | ENST00000398702 | chr12_40915475-40915475_A_ | NA | Deletion | Frameshift | 36% | 43 | 48 |
| CGLI 55 PT | LPIN3 | Phosphatidate phosphatase LPIN3;LPIN3;ortholog | CCDS33466.1 | chr20_39980772-39980772_A_T | E425D | Substitution | nonsynonymous SNV | 36% | 47 | 63 |
| CGLI 55 PT | ATP10A | ATPase, class V, type 10A | CCDS32178.1 | chr15_25961260-25961260_G_C | 228T>S | Substitution | Nonsynonymous coding | 36% | 4 | 35 |
| CGLI 55 PT | C2orf47 | chromosome 2 open reading frame 47 | CCDS2329.1 | chr2_200824505-200824505_C_T | 184T>I | Substitution | Nonsynonymous coding | 36% | 4 | 91 |
| CGLI 55 PT | LRRC36 | leucine rich repeat containing 36 | CCDS32467.1 | chr16_67412588-67412588_G_A | 635V>M | Substitution | Nonsynonymous coding | 36% | 20 | 78 |
| CGLI 55 PT | HRG | histidine-rich glycoprotein | CCDS3280.1 | chr3_186390627-186390627_C_T | 204P>S | Substitution | Nonsynonymous coding | 36% | 34 | 234 |
| CGLI 55 PT | HAVCR1 | Hepatitis A virus cellular receptor 1;HAVCR1;ortholog | CCDS43392.1 | chr5_156479569-156479569__GTT | S201G | Insertion | nonframeshift insertion | 36% | 108 | 63 |
| CGLI 55 PT | TTLL4 | Tubulin polyglutamylase TTLL4;TTLL4;ortholog | CCDS32422.1 | chr2_219604866-219604866_C_T | R529C | Substitution | nonsynonymous SNV | 36% | 13 | 63 |
| CGLI 55 PT | MCM9 | minichromosome maintenance complex component 9 | ENST00000383319 | chr6_119137094-119137094_C_A | 775K>N | Substitution | Nonsynonymous coding | 36% | 26 | 221 |

Fig. 8 (continued)

| | | | | | | | | | |
|---|---|---|---|---|---|---|---|---|---|
| CGLI 55 PT | SETD1A | Histone-lysine N-methyltransferase SETD1A;SETD1A;ortholog | CCDS32435.1 | chr16_30975475-30975475_G_T | V234L | Substitution | nonsynonymous SNV | 36% | 61 | 63 |
| CGLI 55 PT | ETFB | Electron transfer flavoprotein subunit beta;ETFB;ortholog | CCDS33065.1 | chr19_51857615-51857615__G | P93fs | insertion | frameshift insertion | 36% | 23 | 34 |
| CGLI 55 PT | SI | Sucrase-isomaltase, intestinal;SI;ortholog | CCDS3196.1 | chr3_164735625-164735625_C_T | R1186H | Substitution | nonsynonymous SNV | 36% | 14 | 63 |
| CGLI 55 PT | ZNF235 | zinc finger protein 235 | CCDS33048.1 | chr19_44793250-44793250_G_A | 113A>V | Substitution | Nonsynonymous coding | 36% | 28 | 147 |
| CGLI 55 PT | GLRX5 | glutaredoxin 5 | CCDS9836.1 | chr14_96010369-96010369_G_C | 127Q>H | Substitution | Nonsynonymous coding | 36% | 21 | 47 |
| CGLI 55 PT | TPM2 | tropomyosin 2 (beta) | ENST00000378300 | chr9_35682765-35682765__G | NA | Insertion | Frameshift | 36% | 37 | 116 |
| CGLI 55 PT | XIRP2 | xin actin-binding repeat containing 2 | CCDS42799.1 | chr2_167992561-167992561_G_A | 184R>H | Substitution | Nonsynonymous coding | 35% | 12 | 58 |
| CGLI 55 PT | APOL1 | Apolipoprotein L1;APOL1;ortholog | CCDS46702.1 | chr22_36661376-36661376_T_C | V147A | Substitution | nonsynonymous SNV | 35% | 37 | 63 |
| CGLI 55 PT | SLC26A6 | Solute carrier family 26 member 6;SLC26A6;ortholog | CCDS63627.1 | chr3_48687381-48687381_T_G | I378L | Substitution | nonsynonymous SNV | 35% | 44 | 34 |
| CGLI 55 PT | PIK3C2G | phosphatidylinositol-4-phosphate 3-kinase, catalytic subunit type 2 gamma | CCDS44839.1 | chr12_18435399-18435401_CCC_ | NA | Deletion | In-frame deletion | 35% | 19 | 196 |
| CGLI 55 PT | NAV1 | neuron navigator 1 | CCDS1414.1 | chr1_201750407-201750407_C_T | 545H>Y | Substitution | Nonsynonymous coding | 35% | 59 | 123 |
| CGLI 55 PT | CDKL4 | cyclin-dependent kinase-like 4 | CCDS33184.1 | chr2_39456801-39456801_T_C | 25T>A | Substitution | Nonsynonymous coding | 35% | 7 | 321 |
| CGLI 55 PT | SCN1B | Sodium channel subunit beta-1;SCN1B;ortholog | CCDS46047.1 | chr19_35524688-35524688_G_A | A185T | Substitution | nonsynonymous SNV | 35% | 52 | 63 |
| CGLI 55 PT | TSR1 | TSR1, 20S rRNA accumulation, homolog (S. cerevisiae) | CCDS32525.1 | chr17_2227572-2227572_G_A | 778T>I | Substitution | Nonsynonymous coding | 35% | 17 | 417 |
| CGLI 55 PT | CNTNAP5 | contactin associated protein-like 5 | CCDS46461.1 | chr2_125320799-125320799_T_G | 551L>W | Substitution | Nonsynonymous coding | 35% | 9 | 121 |
| CGLI 55 PT | DISC1 | disrupted in schizophrenia 1 | CCDS31055.1 | chr1_231830295-231830295_G_A | 264R>Q | Substitution | Nonsynonymous coding | 35% | 159 | 369 |
| CGLI 55 PT | XRCC6BP1 | XRCC6 binding protein 1 | CCDS41802.1 | chr12_58340774-58340774_T_C | NA | Substitution | Splice site acceptor | 34% | 10 | 154 |
| CGLI 55 PT | HNRNPU | heterogeneous nuclear ribonucleoprotein U (scaffold attachment factor A) | CCDS41479.1 | chr1_245021435-245021435_T_C | 458N>D | Substitution | Nonsynonymous coding | 34% | 53 | 199 |
| CGLI 55 PT | FCRL5 | Fc receptor-like protein 5;FCRL5;ortholog | CCDS1165.1 | chr1_157514207-157514207_C_T | R230K | Substitution | nonsynonymous SNV | 34% | 47 | 63 |
| CGLI 55 PT | TMEM37 | transmembrane protein 37 | CCDS33291.1 | chr2_120194654-120194654_A_G | 71I>V | Substitution | Nonsynonymous coding | 34% | 14 | 416 |
| CGLI 55 PT | MRI1 | Methylthioribose-1-phosphate isomerase;MRI1;ortholog | CCDS12297.1 | chr19_13879797-13879797_T_A | I248N | Substitution | nonsynonymous SNV | 34% | 23 | 63 |
| CGLI 55 PT | MLH1 | mutL homolog 1, colon cancer, nonpolyposis type 2 (E. coli) | CCDS2663.1 | chr3_37067449-37067449_G_C | 454G>R | Substitution | Nonsynonymous coding | 34% | 40 | 90 |
| CGLI 55 PT | POLR1B | DNA-directed RNA polymerase I subunit RPA2;POLR1B;ortholog | CCDS62988.1 | chr2_113300064-113300064_G_A | G36D | Substitution | nonsynonymous SNV | 34% | 53 | 63 |
| CGLI 55 PT | VWDE | von Willebrand factor D and EGF domains | CCDS47544.1 | chr7_12376635-12376835_C_T | 1477R>H | Substitution | Nonsynonymous coding | 34% | 36 | 100 |
| CGLI 55 PT | MYBPH | myosin binding protein H | CCDS30975.1 | chr1_203140266-203140266_G_A | 286Q>X | Substitution | Nonsense | 34% | 105 | 439 |
| CGLI 55 PT | OR6C1 | Olfactory receptor 6C1;OR6C1;ortholog | CCDS31818.1 | chr12_55714407-55714407__A | T4fs | insertion | frameshift insertion | 33% | 11 | 34 |
| CGLI 55 PT | ARHGEF17 | Rho guanine nucleotide exchange factor (GEF) 17 | CCDS8221.1 | chr11_73020376-73020376__CTC | NA | Insertion | in-frame insertion | 33% | 41 | 139 |
| CGLI 55 PT | CELA1 | chymotrypsin-like elastase family, member 1 | CCDS8012.1 | chr12_51723599-51723599__G | NA | Insertion | Frameshift | 33% | 40 | 280 |
| CGLI 55 PT | HOXC13 | homeobox C13 | CCDS8865.1 | chr12_54332734-54332734__TTA | NA | Insertion | in-frame insertion | 33% | 8 | 40 |
| CGLI 55 PT | LNX1 | ligand of numb-protein X 1, E3 ubiquitin protein ligase | CCDS47057.1 | chr4_54327212-54327212__A | NA | Insertion | Splice site acceptor | 33% | 7 | 85 |
| CGLI 55 PT | TCF12 | transcription factor 12 | CCDS10160.1 | chr15_57565320-57565320_G_C | 813R>P | Substitution | Nonsynonymous coding | 33% | 13 | 127 |
| CGLI 55 PT | QRICH2 | glutamine rich 2 | CCDS32741.1 | chr17_74289276-74289276_T_C | 345D>G | Substitution | Nonsynonymous coding | 33% | 32 | 283 |
| CGLI 55 PT | MUC17 | Mucin-17;MUC17;ortholog | CCDS34711.1 | chr7_100678634-100678634_A_G | N1313D | Substitution | nonsynonymous SNV | 33% | 91 | 63 |
| CGLI 55 PT | OR8B3 | Olfactory receptor 8B3;OR8B3;ortholog | CCDS31709.1 | chr11_124266698-124266698__G | L184fs | Insertion | frameshift insertion | 33% | 25 | 63 |
| CGLI 55 PT | HHATL | Protein-cysteine N-palmitoyltransferase HHAT-like protein;HHATL;ortholog | CCDS2704.1 | chr3_42739670-42739672_GAA_ | 219_219del | Deletion | nonframeshift deletion | 33% | 21 | 34 |
| CGLI 55 PT | ADAMTSL3 | ADAMTS-like protein 3;ADAMTSL3;ortholog | CCDS10326.1 | chr15_84651394-84651394_G_A | R1005H | Substitution | nonsynonymous SNV | 33% | 29 | 34 |
| CGLI 55 PT | FKBP9 | Peptidyl-prolyl cis-trans isomerase FKBP9;FKBP9;ortholog | CCDS5439.1 | chr7_33016103-33016103_A_G | D232G | Substitution | nonsynonymous SNV | 32% | 23 | 63 |

Fig. 8 (continued)

| | | | | | | | | | | |
|---|---|---|---|---|---|---|---|---|---|---|
| CGLI 55 PT | NSL1 | NSL1, MIND kinetochore complex component, homolog (S. cerevisiae) | CCDS1509.1 | chr1_212965088-212965088_C_G | 6E>D | Substitution | Nonsynonymous coding | 32% | 70 | 200 |
| CGLI 55 PT | GDPD4 | Glycerophosphodiester phosphodiesterase domain-containing protein 4;GDPD4;ortholog | CCDS8249.1 | chr11_76954789-76954789__A | N397fs | Insertion | frameshift insertion | 32% | 10 | 34 |
| CGLI 55 PT | SAAL1 | serum amyloid A-like 1 | CCDS31439.1 | chr11_18127559-18127559__CGG | NA | Insertion | In-frame insertion | 32% | 47 | 248 |
| CGLI 55 PT | PRKCH | Protein kinase C eta type;PRKCH;ortholog | CCDS9752.1 | chr14_62014518-62014518_G_A | A607T | Substitution | nonsynonymous SNV | 32% | 16 | 34 |
| CGLI 55 PT | STRN | striatin, calmodulin binding protein | CCDS1784.1 | chr2_37129726-37129726_C_T | NA | Substitution | Splice site donor | 32% | 16 | 151 |
| CGLI 55 PT | DTX3L | deltex 3-like (Drosophila) | CCDS3015.1 | chr3_122284745-122284747_TTG__ | NA | Deletion | In-frame deletion | 32% | 29 | 177 |
| CGLI 55 PT | ATP6V0A2 | ATPase, H+ transporting, lysosomal V0 subunit a2 | CCDS9254.1 | chr12_124241506-124241506_C_T | 813A>V | Substitution | Nonsynonymous coding | 32% | 20 | 85 |
| CGLI 55 PT | TMEM37 | transmembrane protein 37 | CCDS33281.1 | chr2_120194849-120194849_A_T | 69Q>L | Substitution | Nonsynonymous coding | 32% | 13 | 433 |
| CGLI 55 PT | HIST1H3C | #N/A | CCDS4578.1 | chr6_26045721-26045721_A_T | K28M | Substitution | nonsynonymous SNV | 32% | 19 | 83 |
| CGLI 55 PT | CYP1B1 | cytochrome P450, family 1, subfamily B, polypeptide 1 | CCDS1793.1 | chr2_38302390-38302390_G_C | 48R>G | Substitution | Nonsynonymous coding | 32% | 25 | 104 |
| CGLI 55 PT | TRPM3 | transient receptor potential cation channel, subfamily M, member 3 | CCDS43835.1 | chr9_73458046-73458046__A | NA | Insertion | Splice site acceptor | 31% | 11 | 45 |
| CGLI 55 PT | CNGB1 | cyclic nucleotide gated channel beta 1 | CCDS42169.1 | chr16_57948224-57948224_G_T | 745L>I | Substitution | Nonsynonymous coding | 31% | 27 | 41 |
| CGLI 55 PT | USH2A | Usher syndrome 2A (autosomal recessive, mild) | CCDS31025.1 | chr1_216462682-216462682_T_A | 644D>V | Substitution | Nonsynonymous coding | 31% | 42 | 130 |
| CGLI 55 PT | ACVR1 | Activin receptor type-1;ACVR1;ortholog | CCDS2206.1 | chr2_158622516-158622516_C_T | G328E | Substitution | nonsynonymous SNV | 31% | 31 | 83 |
| CGLI 55 PT | MAN2A2 | Alpha-mannosidase 2x;MAN2A2;ortholog | CCDS32332.1 | chr15_91456592-91456592_A_G | I892V | Substitution | nonsynonymous SNV | 31% | 17 | 34 |
| CGLI 55 PT | DEPDC1 | DEP domain containing 1 | ENST00000443267 | chr1_68947311-68947311_A_C | 13Y>D | Substitution | Nonsynonymous coding | 31% | 4 | 89 |
| CGLI 55 PT | FCRL5 | Fc receptor-like 5 | CCDS1165.1 | chr1_157514207-157514207_A_G | 230R>K | Substitution | Nonsynonymous coding | 31% | 64 | 139 |
| CGLI 55 PT | FMO5 | flavin containing monooxygenase 5 | CCDS926.1 | chr1_146685007-146685007_C_G | 119D>H | Substitution | Nonsynonymous coding | 31% | 22 | 124 |
| CGLI 55 PT | ERAP2 | Endoplasmic reticulum aminopeptidase 2;ERAP2;ortholog | CCDS4086.1 | chr5_96222432-96222433_TT_ | L263fs | Deletion | frameshift deletion | 30% | 17 | 34 |
| CGLI 55 PT | UNC13A | unc-13 homolog A (C. elegans) | CCDS46013.1 | chr19_17799247-17799247__GG | NA | Insertion | Frameshift | 30% | 10 | 49 |
| CGLI 55 PT | TTLL4 | tubulin tyrosine ligase-like family, member 4 | CCDS2422.1 | chr2_219604866-219604866_C_T | 525R>C | Substitution | Nonsynonymous coding | 30% | 16 | 93 |
| CGLI 55 PT | CCDC169 | coiled-coil domain containing 169 | CCDS45028.1 | chr13_36857807-36857807_G_T | 86L>I | Substitution | Nonsynonymous coding | 30% | 6 | 193 |
| CGLI 55 PT | OR51J1 | olfactory receptor, family 51, subfamily J, member 1 (gene/pseudogene) | ENST00000332043 | chr11_5424388-5424388__TATC | NA | Insertion | Frameshift | 30% | 60 | 429 |
| CGLI 55 PT | GSDMB | gasdermin B | CCDS42313.1 | chr17_38062196-38062196_G_A | 298P>S | Substitution | Nonsynonymous coding | 30% | 37 | 234 |
| CGLI 55 PT | ASPHD1 | Aspartate beta-hydroxylase domain-containing protein 1;ASPHD1;ortholog | CCDS10660.1 | chr16_29912803-29912803__GGT | Q170delins QG | Insertion | nonframeshift insertion | 30% | 34 | 63 |
| CGLI 55 PT | ABCA13 | ATP-binding cassette, sub-family A (ABC1), member 13 | CCDS47584.1 | chr7_48318702-48318704_AAT__ | NA | Deletion | In-frame deletion | 29% | 5 | 192 |
| CGLI 55 PT | TOX3 | TOX high mobility group box family member 3 | NM_001080430 | chr16_52498096-52498096_G_A | 53T>I | Substitution | Nonsynonymous coding | 29% | 17 | 80 |
| CGLI 55 PT | N4BP2 | NEDD4-binding protein 2;N4BP2;ortholog | CCDS3457.1 | chr4_40123540-40123540_T_C | V1270A | Substitution | nonsynonymous SNV | 29% | 12 | 63 |
| CGLI 55 PT | ZFP28 | Zinc finger protein 28 homolog;ZFP28;ortholog | CCDS12946.1 | chr19_57060359-57060359_C_T | P166S | Substitution | nonsynonymous SNV | 29% | 14 | 34 |
| CGLI 55 PT | ZAN | zonadhesin | ENST00000419263 | chr7_100350303-100350303_A_G | 659I>V | Substitution | Nonsynonymous coding | 29% | 52 | 907 |
| CGLI 55 PT | HNRNPU | Heterogeneous nuclear ribonucleoprotein U;HNRNPU;ortholog | CCDS31081.1 | chr1_245021435-245021435_T_C | N439D | Substitution | nonsynonymous SNV | 29% | 41 | 63 |
| CGLI 55 PT | TPM2 | tropomyosin 2 (beta) | CCDS6587.1 | chr9_35683241-35683241__G | NA | Insertion | Splice site acceptor | 29% | 28 | 37 |
| CGLI 55 PT | COPB2 | coatomer protein complex, subunit beta 2 (beta prime) | CCDS3108.1 | chr3_139081332-139081332_A_T | 638S>T | Substitution | Nonsynonymous coding | 29% | 4 | 99 |
| CGLI 55 PT | IL10 | interleukin 10 | CCDS1467.1 | chr1_206943184-206943184_G_A | 145A>V | Substitution | Nonsynonymous coding | 29% | 14 | 49 |
| CGLI 55 PT | MACROD2 | MACRO domain containing 2 | CCDS13120.2 | chr20_15948230-15948230_G_C | 314G>R | Substitution | Nonsynonymous coding | 29% | 14 | 133 |
| CGLI 55 PT | RP11-17M16.1 | Uncharacterized protein | ENST00000495150 | chr6_74208496-74208496_A_T | 114I>F | Substitution | Nonsynonymous coding | 29% | 8 | 28 |
| CGLI 55 PT | DCST2 | DC-STAMP domain containing 2 | CCDS1082.2 | chr1_154999134-154999134_C_T | 467R>H | Substitution | Nonsynonymous coding | 28% | 39 | 437 |
| CGLI 55 PT | CD36 | CD36 molecule (thrombospondin receptor) | CCDS34673.1 | chr7_80292426-80292426_G_A | 184D>N | Substitution | Nonsynonymous coding | 28% | 7 | 58 |

Fig. 8 (continued)

| | | | | | | | | | | |
|---|---|---|---|---|---|---|---|---|---|---|
| CGLI 55 PT | GNLY | granulysin | CCDS46354.1 | chr2_85922122-85922122__A | NA | Insertion | Splice site donor | 28% | 15 | 152 |
| CGLI 55 PT | TNRC6A | trinucleotide repeat containing 6A | ENST00000395801 | chr16_24826661-24826662_TG_ | NA | Deletion | Frameshift | 27% | 16 | 161 |
| CGLI 55 PT | FMO3 | flavin containing monooxygenase 3 | CCDS1292.1 | chr1_171080060-171080080_G_A | 257V>M | Substitution | Nonsynonymous coding | 27% | 16 | 173 |
| CGLI 55 PT | GOLGA4 | Golgin subfamily A member 4;GOLGA4;ortholog | CCDS2686.1 | chr3_37360621-37360621_A_G | Q494R | Substitution | nonsynonymous SNV | 27% | 10 | 63 |
| CGLI 55 PT | PNP | purine nucleoside phosphorylase | CCDS9552.1 | chr14_20940606-20940606_G_A | 51G>S | Substitution | Nonsynonymous coding | 27% | 11 | 128 |
| CGLI 55 PT | KIF27 | kinesin family member 27 | CCDS6685.1 | chr9_86452020-86452020_C_T | 1386A>T | Substitution | Nonsynonymous coding | 27% | 8 | 14 |
| CGLI 55 PT | MUC17 | Mucin-17;MUC17;ortholog | CCDS34711.1 | chr7_100679484-100679484_C_ | N1313D | Deletion | frameshift deletion | 27% | 76 | 63 |
| CGLI 55 PT | TFAP2A | Transcription factor AP-2 alpha;TFAP2A;ortholog | CCDS34337.1 | chr6_10410163-10410163_A_G | S145P | Substitution | nonsynonymous SNV | 26% | 14 | 63 |
| CGLI 55 PT | CHIA | chitinase, acidic | CCDS41368.1 | chr1_111861782-111861782_A_G | 319D>G | Substitution | Nonsynonymous coding | 26% | 5 | 107 |
| CGLI 55 PT | GDPD4 | glycerophosphodiester phosphodiesterase domain containing 4 | CCDS58249.1 | chr11_76954789-76954789__A | NA | Insertion | Frameshift | 26% | 12 | 41 |
| CGLI 55 PT | SOAT1 | Sterol O-acyltransferase 1;SOAT1;ortholog | CCDS58046.1 | chr1_179304682-179304684_TGA_ | 8_9del | Deletion | nonframeshift deletion | 26% | 14 | 63 |
| CGLI 55 PT | C14orf23 | chromosome 14 open reading frame 23 | ENST00000399387 | chr14_29261306-29261306__AAC | NA | Insertion | in-frame insertion | 26% | 21 | 184 |
| CGLI 55 PT | NUTM2G | #N/A | CCDS43854.1 | chr9_99694526-99694526__A | Q180fs | Insertion | frameshift insertion | 26% | 18 | 34 |
| CGLI 55 PT | CDH5 | cadherin 5, type 2 (vascular endothelium) | CCDS10804.1 | chr16_66402453-66402453_C_T | 527T>M | Substitution | Nonsynonymous coding | 25% | 5 | 108 |
| CGLI 55 PT | CHIA | chitinase, acidic | CCDS41368.1 | chr1_111861781-111861781_G_A | 319D>N | Substitution | Nonsynonymous coding | 25% | 5 | 108 |
| CGLI 55 PT | TMEM37 | transmembrane protein 37 | CCDS33281.1 | chr2_120194648-120194648_C_G | 69Q>E | Substitution | Nonsynonymous coding | 24% | 10 | 428 |
| CGLI 55 PT | TMEM37 | transmembrane protein 37 | CCDS33281.1 | chr2_120194656-120194656_C_G | 71I>M | Substitution | Nonsynonymous coding | 24% | 9 | 428 |
| CGLI 55 PT | XRCC3 | X-ray repair complementing defective repair in Chinese hamster cells 3 | CCDS9984.1 | chr14_104165753-104165753_G_A | 241T>M | Substitution | Nonsynonymous coding | 23% | 18 | 232 |
| CGLI 55 PT | ARHGEF17 | Rho guanine nucleotide exchange factor 17;ARHGEF17;ortholog | CCDS8221.1 | chr11_73020376-73020376__CTC | C231delins CL | Insertion | nonframeshift insertion | 23% | 11 | 34 |
| CGLI 55 PT | ZNF444 | zinc finger protein 444 | CCDS12939.1 | chr19_58671290-58671290_G_C | 235S>T | Substitution | Nonsynonymous coding | 23% | 7 | 70 |
| CGLI 55 PT | OR9G1 | olfactory receptor, family 9, subfamily G, member 1 | CCDS31536.1 | chr11_56468297-56468297_C_A | 145A>E | Substitution | Nonsynonymous coding | 23% | 36 | 541 |
| CGLI 55 PT | ZNF444 | zinc finger protein 444 | CCDS12939.1 | chr19_58671289-58671289_A_C | 235S>R | Substitution | Nonsynonymous coding | 22% | 7 | 68 |
| CGLI 55 PT | FMN2 | formin 2 | CCDS31069.2 | chr1_240255561-240255561_G_A | 51G>E | Substitution | Nonsynonymous coding | 22% | 8 | 71 |
| CGLI 55 PT | OR9G1,OR9G9 | #N/A | CCDS31536.1 | chr11_56468297-56468297_C_A | A145E | Substitution | nonsynonymous SNV | 21% | 28 | 34 |
| CGLI 55 PT | F5 | Coagulation factor V;F5;ortholog | CCDS1281.1 | chr1_169487696-169487696_C_T | R2100H | Substitution | nonsynonymous SNV | 21% | 15 | 63 |
| CGLI 55 PT | RBMX | RNA-binding motif protein, X chromosome;RBMX;ortholog | CCDS14661.1 | chrX_135956572-135956572__GG | P302fs | Insertion | frameshift insertion | 21% | 8 | 63 |
| CGLI 55 PT | CHIA | chitinase, acidic | CCDS41368.1 | chr1_111861780-111861780_G_A | 318W>X | Substitution | Nonsense | 21% | 4 | 109 |
| CGLI 55 PT | OR10C1 | olfactory receptor, family 10, subfamily C, member 1 | ENST00000383554 | chr6_29385612-29385627_GCCTGTGGGAACACTG_ | NA | Deletion | Frameshift | 20% | 4 | 675 |
| CGLI 55 PT | RAD23B | RAD23 homolog B (S. cerevisiae) | ENST00000374678 | chr9_110093971-110093971__A | NA | Insertion | Frameshift | 20% | 9 | 160 |
| CGLI 55 PT | SLC22A1 | solute carrier family 22 (organic cation transporter), member 1 | CCDS5274.1 | chr6_160560883-160560883_G_T | 420M>I | Substitution | Nonsynonymous coding | 20% | 7 | 114 |
| CGLI 55 PT | HYDIN | Hydrocephalus-inducing protein homolog;HYDIN;ortholog | CCDS59269.1 | chr16_70894610-70894610_A_G | I3991T | Substitution | nonsynonymous SNV | 20% | 41 | 34 |
| CGLI 55 PT | TFAP2A | transcription factor AP-2 alpha (activating enhancer binding protein 2 alpha) | CCDS4510.1 | chr6_10410163-10410163_A_G | 151S>P | Substitution | nonsynonymous coding | 19% | 36 | 233 |
| CGLI 55 PT | IL10 | Interleukin-10;IL10;ortholog | CCDS1467.1 | chr1_206943184-206943184_G_A | A145V | Substitution | nonsynonymous SNV | 19% | 11 | 63 |
| CGLI 55 PT | HYDIN | HYDIN, axonemal central pair apparatus protein | CCDS42189.1 | chr16_70894610-70894610_A_G | 3990I>T | Substitution | Nonsynonymous coding | 19% | 57 | 365 |
| CGLI 55 PT | ACADVL | acyl-CoA dehydrogenase, very long chain | ENST00000356839 | chr17_7123232-7123232_C_G | 23P>A | Substitution | Nonsynonymous coding | 19% | 14 | 148 |
| CGLI 55 PT | TMEM37 | transmembrane protein 37 | CCDS33281.1 | chr2_120194657-120194657_T_C | 72C>R | Substitution | Nonsynonymous coding | 18% | 7 | 418 |
| CGLI 55 PT | BCLAF1 | BCL2-associated transcription factor 1 | CCDS5177.1 | chr6_136582417-136582417_G_A | 915R>C | Substitution | Nonsynonymous coding | 18% | 13 | 216 |
| CGLI 55 PT | LAPTM4B | lysosomal protein transmembrane 4 beta | ENST00000378722 | chr8_98787952-98787952_G_C | 42W>C | Substitution | Nonsynonymous coding | 18% | 8 | 54 |
| CGLI 55 PT | UNC13A | unc-13 homolog A (C. elegans) | CCDS46013.1 | chr19_17799245-17799245_C_G | 53A>P | Substitution | Nonsynonymous coding | 18% | 5 | 42 |
| CGLI 55 PT | ACADVL | acyl-CoA dehydrogenase, very long chain | ENST00000356839 | chr17_7123256-7123256_C_G | 31Q>E | Substitution | Nonsynonymous coding | 18% | 15 | 139 |

Fig. 8 (continued)

| Sample | Gene | Description | Transcript | Location | Change | Type | Effect | % | A | B |
|---|---|---|---|---|---|---|---|---|---|---|
| CGLI 55 PT | HYDIN | HYDIN, axonemal central pair apparatus protein | CCDS42189.1 | chr16_70894024-70894024_C_T | 4025A>T | Substitution | Nonsynonymous coding | 17% | 26 | 170 |
| CGLI 55 PT | ACADVL | acyl-CoA dehydrogenase, very long chain | ENST00000356839 | chr17_7123230-7123230_C_G | 22A>G | Substitution | Nonsynonymous coding | 17% | 13 | 148 |
| CGLI 55 PT | TRAK2 | trafficking protein, kinesin binding 2 | CCDS2347.1 | chr2_202245945-202245945__A | NA | Insertion | Splice site acceptor | 17% | 6 | 102 |
| CGLI 55 PT | TMEM37 | transmembrane protein 37 | CCDS33281.1 | chr2_120194646-120194646_A_G | 68N>S | Substitution | Nonsynonymous coding | 17% | 7 | 409 |
| CGLI 55 PT | ACADVL | acyl-CoA dehydrogenase, very long chain | ENST00000356839 | chr17_7123257-7123257_A_G | 31Q>R | Substitution | Nonsynonymous coding | 16% | 14 | 141 |
| CGLI 55 PT | PDE4DIP | phosphodiesterase 4D interacting protein | CCDS30824.1 | chr1_144873963-144873963_T__ | NA | Deletion | Frameshift | 16% | 29 | 242 |
| CGLI 55 PT | ARHGEF17 | Rho guanine nucleotide exchange factor (GEF) 17 | CCDS8221.1 | chr11_73020392-73020392_G_A | 237A>T | Substitution | Nonsynonymous coding | 16% | 18 | 118 |
| CGLI 55 PT | ARHGEF17 | Rho guanine nucleotide exchange factor (GEF) 17 | CCDS8221.1 | chr11_73020390-73020390_T_C | 236I>T | Substitution | Nonsynonymous coding | 16% | 17 | 114 |
| CGLI 55 PT | CLDN7 | claudin 7 | ENST00000397317 | chr17_7165400-7165400_A_G | 8L>P | Substitution | Nonsynonymous coding | 16% | 15 | 336 |
| CGLI 55 PT | TICAM1 | toll-like receptor adaptor molecule 1 | CCDS12136.1 | chr19_4817289-4817289__AGG | NA | Insertion | In-frame insertion | 16% | 11 | 79 |
| CGLI 55 PT | ARHGEF17 | Rho guanine nucleotide exchange factor (GEF) 17 | CCDS8221.1 | chr11_73020393-73020393_C_T | 237A>V | Substitution | Nonsynonymous coding | 15% | 17 | 119 |
| CGLI 55 PT | EVX1 | even-skipped homeobox 1 | CCDS5413.1 | chr7_27285709-27285709_G_T | 297A>S | Substitution | Nonsynonymous coding | 15% | 8 | 399 |
| CGLI 55 PT | EVX1 | even-skipped homeobox 1 | CCDS5413.1 | chr7_27285712-27285712_T_G | 298S>A | Substitution | Nonsynonymous coding | 15% | 8 | 392 |
| CGLI 55 PT | MUC20 | mucin 20, cell surface associated | ENST00000436408 | chr3_195452649-195452649_C_T | 392P>L | Substitution | Nonsynonymous coding | 15% | 15 | 81 |
| CGLI 55 PT | ACADVL | acyl-CoA dehydrogenase, very long chain | ENST00000356839 | chr17_7123229-7123229_G_C | 22A>P | Substitution | Nonsynonymous coding | 15% | 11 | 153 |
| CGLI 55 PT | KNDC1 | kinase non-catalytic C-lobe domain (KIND) containing 1 | CCDS7674.1 | chr10_135032440-135032440_G_A | 1595A>T | Substitution | Nonsynonymous coding | 15% | 13 | 159 |
| CGLI 55 PT | PIEZO1 | piezo-type mechanosensitive ion channel component 1 | NM_001142864 | chr16_88789686-88789686_G_C | 1483Q>E | Substitution | Nonsynonymous coding | 15% | 24 | 302 |
| CGLI 55 PT | KANK3 | KN motif and ankyrin repeat domains 3 | CCDS12199.1 | chr19_8398960-8398960_C_T | 490G>S | Substitution | Nonsynonymous coding | 15% | 8 | 100 |
| CGLI 55 PT | SOAT1 | sterol O-acyltransferase 1 | CCDS1330.1 | chr1_179304682-179304684_TGA_ | NA | Deletion | In-frame deletion | 14% | 6 | 51 |
| CGLI 55 PT | ARHGEF17 | Rho guanine nucleotide exchange factor (GEF) 17 | CCDS8221.1 | chr11_73020389-73020389_A_T | 236I>F | Substitution | Nonsynonymous coding | 14% | 16 | 118 |
| CGLI 55 PT | ZNF444 | zinc finger protein 444 | CCDS12939.1 | chr19_56671292-56671292_C_G | 236P>A | Substitution | Nonsynonymous coding | 14% | 4 | 71 |
| CGLI 55 PT | C10orf35 | chromosome 10 open reading frame 35 | ENST00000395055 | chr10_71390412-71390412_G_A | 7G>E | Substitution | Nonsynonymous coding | 14% | 7 | 80 |
| CGLI 55 PT | PNLIPRP2 | pancreatic lipase-related protein 2 | NM_005396 | chr10_118383462-118383462_G_A | 20E>K | Substitution | Nonsynonymous coding | 14% | 5 | 132 |
| CGLI 55 PT | CDH23 | cadherin-related 23 | NM_022124 | chr10_73544086-73544086_G_A | 1504R>Q | Substitution | Nonsynonymous coding | 14% | 18 | 147 |
| CGLI 55 PT | ACADVL | acyl-CoA dehydrogenase, very long chain | ENST00000356839 | chr17_7123259-7123259_A_C | 32S>R | Substitution | Nonsynonymous coding | 14% | 11 | 136 |
| CGLI 55 PT | LPIN2 | lipin 2 | CCDS11829.1 | chr18_2937815-2937815_G_A | 348P>L | Substitution | Nonsynonymous coding | 14% | 8 | 225 |
| CGLI 55 PT | PLEKHG5 | pleckstrin homology domain containing, family G (with RhoGef domain) member 5 | CCDS41240.1 | chr1_6529217-6529217_C_G | 799E>Q | Substitution | Nonsynonymous coding | 13% | 17 | 274 |
| CGLI 55 PT | KHDC1 | KH homology domain containing 1 | ENST00000370380 | chr6_232317402-232317402_C_A | 52T>K | Substitution | Nonsynonymous coding | 13% | 7 | 190 |
| CGLI 55 PT | AKIP1 | A kinase (PRKA) interacting protein 1 | CCDS7793.1 | chr11_6938838-6938838_A_G | 138K>R | Substitution | Nonsynonymous coding | 13% | 4 | 84 |
| CGLI 55 PT | INF2 | inverted formin, FH2 and WH2 domain containing | CCDS9989.2 | chr14_105174274-105174274_T_G | 557V>G | Substitution | Nonsynonymous coding | 13% | 4 | 14 |
| CGLI 55 PT | NUPL2 | nucleoporin like 2 | CCDS5379.1 | chr7_23221811-23221811_A_G | 36Q>R | Substitution | Nonsynonymous coding | 13% | 9 | 178 |
| CGLI 55 PT | EBLN2 | endogenous Bornavirus-like nucleoprotein 2 | NM_018029 | chr3_73111481-73111481_C_A | 83N>K | Substitution | Nonsynonymous coding | 13% | 16 | 144 |
| CGLI 55 PT | MMP12 | matrix metallopeptidase 12 (macrophage elastase) | ENST00000326227 | chr11_102738797-102738797_T_G | 210H>P | Substitution | Nonsynonymous coding | 13% | 8 | 57 |
| CGLI 55 PT | KLHL23 | kelch-like family member 23 | ENST00000404589 | chr2_170632961-170632961__AA | NA | Insertion | Frameshift | 13% | 4 | 42 |
| CGLI 55 PT | EBLN2 | endogenous Bornavirus-like nucleoprotein 2 | NM_018029 | chr3_73111480-73111480_A_C | 83N>T | Substitution | Nonsynonymous coding | 13% | 15 | 146 |
| CGLI 55 PT | CLDN7 | claudin 7 | ENST00000397317 | chr17_7165401-7165401_G_A | 8L>F | Substitution | Nonsynonymous coding | 13% | 11 | 342 |
| CGLI 55 PT | SLC9A1 | solute carrier family 9, subfamily A (NHE1, cation proton antiporter 1), member 1 | CCDS295.1 | chr1_27480818-27480818_A_C | 3L>R | Substitution | Nonsynonymous coding | 13% | 13 | 235 |
| CGLI 55 PT | SEC24D | SEC24 family, member D (S. cerevisiae) | CCDS3710.1 | chr4_119866218-119866218__A | NA | Insertion | Splice site acceptor | 13% | 5 | 19 |
| CGLI 55 PT | MUC20 | mucin 20, cell surface associated | NM_152673 | chr3_195452814-195452814_C_T | 276T>M | Substitution | Nonsynonymous coding | 12% | 29 | 369 |
| CGLI 55 PT | C8B | complement component 8, beta polypeptide | CCDS30730.1 | chr1_57420488-57420488_T_C | 135N>S | Substitution | Nonsynonymous coding | 12% | 8 | 184 |
| CGLI 55 PT | HACL1 | 2-hydroxyacyl-CoA lyase 1 | CCDS2627.1 | chr3_15613278-15613279_T__ | NA | Deletion | Splice site acceptor | 12% | 5 | 148 |

Fig. 8 (continued)

| | | | | | | | | | |
|---|---|---|---|---|---|---|---|---|---|
| CGLI 55 PT | CORIN | corin, serine peptidase | CCDS3477.1 | chr4_47746603-47746603__A | NA | Insertion | Splice site acceptor | 12% | 4 | 44 |
| CGLI 55 PT | ZNF284 | zinc finger protein 284 | CCDS46099.1 | chr19_44590002-44590002_C_T | 124S>F | Substitution | Nonsynonymous coding | 12% | 7 | 181 |
| CGLI 55 PT | C11orf40 | chromosome 11 open reading frame 40 | CCDS31354.1 | chr11_4593489-4593489_G_T | 115S>Y | Substitution | Nonsynonymous coding | 12% | 6 | 102 |
| CGLI 55 PT | PRSS3 | protease, serine, 3 | CCDS47956.1 | chr9_33797991-33797991_G_A | 179R>H | Substitution | Nonsynonymous coding | 12% | 36 | 1153 |
| CGLI 55 PT | MUC16 | mucin 16, cell surface associated | NM_024690 | chr19_8997207-8997212__AGGGAG | NA | Insertion | In-frame insertion | 12% | 5 | 62 |
| CGLI 55 PT | ROBO3 | roundabout, axon guidance receptor, homolog 3 (Drosophila) | CCDS44755.1 | chr11_124750437-124750437_C_G | 1361P>R | Substitution | Nonsynonymous coding | 12% | 7 | 19 |
| CGLI 55 PT | SLC27A3 | solute carrier family 27 (fatty acid transporter), member 3 | ENST00000368659 | chr1_153751801-153751801_G_C | 35C>S | Substitution | Nonsynonymous coding | 12% | 54 | 336 |
| CGLI 55 PT | ATG9B | autophagy related 9B | CCDS43680.1 | chr7_150713898-150713898_G_A | 767S>F | Substitution | Nonsynonymous coding | 12% | 8 | 50 |
| CGLI 55 PT | C11orf40 | chromosome 11 open reading frame 40 | CCDS31354.1 | chr11_4593487-4593487_T_A | 116I>F | Substitution | Nonsynonymous coding | 12% | 6 | 101 |
| CGLI 55 PT | TMEM37 | transmembrane protein 37 | CCDS33281.1 | chr2_120194658-120194658_G_C | 72C>S | Substitution | Nonsynonymous coding | 12% | 4 | 414 |
| CGLI 55 PT | KANK3 | KN motif and ankyrin repeat domains 3 | CCDS12199.1 | chr19_8398962-8398962_T_G | 489D>A | Substitution | Nonsynonymous coding | 12% | 6 | 97 |
| CGLI 55 PT | CDH23 | cadherin-related 23 | NM_022124 | chr10_73558952-73558952_C_T | 2380P>L | Substitution | Nonsynonymous coding | 11% | 18 | 72 |
| CGLI 55 PT | NM_00110 0111 | Uncharacterized protein | NM_001100111 | chr9_91262347-91262347_A_T | 99L>H | Substitution | Nonsynonymous coding | 11% | 5 | 62 |
| CGLI 55 PT | AFAP1L2 | actin filament associated protein 1-like 2 | ENST00000392974 | chr10_116100583-116100583_G_A | 4R>X | Substitution | Nonsense | 11% | 6 | 98 |
| CGLI 55 PT | POLDIP2 | polymerase (DNA-directed), delta interacting protein 2 | ENST00000003607 | chr17_26684404-26684404_C_G | 24A>P | Substitution | Nonsynonymous coding | 11% | 4 | 50 |
| CGLI 55 PT | CC2D2A | coiled-coil and C2 domain containing 2A | CCDS47026.1 | chr4_15513006-15513006_A_G | 226S>G | Substitution | Nonsynonymous coding | 11% | 10 | 124 |
| CGLI 55 PT | LRRC17 | leucine rich repeat containing 17 | CCDS34721.1 | chr7_102575000-102575000_G_A | 214E>K | Substitution | Nonsynonymous coding | 11% | 13 | 167 |
| CGLI 55 PT | CRIPAK | cysteine-rich PAK1 inhibitor | CCDS3349.1 | chr4_1388376-1388376__CA | NA | Insertion | Frameshift | 11% | 15 | 83 |
| CGLI 55 PT | PRSS3 | protease, serine, 3 | CCDS47956.1 | chr9_33797828-33797828_C_T | 125R>C | Substitution | Nonsynonymous coding | 11% | 23 | 486 |
| CGLI 55 PT | ZAN | zonadhesin | ENST00000419283 | chr7_100386563-100386597_CTTCAGCTACCGCT TGCAAGGCCGCATGACCTATG_ | NA | Deletion | Frameshift | 11% | 11 | 171 |
| CGLI 55 PT | EVI5 | ecotropic viral integration site 5 | CCDS30774.1 | chr1_93070934-93070934_C_T | 651R>K | Substitution | Nonsynonymous coding | 11% | 9 | 262 |
| CGLI 55 PT | FRS2 | fibroblast growth factor receptor substrate 2 | CCDS41809.1 | chr12_69968154-69968154_A_C | 316S>R | Substitution | Nonsynonymous coding | 11% | 6 | 182 |
| CGLI 55 PT | SH3D21 | SH3 domain containing 21 | NM_00162530 | chr1_36773761-36773761_C_G | 197P>R | Substitution | Nonsynonymous coding | 11% | 6 | 167 |
| CGLI 55 PT | OR2T4 | Olfactory receptor 2T4;OR2T4;ortholog | CCDS31113.1 | chr1_248525329-248525329__TA | T149S | Insertion | frameshift insertion | 10% | 27 | 63 |
| CGLI 55 PT | B4GALT2 | UDP-Gal:betaGlcNAc beta 1,4-galactosyltransferase, polypeptide 2 | CCDS506.1 | chr1_44450686-44450686_A_C | 233Q>H | Substitution | Nonsynonymous coding | 10% | 5 | 97 |
| CGLI 55 PT | HRNR | Hornerin;HRNR;ortholog | CCDS30859.1 | chr1_152186837-152186837_C_T | R2423Q | Substitution | nonsynonymous SNV | 10% | 75 | 83 |
| CGLI 55 PT | EBLN2 | endogenous Bornavirus-like nucleoprotein 2 | NM_018029 | chr3_73111503-73111503_T_G | 91L>V | Substitution | Nonsynonymous coding | 10% | 15 | 154 |
| CGLI 55 PT | FRS2 | fibroblast growth factor receptor substrate 2 | CCDS41809.1 | chr12_69968151-69968151_C_G | 315P>A | Substitution | Nonsynonymous coding | 10% | 6 | 185 |
| CGLI 55 PT | UNC93B1 | unc-93 homolog B1 (C. elegans) | ENST00000227471 | chr11_67765159-67765159_A_G | 237L>P | Substitution | Nonsynonymous coding | 10% | 4 | 394 |
| CGLI 55 PT | ZP3 | zona pellucida glycoprotein 3 (sperm receptor) | CCDS47616.1 | chr7_76069926-76069926_A_G | 353H>R | Substitution | Nonsynonymous coding | 10% | 13 | 156 |
| CGLI 55 PT | SZT2 | seizure threshold 2 homolog (mouse) | CCDS30894.1 | chr1_43896428-43896428_C_T | 802S>L | Substitution | Nonsynonymous coding | 10% | 10 | 426 |
| CGLI 55 PT | CYP4F8 | cytochrome P450, family 4, subfamily F, polypeptide 8 | ENST00000441682 | chr19_15730502-15730502_C_A | 151T>K | Substitution | Nonsynonymous coding | 10% | 11 | 236 |
| CGLI 55 PT | FRG2C | Protein FRG2-like-2;FRG2C;ortholog | CCDS43108.1 | chr3_75714923-75714923_G_C | V194L | Substitution | nonsynonymous SNV | 10% | 17 | 34 |
| CGLI 55 PT | EMX2 | empty spiracles homeobox 2 | CCDS7601.1 | chr10_119302792-119302792_C_T | 5A>V | Substitution | Nonsynonymous coding | 10% | 6 | 178 |
| CGLI 55 PT | ASPHD1 | Aspartate beta-hydroxylase domain-containing protein 1;ASPHD1;ortholog | CCDS10660.1 | chr16_29912802-29912802__GGG | Q170delins QG | Insertion | nonframeshift insertion | 10% | 10 | 63 |
| CGLI 55 PT | VCX | Variable charge X-linked protein 1;VCX;ortholog | CCDS14128.1 | chrX_7811971-7811971_G_C | E179Q | Substitution | nonsynonymous SNV | 8% | 12 | 34 |
| CGLI 55 PT | HRNR | Hornerin;HRNR;ortholog | CCDS30859.1 | chr1_152187827-152187827_C_G | R2423Q | Substitution | nonsynonymous SNV | 7% | 12 | 63 |
| CGLI 55 PT | OR5L1 | Olfactory receptor 5L1;OR5L1;ortholog | CCDS31509.1 | chr11_55579146-55579146_C_T | S68F | Substitution | nonsynonymous SNV | 7% | 12 | 34 |
| CGLI 55 PT | SYNPO2 | Synaptopodin-2;SYNPO2;ortholog | CCDS34054.1 | chr4_119947966-119947966_A_T | R147S | Substitution | nonsynonymous SNV | 7% | 6 | 63 |
| CGLI 55 PT | SYNPO2 | Synaptopodin-2;SYNPO2;ortholog | CCDS34054.1 | chr4_119947966-119947966_A_G | R147S | Substitution | nonsynonymous SNV | 5% | 6 | 63 |
| CGLI 56 PT | PRDM15 | PR domain containing 15 | CCDS13676.1 | chr21_43243793-43243793_G_A | 914R>W | Substitution | Nonsynonymous coding | 52% | 22 | 45 |
| CGLI 56 PT | AQR | aquarius homolog (mouse) | CCDS42013.1 | chr15_35198828-35198828_A_ | NA | Deletion | Frameshift | 39% | 41 | 169 |

Fig. 8 (continued)

| Sample | Gene | Description | Transcript | Location | Change | Type | Effect | % | Reads1 | Reads2 |
|---|---|---|---|---|---|---|---|---|---|---|
| CGLI 56 PT | MLLT6 | myeloid/lymphoid or mixed-lineage leukemia (trithorax homolog, Drosophila); translocated to, 6 | CCDS11327.1 | chr17_36863737-36863737_A_G | NA | Substitution | Splice site acceptor | 28% | 82 | 227 |
| CGLI 56 PT | TTC14 | tetratricopeptide repeat domain 14 | CCDS3237.1 | chr3_180321031-180321031_A_G | 136I>V | Substitution | Nonsynonymous coding | 11% | 7 | 94 |
| CGLI 58 PT | CDH11 | cadherin 11, type 2, OB-cadherin (osteoblast) | ENST00000394156 | chr16_64982664-64982664_A_C | 641S>A | Substitution | Nonsynonymous coding | 30% | 9 | 63 |
| CGLI 58 PT | CD177P1 | CD177 molecule pseudogene 1 | ENST00000378097 | chr19_43882895-43882895_A_G | 58V>G | Substitution | Nonsynonymous coding | 28% | 5 | 20 |
| CGLI 58 PT | HPS6 | Hermansky-Pudlak syndrome 6 | CCDS7527.1 | chr10_103828243-103828243_G_A | 338G>S | Substitution | Nonsynonymous coding | 26% | 55 | 29 |
| CGLI 58 PT | ADCK2 | aarF domain containing kinase 2 | CCDS5861.1 | chr7_140374534-140374534_T_A | 353F>I | Substitution | Nonsynonymous coding | 23% | 21 | 197 |
| CGLI 58 PT | LGI2 | leucine-rich repeat LGI family, member 2 | CCDS3431.1 | chr4_25032262-25032264_CAG_ | NA | Deletion | In-frame deletion | 11% | 4 | 21 |
| CGLI 58 PT | MSRB3 | methionine sulfoxide reductase B3 | CCDS8973.1 | chr12_65847577-65847577_T_C | 128M>T | Substitution | Nonsynonymous coding | 11% | 15 | 109 |
| CGLI 60 PT | CTDNEP1 | CTD nuclear envelope phosphatase 1 | CCDS11093.1 | chr17_7149679-7149679_C_T | 124W>X | Substitution | Nonsense | 91% | 10 | 27 |
| CGLI 60 PT | KAT6A | K(lysine) acetyltransferase 6A | CCDS6124.1 | chr8_41791092-41791092_C_T | 1549G>D | Substitution | Nonsynonymous coding | 52% | 134 | 327 |
| CGLI 60 PT | LMO7 | LIM domain 7 | CCDS9454.1 | chr13_76408508-76408508_C_T | 789R>C | Substitution | Nonsynonymous coding | 45% | 19 | 95 |
| CGLI 60 PT | VPS28 | vacuolar protein sorting 28 homolog (S. cerevisiae) | CCDS34967.1 | chr8_145652300-145652300_C_T | 10G>D | Substitution | Nonsynonymous coding | 44% | 107 | 256 |
| CGLI 60 PT | PDE7B | phosphodiesterase 7B | ENST00000446774 | chr6_136477014-136477014_C_T | 171T>M | Substitution | Nonsynonymous coding | 43% | 29 | 102 |
| CGLI 60 PT | CASP10 | caspase 10, apoptosis-related cysteine peptidase | CCDS2338.1 | chr2_202093659-202093659_G_A | 473M>I | Substitution | Nonsynonymous coding | 42% | 20 | 94 |
| CGLI 60 PT | MTMR4 | myotubularin related protein 4 | CCDS11608.1 | chr17_56573393-56573393_G_C | 704L>V | Substitution | Nonsynonymous coding | 40% | 50 | 122 |
| CGLI 60 PT | ZNF358 | zinc finger protein 358 | CCDS32890.2 | chr19_7584331-7584331_C_T | 68S>L | Substitution | Nonsynonymous coding | 38% | 116 | 443 |
| CGLI 60 PT | TMPRSS15 | transmembrane protease, serine 15 | CCDS13571.1 | chr21_19666748-19666748__T | NA | Insertion | Frameshift | 33% | 16 | 104 |
| CGLI 60 PT | SLC9A3 | solute carrier family 9, subfamily A (NHE3, cation proton antiporter 3), member 3 | CCDS3855.1 | chr5_485275-485275_C_A | 249K>N | Substitution | Nonsynonymous coding | 32% | 53 | 220 |
| CGLI 60 PT | LY9 | lymphocyte antigen 9 | CCDS30917.1 | chr1_160771693-160771693_G_A | 190V>M | Substitution | Nonsynonymous coding | 30% | 28 | 123 |
| CGLI 60 PT | MCMDC2 | minichromosome maintenance domain containing 2 | CCDS6197.2 | chr8_67803275-67803275__A | NA | Insertion | Frameshift | 29% | 16 | 70 |
| CGLI 60 PT | SOX3 | SRY (sex determining region Y)-box 3 | CCDS14689.1 | chrX_139586896-139586896_C_A | 177W>L | Substitution | Nonsynonymous coding | 26% | 16 | 172 |
| CGLI 60 PT | GPAT2 | glycerol-3-phosphate acyltransferase 2, mitochondrial | CCDS42714.1 | chr2_96697827-96697827_C_T | 44R>H | Substitution | Nonsynonymous coding | 22% | 10 | 81 |
| CGLI 60 PT | VPS13C | vacuolar protein sorting 13 homolog C (S. cerevisiae) | CCDS32257.1 | chr15_62170831-62170831_T_C | 3373T>A | Substitution | Nonsynonymous coding | 19% | 11 | 123 |
| CGLI 61 PT | FAM118A | family with sequence similarity 118, member A | ENST00000405873 | chr22_45724286-45724286_C_G | 173A>G | Substitution | Nonsynonymous coding | 25% | 5 | 20 |
| CGLI 61 PT | MLH1 | mutL homolog 1, colon cancer, nonpolyposis type 2 (E. coli) | CCDS2663.1 | chr3_37092077-37092077_C_A | 735T>K | Substitution | Nonsynonymous coding | 21% | 20 | 24 |
| CGLI 61 PT | TENM2 | teneurin transmembrane protein 2 | NM_001122679 | chr5_167379879-167379879_G_A | 267A>T | Substitution | Nonsynonymous coding | 21% | 45 | 220 |
| CGLI 63 PT | DDX3X | DEAD (Asp-Glu-Ala-Asp) box polypeptide 3, X-linked | CCDS43931.1 | chrX_41203535-41203535_G_T | 303G>V | Substitution | Nonsynonymous coding | 77% | 37 | 34 |
| CGLI 63 PT | PTCH1 | patched 1 | CCDS6714.1 | chr9_98244230-98244230_C_A | NA | Substitution | Splice site donor | 71% | 47 | 91 |
| CGLI 63 PT | STUB1 | STIP1 homology and U-box containing protein 1, E3 ubiquitin protein ligase | CCDS10419.1 | chr16_732485-732485_A_G | 303Y>C | Substitution | Nonsynonymous coding | 49% | 88 | 198 |
| CGLI 63 PT | C5orf48 | chromosome 5 open reading frame 48 | CCDS4139.1 | chr5_125971922-125971922_C_T | 132R>X | Substitution | Nonsense | 46% | 16 | 34 |
| CGLI 63 PT | KCNA4 | potassium voltage-gated channel, shaker-related subfamily, member 4 | CCDS41629.1 | chr11_30033961-30033961_G_A | 89R>W | Substitution | Nonsynonymous coding | 45% | 59 | 137 |
| CGLI 63 PT | PUM2 | pumilio homolog 2 (Drosophila) | CCDS1698.1 | chr2_20512073-20512073_C_A | 91G>V | Substitution | Nonsynonymous coding | 45% | 41 | 77 |
| CGLI 63 PT | CDH8 | cadherin 8, type 2 | CCDS10802.1 | chr16_61851479-61851479_C_T | 394P>L | Substitution | Nonsynonymous coding | 44% | 42 | 72 |
| CGLI 63 PT | CBLB | Cbl proto-oncogene, E3 ubiquitin protein ligase B | CCDS2948.1 | chr3_105495364-105495364_C_T | 141R>Q | Substitution | Nonsynonymous coding | 44% | 45 | 52 |
| CGLI 63 PT | NMBR | neuromedin B receptor | CCDS5196.1 | chr6_142409630-142409630_C_T | 56V>M | Substitution | Nonsynonymous coding | 43% | 142 | 336 |
| CGLI 63 PT | OCLN | occludin | CCDS4096.1 | chr5_68809848-68809848_G_A | 268R>Q | Substitution | Nonsynonymous coding | 43% | 39 | 74 |
| CGLI 63 PT | MAP4 | microtubule-associated protein 4 | ENST00000320796 | chr3_47933674-47933674_T_C | 103H>R | Substitution | Nonsynonymous coding | 43% | 79 | 84 |
| CGLI 63 PT | BTBD17 | BTB (POZ) domain containing 17 | CCDS32719.1 | chr17_72353773-72353773_C_T | 154V>M | Substitution | Nonsynonymous coding | 43% | 41 | 130 |
| CGLI 63 PT | C2orf88 | chromosome 2 open reading frame 88 | CCDS42792.1 | chr2_191064777-191064777_G_A | 64R>H | Substitution | Nonsynonymous coding | 41% | 45 | 85 |

Fig. 8 (continued)

| Sample | Gene | Description | Accession | Genomic coordinates | AA change | Type | Effect | Freq | Var reads | Total reads |
|---|---|---|---|---|---|---|---|---|---|---|
| CGLI 63 PT | ACSM1 | acyl-CoA synthetase medium-chain family member 1 | CCDS10587.1 | chr16_20702489-20702489_G_A | 8R>W | Substitution | Nonsynonymous coding | 41% | 19 | 48 |
| CGLI 63 PT | IGSF22 | immunoglobulin superfamily, member 22 | CCDS41625.1 | chr11_18736991-18736991_C_T | 507V>I | Substitution | Nonsynonymous coding | 38% | 30 | 48 |
| CGLI 63 PT | STT3A | STT3, subunit of the oligosaccharyltransferase complex, homolog A (S. cerevisiae) | CCDS8458.1 | chr11_125482502-125482502_G_A | 409V>M | Substitution | Nonsynonymous coding | 38% | 26 | 37 |
| CGLI 63 PT | RFWD3 | ring finger and WD repeat domain 3 | CCDS32486.1 | chr16_74694855-74694855_C_T | 165G>R | Substitution | Nonsynonymous coding | 38% | 45 | 111 |
| CGLI 63 PT | MYO15A | myosin XVA | CCDS42271.1 | chr17_18024242-18024242_G_A | 710V>M | Substitution | Nonsynonymous coding | 31% | 5 | 49 |
| CGLI 63 PT | MFSD6 | major facilitator superfamily domain containing 6 | CCDS2306.1 | chr2_191300931-191300931_A_C | 59K>T | Substitution | Nonsynonymous coding | 14% | 21 | 80 |
| CGLI 254 PT | KDM6A | lysine (K)-specific demethylase 6A | CCDS14265.1 | chrX_44864415_44864415_C_T | 1385 Q>X | Substitution | Nonsense | 82% | 26 | 54 |
| CGLI 254 PT | ACTRT2 | protease, serine, 16 (thymus) | CCDS4623.1 | chr6_27327725_27327725_G_A | 312 C>Y | Substitution | Nonsynonymous coding | 43% | 224 | 429 |
| CGLI 254 PT | PRDM16 | DAVID_YY1 associated protein 1; gon-4-like (C. elegans) | NM_0010375 33 | chr1_153999838_153999838_G_C | 1539 Q>E | Substitution | Nonsynonymous coding | 5% | 27 | 534 |
| CGLI 254 PT | NOL9 | actin filament associated protein 1-like 2 | CCDS31266.1 | chr10_119050190_119050190_G_T | NA | Substitution | Splice site donor | 5% | 15 | 251 |
| CGLI 254 PT | UBE4B | zinc finger protein 195 | CCDS41604.1 | chr11_3338375_3338375__A | NA | insertion | Splice site acceptor | 15% | 11 | 106 |
| CGLI 254 PT | PRAMEF1 | immunoglobulin heavy constant alpha 2 (A2m marker) | ENST000003 90538 | chr14_105125613_105125613_A_G | 55 L>P | Substitution | Nonsynonymous coding | 9% | 16 | 171 |
| CGLI 254 PT | PRAMEF1 | immunoglobulin heavy constant alpha 2 (A2m marker) | ENST000003 90538 | chr14_105125638_105125638_T_C | 47 T>A | Substitution | Nonsynonymous coding | 8% | 15 | 185 |
| CGLI 254 PT | PRAMEF4 | immunoglobulin heavy constant alpha 2 (A2m marker) | ENST000003 90538 | chr14_105125639_105125639_T_C | 46 R>R | Substitution | Nonsynonymous coding | 7% | 15 | 195 |
| CGLI 254 PT | LOC64535 9 | xeroderma pigmentosum, complementation group C | ENST000002 85021 | chr3_14175042_14175042_G_T | NA | Substitution | Splice site donor | 6% | 25 | 417 |
| CGLI 254 PT | PRAMEF4 | DAVID_leucine rich repeat containing 70 | NM_181506 | chr5_61911467_61911467_A_G | 149 R>G | Substitution | Nonsynonymous coding | 14% | 14 | 101 |

Genomic coordinates refer to the human reference genome hg19 release (Genome Reference Consortium GRCh37, Feb 2009)

DETECTION OF TUMOR-DERIVED DNA IN CEREBROSPINAL FLUID

This application is a National Stage application under 35 U.S.C. § 371 of International Application No. PCT/US2016/041862, having an International Filing Date of Jul. 12, 2016, which claims the benefit of U.S. Provisional Application No. 62/192,424, filed on Jul. 14, 2015, each of which is incorporated by reference in its entirety.

This invention was made with government support under grant CA043460 awarded by the National Institutes of Health. The government has certain rights in the invention.

TECHNICAL FIELD OF THE INVENTION

This invention is related to the area of nucleic acid assays. In particular, it relates to assays of small amounts of nucleic acid in body fluids.

BACKGROUND OF THE INVENTION

Approximately 25,000 individuals each year are diagnosed with a malignant brain or spinal cord tumor in the United States and more than half of these patients will die from their disease (1). While there are a number of different subtypes of primary central nervous system (CNS) cancers, nearly all are treated with maximal safe surgical resection followed by radiation and, in some cases, chemotherapy. Given the lack of clinically available biomarkers for CNS malignancies, the conventional method for disease monitoring in these patients is radiographic, using either computed tomography (CT) or magnetic resonance imaging (MRI) (2). Unfortunately, anatomic changes detected by these imaging modalities are often non-specific and slow to change even in the face of progressing or regressing disease. Moreover, it can be difficult to discriminate between treatment effect and cancer growth with imaging alone (3). Patients must, therefore, have additional surgeries for definitive tissue diagnosis or inappropriately wait for radiographic findings to change as their disease progresses. As a result, there is a great need for more sensitive and specific tumor biomarkers in neuro-oncology. The recent success of detecting circulating tumor cells (CTC's) in the peripheral blood of glioblastoma patients represents an important step towards this goal, with reported sensitivities between 21% and 39% (4-6). Circulating tumor-derived DNA (ctDNA) is found in the plasma of patients with most forms of malignancies (7-11). However, brain tumors, including high-grade gliomas and medulloblastomas, are an exception, with only a minority giving rise to detectable levels of ctDNA, perhaps because of the blood-brain barrier (8).

There is a continuing need in the art to develop sensitive assays for difficult-to-detect analytes.

SUMMARY OF THE INVENTION

According to one aspect of the invention a method is provided. Nucleic acids in a Cerebral Spinal Fluid (CSF) sample from a human with a central nervous system (CNS) cancer are assayed for one or more mutations in the nucleic acids. The mutations are present in the cancer but not in normal tissues of the human.

Another aspect of the invention is a method in which nucleic acids in a CNS cancer tissue of a human are assayed, and one or more mutations are determined. Nucleic acids in a normal tissue of the human are also assayed, and absence of the one or more mutations is determined. Nucleic acids in a Cerebral Spinal Fluid (CSF) sample from the human are assayed for the one or more mutations in the sample using a specific probe or specific primer to detect the one or more mutations. The specific probe or specific primer hybridizes at or within 200 nucleotides of the mutation.

These and other embodiments which will be apparent to those of skill in the art upon reading the specification provide the art with

BRIEF DESCRIPTION OF THE DRAWINGS

(FIG. 2A) Example of tumor (red arrow) abutting a CSF space is shown. (FIG. 2B) Example of tumor not in contact with a CSF space is shown. Corresponding T2 images are provided for easier visualization of CSF.

FIG. 3 (Table 1). Patient Demographics

FIG. 4 (Table 2). Mutations detected in the CSF and tumor of each patient

FIG. 5A-5B (Tables 3A-3B). FIG. 5A. Associations between clinical characteristics and levels of CSF-tDNA. FIG. 5B. Associations between clinical characteristic and levels of CSF-tDNA.

FIG. 6 (Table 4). Detection of CSF-tDNA using whole—exome sequencing (WWS)

Figure 7:
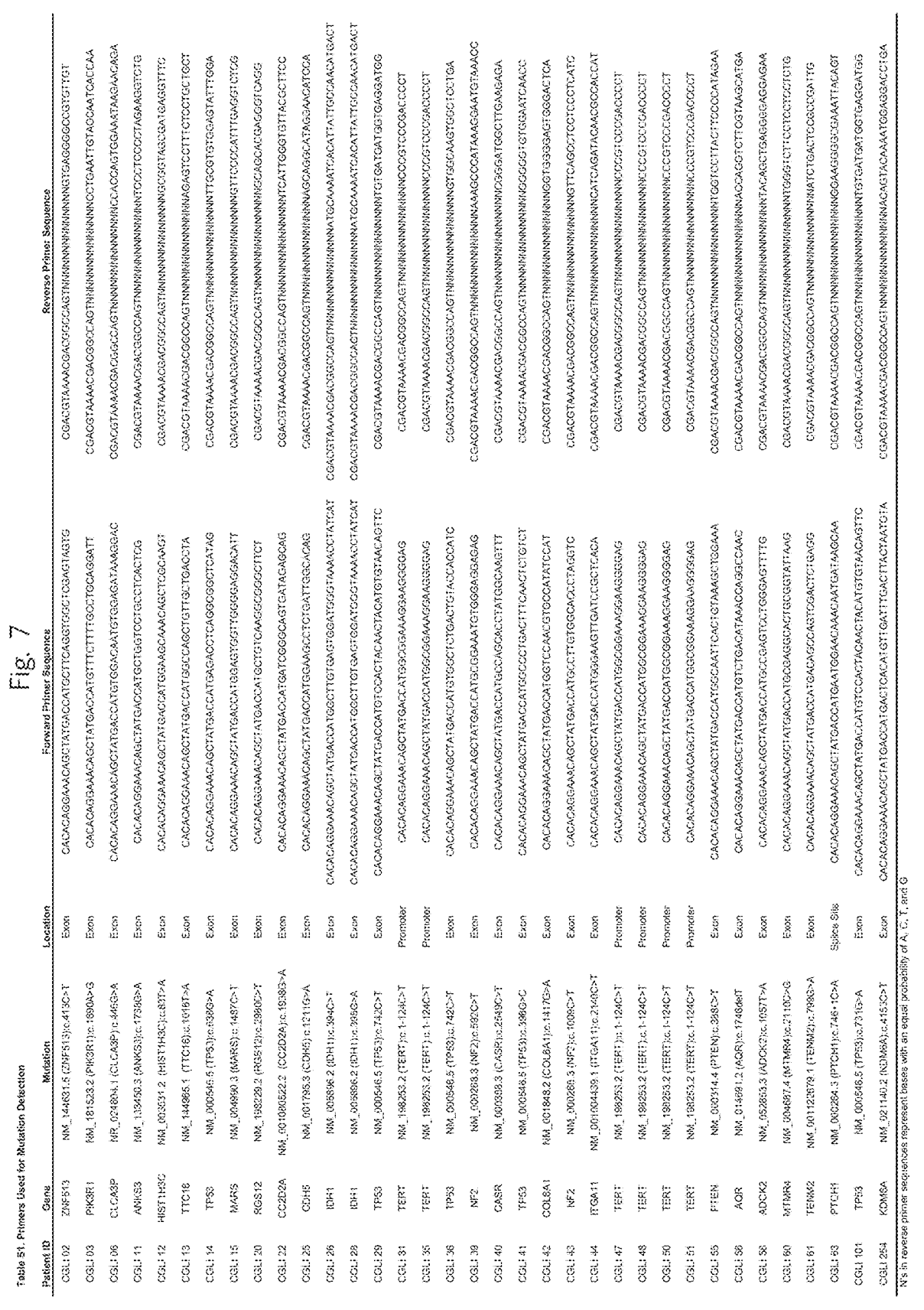

FIG. 7 (Table S1). Primers used for Mutations Detection. Forward primers (SEQ ID NO: 1-35). Reverse Primers (SEQ ID NO: 36-70).

FIG. 8 (Table S1). Mutations identified in whole-exome sequencing

Figure 1:
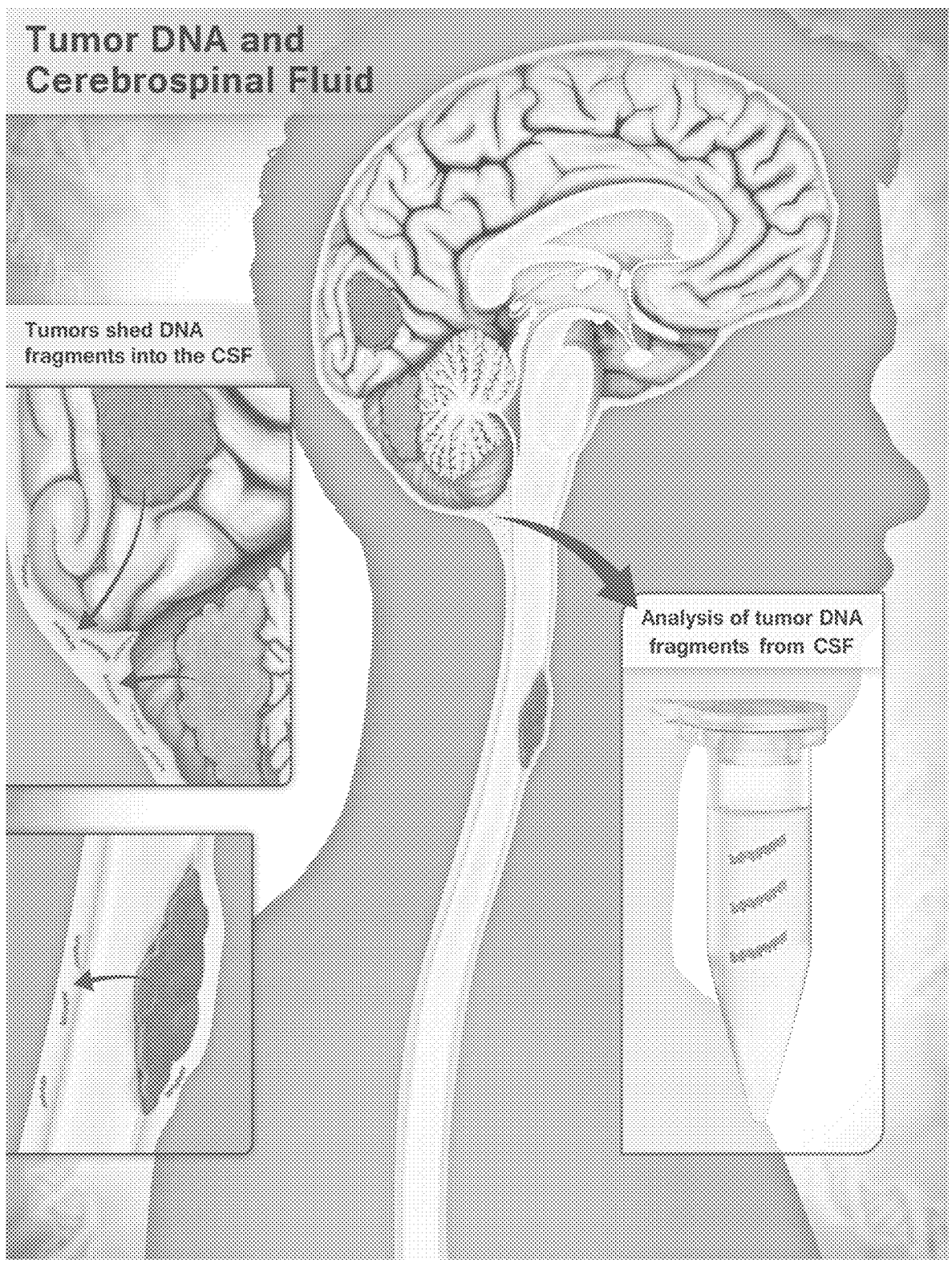
FIG. 1. Schematic showing the shedding of CSF-tDNA from Central Nervous System (CNS) malignancies. Tumor cells from primary brain and spinal cord tumors shed DNA into the cerebrospinal fluid (CSF) that bathes the CNS. DNA purified from the CSF is analyzed for tumor-specific mutations.
Figure 2A:
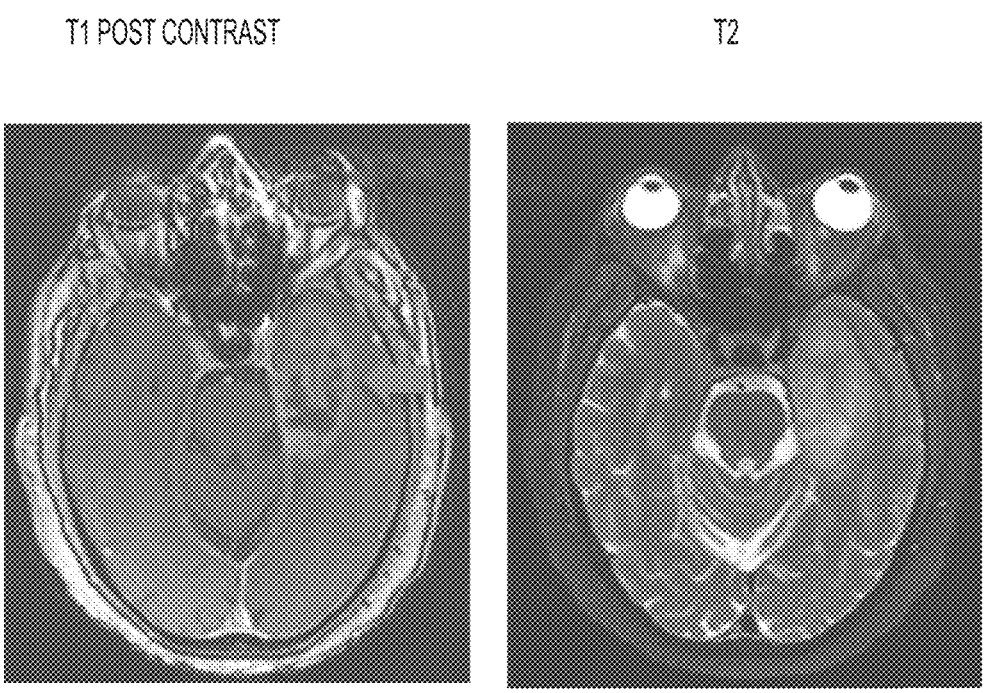
FIGS. 2A-2B. Representative MR images.
Figure 2B:
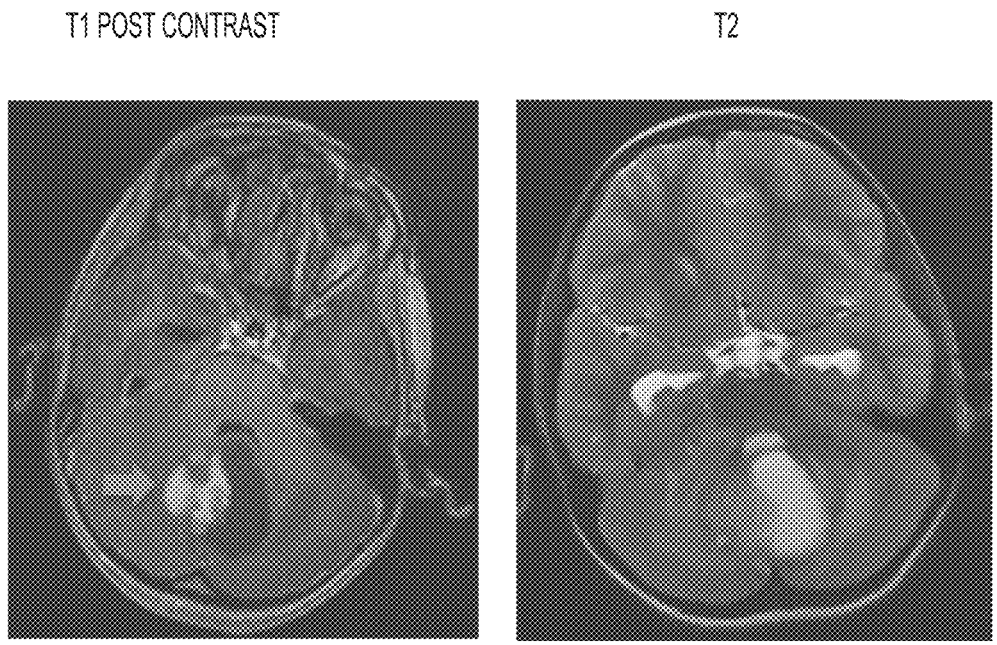

A sequence listing is included as part of this application.

DETAILED DESCRIPTION OF THE INVENTION

The inventors have developed a way to avoid invasive surgical procedures to determine disease status and/or to avoid treatment delays when radiographic testing fails to show disease progression. Detection of tumor-specific DNA shed from primary CNS tumors into the surrounding cerebrospinal fluid (CSF-tDNA), can serve as a sensitive and exquisitely specific marker for quantifying tumor burden without invasive biopsies.

CNS tumors which can be assessed include those of the brain and spinal cord. As discussed below, those tumors which are located close to a ventricle or cortical surface are preferred. Suitable tumors for assessment include without limitation primary and malignant tumors of the brain and spinal cord, including pilocytic astrocytoma, diffuse astrocytoma/low-grade astrocytoma, anaplastic astrocytoma, glioblastomas (also called glioblastoma multiforme, gbm, or grade iv astrocytoma), brain stem gliomas, ependymomas, oligodendrogliomas, mixed gliomas, meningiomas, pituitary tumors, craniopharyngiomas, germ cell tumors, pineal region tumors, medulloblastomas, and primary CNS lymphomas.

Cerebral spinal fluid can be accessed by any practical means. It can be collected during surgery. It can be collected from an intracranial space, e.g., a space created during and remaining after surgery. It can be collected via lumbar puncture or cisternal puncture. It can be collected using an implanted reservoir, such as an Ommaya reservoir.

While mutations that are detected in the CSF may be previously tested and confirmed in tumor tissue and normal tissue, this may not always be necessary. For example, certain mutations by their prevalence and or location may be presumed to be mutations. In some cases it may be preferred to identify a mutation in tumor tissue prior to assessing it in CSF. In other cases direct detection may be used. When a mutation has been identified in tumor tissue in advance, more targeted assessments can be used, for example, using mutation specific or mutation targeted probes or primers. When a mutation has not been previously identified in tumor tissue, broader screening techniques can be used.

Targeted reagents for assessment of particular mutations will typically be probes or primers. These nucleic acid reagents may optionally contain tags, including unique tags. These nucleic acid reagents may optionally contain labels, such as radionuclides, chromophores, binding sites for binding partners. The reagents may contain nucleic acid modifications that render the reagents more stable, for example. The probes and primers will typically be between 10 and 100 bases, and may be supplied as either double stranded or single stranded molecules. The probes and primers may hybridize to either the strand of the genomic DNA, coding or non-coding. Typically primers will hybridize to opposite strands of the genomic DNA. Desirably the probes and primers will be within 1 kbp, within 500 bp, within 250 bp, within 200 bp, within 100 bp, or within 50 bp of the mutation which is being assessed. Primers can be used in amplification reactions of various sorts. Optionally, amplification can be done using nested primers.

In order to ascertain whether the tumor is located near a ventricle or cortical surface, any type of imaging known in the art can be used. These include without limitation, magnetic resonance imaging, computed tomography, X-rays, positron emission tomography (PET), functional magnetic resonance imaging (fMRI), and angiography.

In many cases surgery will be the first or one of the first treatments for a CNS tumor. The assessment of CSF in those cases will typically be performed after surgery. However, it may be desirable to assess the CSF even before surgery. In cases where surgery is not indicated, CSF can be assessed directly. The CSF may be assessed at multiple time points during or following a therapy.

Assessment of CSF nucleic acids may be useful in many different contexts. It can be useful for monitoring disease burden. It may be useful for distinguishing neoplastic from non-neoplastic processes. It can be useful for follow-up to a radiological finding.

Minimally invasive techniques to monitor disease burden have been a challenge for nearly all diseases of the CNS, including cancer. This challenge is highlighted by the high risks associated with neurosurgical procedures and the widely recognized limitations of current imaging modalities. In cancer patients, there is no reliable way of parsing out treatment effects from tumor recurrence, causing many patients to undergo unnecessary repeat surgeries. For example, in approximately 30% of patients with glioblastoma who undergo a repeat resection for presumptive recurrence, pathologic examination of the resected specimen reveals necrosis, scarring or other treatment-related effects rather than recurrent disease (20). Conversely, while patients are waiting for or recovering from surgery, chemotherapy or radiation therapy cannot be administered, providing time for unabated tumor growth. Finally, patients are often kept on ineffective medication regimens until definitive signs of tumor progression appear on imaging. This delay in detection precludes potential opportunities to undergo new targeted therapies that might be effective for their disease (21). The health costs of these missed opportunities will increase with the expected advances in therapeutic modalities.

Given the need for sensitive and specific markers to monitor tumor dynamics, we asked whether tumor-derived DNA could be found in the cerebrospinal fluid of patients with primary CNS tumors. This study was stimulated by our inability to frequently detect tumor DNA in the plasma of these patients (8) and inspired by previous demonstrations that tumor-derived DNA could be found in fluids located in the proximity of neoplastic lesions. For example, a recent pilot study by Pan et al suggests that tumor-derived DNA can be detected in the spinal fluid of individuals whose primary tumors have metastasized to the brain (22). Though lumbar puncture to obtain CSF is not a non-invasive procedure, it qualifies as minimally invasive and is currently routinely performed to follow some brain tumor patients, particularly those with medulloblastomas (23, 24). Unfortunately, the examination of these CSF samples by cytology is usually of limited utility (25, 26). Only one of the 35 patients evaluated in the current study had concomitant cytologic studies of CSF, precluding direct comparison. The results of this study suggest that the rates of tumor-derived DNA found in the CSF (74%) closely approximate the levels found in body fluids adjacent to other tumor types. For example, urine in bladder cancer was found to have tumor derived DNA in 70% of cases, while sputum in lung cancer was positive in 79% of cases (27, 28). While the rate of detection observed in the current study was not 100%, its sensitivity was comparable or superior to other non-invasive tests for malignancies in general. Moreover, and as noted below, it was particularly sensitive for tumors that abutted a CSF reservoir or cortical surface. Finally, from a technological standpoint, the average fraction of mutant DNA (12.2%) far exceeded the limit of detection of the sequencing assay used (0.01%). This assay could be performed with any commercially available next-generation sequencing instrument, at relatively small cost.

Our study revealed a significant association between the location and type of the tumor with the presence of CSF-tDNA. In particular, we were able to detect all thirteen WHO Grade III or Grade IV gliomas (also known as anaplastic astrocytoma and glioblastoma, respectively), all five medulloblastomas and all three ependymomas that abutted a CSF reservoir or cortical surface. It is in these aggressive tumors where the need for a robust biomarker is most desperately needed. There are also emerging data that some brain tumors, particularly those with genotypes susceptible to targeted therapies, may be able to be treated primarily with medical therapies, thereby obviating the need for surgery if appropriate non-invasive diagnostic tools were available (29-32). It is also worth noting that surgical resection nearly always creates an opening extending from the surface to the deep-seated tumor. This passageway typically persists and may enable tumor-derived DNA from any residual or recurrent tumor to enter the CSF. Even without such surgically-induced openings, the vast majority of medulloblastomas and ependymomas arise within or communicate with a ventricular reservoir, making them well-suited for CSF monitoring. Indeed, these are currently the most common tumor types in which CSF cytology is a part of routine clinical practice (24, 33). Future studies will be required to directly compare CSF-tDNA and CSF cytology. However, despite being the standard of care, CSF cytology has reported sensitivities below 50% and often requires a large volume of CSF for analysis (>10 ml) (34). Rather than replacing cytology, we envision that CSF-tDNA will be used in combination with it and other biomarkers under development, as well as with radiographic and clinical parameters, to substantially increase the accuracy of tumor burden estimates post-surgically (35-38).

Given the invasive and risky nature of surgical interventions on the brain and spinal cord, it would be useful to be able to identify a neoplastic process without performing surgery. Our results provide a glimpse of the potential for this form of diagnosis in the future. We evaluated four patients, one with a tumor in the midbrain, one in the pons, and two in the spinal cord. Using WES, we were able to detect CSF-tDNA in two of the four cases by comparing the data to that obtained by targeted sequencing with SafeSeqS. The results were consistent with expectation in that the mutant fractions revealed by genome-wide sequencing were in accord with those identified by targeted sequencing (Table 4). Additional cases will need to be tested in order to elucidate the potential of this approach in patients in whom biopsies are challenging, but our results show that genome-wide analysis of the DNA from CSF is feasible in at least some cases.

While the results described above are promising, we caution that this is an exploratory study designed primarily to determine whether it was possible to detect CSF-tDNA in patients with primary CNS tumors. A secondary goal was to document the anatomical and pathologic characteristics of the tumors that shed DNA into the CSF. The most important technical limitation of our study is that CSF samples were obtained at the time of surgery, often from the ventricles, rather than from a lumbar puncture. CSF has been demonstrated to quickly circulate throughout the ventricles and spinal reservoirs (39, 40), It is therefore very likely that the DNA in the spinal fluid obtained via lumbar puncture will be similar to that of the ventricles, even though the fluid obtained from lumbar puncture is farther away from the site of malignancy. An additional consideration is that in individuals with a bulky mass that obstructs spinal fluid flow or elevates intracranial pressure, a lumbar puncture might be unsafe. However, these patients will almost always require surgical decompression to reduce the mass effect generated by the tumor and CSF could be safely obtained after opening the dura. The exact method and location of CSF sampling in patients with CNS neoplasms will need to be individualized and will be based on a number of factors, including tumor location, ease of CSF sampling and clinical characteristics. For example, patients may initially undergo CSF sampling from an intracranial space at the time of surgery to determine baseline levels of CSF-tDNA but lumbar punctures could be used to longitudinally monitor CSF-tDNA levels.

Now that it has been documented that most primary brain tumors release tumor DNA into the CSF, the stage is set for a longitudinal study of the clinical utility of this new biomarker. Our results suggest specific guidelines for such a follow-up study. The optimal patients to follow would be those with medulloblastomas, ependymomas, or high-grade gliomas that abut a CSF space, as the CSF-tDNA assay is particularly sensitive in such cases and these tumor types are relatively common. CSF-tDNA should be evaluated intra-operatively to establish a baseline, and a concomitant lumbar puncture should be performed when possible to ensure concordance between the two fluid samples. Subsequent evaluations of CSF obtained through lumbar puncture or an implanted reservoir should be compared to other clinical and laboratory features, with the goal of determining the utility of CSF-tDNA to detect minimal residual disease. For example, patients whose mass persists upon MRI but whose CSF-tDNA is undetectable might be spared a second biopsy. Alternatively, patients in whom residual disease is evident upon CSF-tDNA analysis, but is equivocal upon imaging analysis, might be well-served by additional therapy. In the future, it is likely that most brain tumors will be routinely assessed for mutations in various genes of interest, both for prognostic and therapeutic purposes (41-43). The availability of such sequencing data should make the approach described here more cost-effective and easier to implement.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

We analyzed 35 primary CNS malignancies and found at least one mutation in each tumor using targeted or genome-wide sequencing. Using these patient-specific mutations as biomarkers, we identified detectable levels of CSF-tDNA in 74% (95% CI 57 to 88%) of cases. All medulloblasomas, ependymomas, and high-grade gliomas that abutted a CSF space were detectable (100% of 21 cases, 95% CI 88% to 100%), while no CSF-tDNA was detected in patients whose tumors were not directly adjacent to a CSF reservoir ($p<0.0001$, Fisher's exact test).

Example 1

Materials and Methods
Patient Samples.
All samples were collected after approval was obtained from the Johns Hopkins Institutional Review Board and informed consent was provided. Whole blood and cerebrospinal fluid were collected at the time of surgery, prior to surgical manipulation of the tumor. A white blood cell (WBC) pellet was prepared from the blood sample after hypotonic lysis of red blood cells via centrifugation at 200 g. CSF was frozen in its entirety at −80° C. until DNA purification, and the entire volume of CSF (cells plus fluid) was used for DNA purification. The amount of CSF used averaged 4.8 ml (range 0.75 to 10 mL). When fresh tumor tissue from surgical specimen was available, it was immediately frozen at −80° C. When frozen tissue was not available, formalin-fixed, paraffin-embedded (FFPE) tissues were used for DNA purification. In either case (fresh-frozen or FFPE) tumors were macro-dissected to ensure neoplastic cellularity exceeding 50%. DNA was purified from the white cell pellet, CSF and tumor using an ALLPrep kit (Qiagen, cat #80204).

Statistical Analysis.
Clinical characteristics were compared between the CSF samples with and without detectable CSF-tDNA with Fisher's exact test or t-test. Correlation coefficients among outcomes were estimated using Pearson correlation statistics. A logistic regression model was used to estimate the odds of detecting CSF-tDNA under different conditions. All p-values are 2-sided and all analyses were conducted using SAS software (version 9.2, SAS Institute).

Tumor Mutational Profiling. A tiered approach was utilized to determine a somatic mutation within each tumor. Initially, a PCR-based approach testing for mutations in codons 130 to 139 of IDH1, codons 126 to 155, 144 to 178, and 250 to 262 of IDH2, all coding exons of TP53, and the TERT promoter was employed (44-48). If no mutations were present within these genes, paired-end libraries of DNA from the tumors and white blood cell pellets were prepared and captured (SureSelect, Agilent) as previous described (47). Massively parallel sequencing was carried out on an Illumina HiSeq instrument, either in the Goldman Sequencing Facility at Johns Hopkins Medical Institutions or at PGDx. Mutations were identified as previously described (47, 49-52).

Mutation Detection in CSF.

DNA from tumor, WBCs, and CSF was used to validate the somatic mutations identified by targeted sequencing and determine whether these mutations could be found in the CSF. Three to five nanogram (ng) of tumor and WBC DNA were used for each assay, while all DNA from the CSF (for cases with <20 ng of CSF DNA available) or 20 ng of CSF DNA was used for each assay (Table 2). For this purpose, primers were designed to amplify a ~100 bp region surrounding each mutation. The two primers had universal sequences at their 5'-ends allowing a second round of PCR to be performed using a second set of primers containing these sequences (19, 47). The sequences of the primers used to assess each mutation are listed in Table 5I. The final PCR products (after two rounds of PCR) were purified with AMPure (Beckman) and sequenced using an Illumina MiSeq instrument. The data were analyzed with the SafeSeqS pipeline, allowing mutations occurring as infrequently as 0.01% to be detected and quantified with confidence using the experimental conditions applied (19). In every case, DNA from the normal cells served as a control to ensure that the mutations were the result of errors generated during the DNA purification, amplification, or sequencing processes. Four paired-end libraries for CSF samples were also generated and exome captured (Table 4). Preparation of genomic library was performed using the TruSeq DNA Sample Prep Kit (Illumina) according to the manufacturer's recommendations. Exomic capture (SureSelect, Agilent) and massively parallel sequencing were carried out as described above.

Example 2

Patient and Tumor Characteristics.

Thirty-five patients with CNS cancers were enrolled in this study. Their age, gender, race, and pre-operative symptoms are listed in Table 1, together with their tumor characteristics. Six patients had medulloblastomas and twenty-nine had gliomas. Seven, nine, two, and seventeen of the tumors were classified as WHO Grades I, II, III, and IV, respectively. Twenty-nine (83%) of the 35 patients provided CSF during the initial surgery, while the remaining six (17%) did so during a repeat resection. The tumors were distributed throughout the brain and spinal cord, with fourteen arising in the posterior fossa (including six medulloblastomas), eight in the supratentorial compartment of the brain, and thirteen in the spinal cord (Table 1).

Example 3

Identification of Somatic Mutations.

At least one mutation was identified in each of the 35 tumors analyzed using a tiered approach (targeted sequencing followed by whole-exome sequencing) described in the Materials and Methods section.

With the targeted sequencing approach, we identified mutations in thirteen tumors. The mutations in these samples occurred in TP53 (n=5), IDH1 (n=2), and the TERT promoter (n=6) (Table 2). In the remaining 22 tumors, whole-exome sequencing was used to identifiy at least one mutation per sample. Genes mutated in these samples included well-known drivers, such as NF2, PIK3R1, PTCH1, and PTEN (18). The fractions of mutant alleles in tumors were generally high, averaging 46% (with standard deviation (SD) of 18%). This is consistent with the expected early development of driver gene mutations during tumor evolution and the presence of non-neoplastic cells in all tumors, even macrodissected ones such as the samples used here. All mutations identified were confirmed to be absent in DNA from matched non-cancerous ("normal") cells from each patient.

The presence of one of the mutations detected in each patient's tumor was then assessed in the CSF of the same patient using a sensitive, sequencing based method. This method reliably detects mutations with allele fractions as low as 0.01% (8, 19). An average of 4.8 mL of CSF (SD of 2.6) was collected from the 35 patients (Table 2). DNA could be purified from all CSF samples, though the amounts varied considerably (average of 417 ng, SD of 553 ng; Table 2). Primers were designed to amplify each of the 35 mutations as previously described (8, 19). Using this technology, we found that 74% of the 35 CSF samples contained detectable levels of tumor-derived DNA. The detectability of tumor DNA present in the CSF was not correlated with demographic characteristics, symptom duration, presence of hydrocephalus, contrast enhancement on imaging, or mutation type (Table 3a). The fraction of mutant alleles in the CSF was, as expected, usually lower than the fraction in the primary tumors, and was also much more variable than in the primary tumors. The average detectable mutant allele fraction in CSF was 12.2% (range 0.1% to 77%).

Example 4

Relationship Between Mutations and Clinical Features.

The great variation in mutant allele fraction among the CSF samples suggested that there might be some anatomical or biological factor underlying the differences. The tumors were distributed amongst the brain and spinal cord (Table 1) and malignancies arising in both organs were detected at similar frequencies (p=0.16; t-test). High-grade (WHO grade III-IV) tumors were more likely to have detectable CSF-tDNA than low-grade lesions (p=0.004; Table 3a), as evidenced by the fact that all but one high-grade tumor (18/19) was detected. The levels of CSF-tDNA were also higher in high-grade lesions than in low-grade lesions (mutant allele fractions of 16.3±21.2% vs. 2.8±6.8%). However, tumor size was not a statistically significant factor in predicting CSF-tDNA detectability or level (p=0.41; Table 3a).

Another important factor associated with CSF-tDNA levels was anatomic location. MRI scans were examined for the presence of contrast enhancement adjacent to a large CSF space (Table 1). Representative examples are provided in FIG. S1. Patients with lesions adjacent to a CSF reservoir in the brain or spinal cord were much more likely to have detectable levels of CSF-tDNA than the remaining lesions. Such reservoirs included the cortical surfaces, ventricles, as well as the basal and other cisterns. Accordingly, 86% of the 28 cases in which tumors were adjacent to CSF reservoir had detectable levels of CSF-tDNA. These cases included all 13 high-grade gliomas, all five ependymomas, and all five medulloblastomas that were in contact with the CSF. The four tumors in CSF contact that were not detectable were all low-grade gliomas. Moreover, none of the five patients whose tumors were entirely encapsulated by the brain or spinal cord parenchyma had detectable levels of CSF-tDNA (p<0.001, Table 3a). In addition, eighteen of the nineteen (~95%) high-grade (WHO grade III or IV) tumors had detectable levels of CSF-tDNA. Upon multivariate logistic regression, only the location of tumors with respect to CSF and the tumor grade were statistically significant (Table 3b).

Example 5

Genome-Wide Sequencing of DNA from the CSF.

The results described above were performed after identifying at least one mutation in the primary tumor of each patient. In four patients with either brainstem or intramedullary spinal cord tumors, we also tested whether CSF-tDNA could be detected directly in their CSF via whole-exome sequencing (WES) without prior knowledge of the tumor genotype. These four samples were selected based on the critical and highly sensitive location of the malignancies, making surgery treacherous. We found that two of the four cases analyzed had levels of CSF-tDNA that were comparable to the levels identified through single amplicon sequencing when the same mutation was assessed (Table 4). Both detectable cases had greater than 10% mutant allele fractions in the CSF as measured by single amplicon sequencing. (Table 4). In contrast, the two cases in which WES was unable to identify CSF-tDNA had mutant allele fractions <1% as assessed by single amplicon sequencing (Table 4). As controls, we also performed WES on matched normal tissue and tumor tissues. The mutations were found in the tumors at a high frequency but were absent in normal tissues (Table 4).

REFERENCES

The disclosure of each reference cited is expressly incorporated herein.
1. Ostrom Q T, et al. (2013) CBTRUS statistical report: Primary brain and central nervous system tumors diagnosed in the United States in 2006-2010. *Neuro Oncol* 15 Suppl 2:ii1-56.
2. Kros J M, et al. (2014) Circulating glioma biomarkers. *Neuro Oncol*.
3. Van Mieghem E, et al. (2013) Defining pseudoprogression in glioblastoma multiforme. *European journal of neurology: the official journal of the European Federation of Neurological Societies* 20(10):1335-1341.
4. Muller C, et al. (2014) Hematogenous dissemination of glioblastoma multiforme. *Sci Transl Med* 6(247): 247ra101.
5. Macarthur K M, et al. (2014) Detection of brain tumor cells in the peripheral blood by a telomerase promoter-based assay. *Cancer Res* 74(8):2152-2159.
6. Sullivan J P, et al. (2014) Brain tumor cells in circulation are enriched for mesenchymal gene expression. *Cancer Discov* 4(11):1299-1309.
7. Diehl F, et al. (2008) Circulating mutant DNA to assess tumor dynamics. *Nat Med* 14(9):985-990.
8. Bettegowda C, et al. (2014) Detection of circulating tumor DNA in early- and late-stage human malignancies. *Sci Transl Med* 6(224):224ra224.
9. Dawson S J, et al. (2013) Analysis of circulating tumor DNA to monitor metastatic breast cancer. *N Engl J Med* 368(13):1199-1209.
10. Newman A M, et al. (2014) An ultrasensitive method for quantitating circulating tumor DNA with broad patient coverage. *Nat Med* 20(5):548-554.
11. Martignetti J A, et al. (2014) Personalized ovarian cancer disease surveillance and detection of candidate therapeutic drug target in circulating tumor DNA. *Neoplasia* 16(1):97-103.
12. Sidransky D, et al. (1992) Identification of ras oncogene mutations in the stool of patients with curable colorectal tumors. *Science* 256(5053):102-105.
13. Sidransky D, et al. (1991) Identification of p53 gene mutations in bladder cancers and urine samples. *Science* 252(5006):706-709.
14. Ralla B, et al. (2014) Nucleic acid-based biomarkers in body fluids of patients with urologic malignancies. *Critical reviews in clinical laboratory sciences* 51(4):200-231.
15. Hubers A J, Prinsen C F, Sozzi G, Witte B I, & Thunnissen E (2013) Molecular sputum analysis for the diagnosis of lung cancer. *Br J Cancer* 109(3):530-537.
16. Diehl F, et al. (2008) Analysis of mutations in DNA isolated from plasma and stool of colorectal cancer patients. *Gastroenterology* 135(2):489-498.
17. Kinde I, et al. (2013) Evaluation of DNA from the Papanicolaou test to detect ovarian and endometrial cancers. *Sci Transl Med* 5(167):167ra164.
18. Vogelstein B, et al. (2013) Cancer genome landscapes. *Science* 339(6127):1546-1558.
19. Kinde I, Wu J, Papadopoulos N, Kinzler K W, & Vogelstein B (2012) Detection and quantification of rare mutations with massively parallel sequencing. *Proc Natl Acad Sci USA* 108(23):9530-9535.
20. Woodworth G F, et al. (2013) Histopathological correlates with survival in reoperated glioblastomas. *J Neurooncol* 113(3):485-493.
21. Krueger D A, et al. (2010) Everolimus for subependymal giant-cell astrocytomas in tuberous sclerosis. *N Engl J Med* 363(19):1801-1811.
22. Pan W, Gu W, Nagpal S, Gephart M H, & Quake S R (2015) Brain tumor mutations detected in cerebral spinal fluid. *Clin Chem* 61(3):514-522.
23. von Hoff K & Rutkowski S (2012) Medulloblastoma. *Current treatment options in neurology* 14(4):416-426.
24. Bartlett F, Kortmann R, & Saran F (2013) *Medulloblastoma. Clinical oncology* 25(1):36-45.
25. Glass J P, Melamed M, Chernik N L, & Posner J B (1979) Malignant cells in cerebrospinal fluid (CSF): the meaning of a positive CSF cytology. *Neurology* 29(10): 1369-1375.
26. Preusser M & Hainfellner J A (2012) CSF and laboratory analysis (tumor markers). *Handbook of clinical neurology* 104:143-148.
27. Allory Y, et al. (2014) Telomerase reverse transcriptase promoter mutations in bladder cancer: high frequency across stages, detection in urine, and lack of association with outcome. *Eur Urol* 65(2):360-366.
28. Destro A, et al. (2004) K-ras and p16(INK4A)alterations in sputum of NSCLC patients and in heavy asymptomatic chronic smokers. *Lung cancer* 44(1):23-32.
29. Mack S C, et al. (2014) Epigenomic alterations define lethal CIMP-positive ependymomas of infancy. *Nature* 506(7489):445-450.
30. Gajjar A, Pfister S M, Taylor M D, & Gilbertson R J (2014) Molecular insights into pediatric brain tumors have the potential to transform therapy. *Clin Cancer Res* 20(22):5630-5640.
31. Rudin C M, et al. (2009) Treatment of medulloblastoma with hedgehog pathway inhibitor GDC-0449. *N Engl J Med* 361(12):1173-1178.

32. Thompson M C, et al. (2006) Genomics identifies medulloblastoma subgroups that are enriched for specific genetic alterations. *J Clin Oncol* 24(12):1924-1931.
33. Moreno L, et al. (2010) Utility of cerebrospinal fluid cytology in newly diagnosed childhood ependymoma. *J Pediatr Hematol Oncol* 32(6):515-518.
34. Weston C L, Glantz M J, & Connor J R (2011) Detection of cancer cells in the cerebrospinal fluid: current methods and future directions. *Fluids and barriers of the CNS* 8(1):14.
35. Khwaja F W, et al. (2007) Proteomic identification of biomarkers in the cerebrospinal fluid (CSF) of astrocytoma patients. *J Proteome Res* 6(2):559-570.
36. Roy S, et al. (2008) Protein biomarker identification in the CSF of patients with CNS lymphoma. *J Clin Oncol* 26(1):96-105.
37. Bougel S, et al. (2013) Methylation of the hTERT promoter: a novel cancer biomarker for leptomeningeal metastasis detection in cerebrospinal fluids. *Clin Cancer Res* 19(8):2216-2223.
38. Samuel N, Remke M, Rutka JT, Raught B, & Malkin D (2014) Proteomic analyses of CSF aimed at biomarker development for pediatric brain tumors. *J Neurooncol* 118(2):225-238.
39. Chamberlain M C, Kormanik P A, & Glantz M J (2001) A comparison between ventricular and lumbar cerebrospinal fluid cytology in adult patients with leptomeningeal metastases. *Neuro Oncol* 3(1):42-45.
40. Gajjar A, et al. (1999) Comparison of lumbar and shunt cerebrospinal fluid specimens for cytologic detection of leptomeningeal disease in pediatric patients with brain tumors. *J Clin Oncol* 17(6):1825-1828.
41. Thomas L, Di Stefano A L, & Ducray F (2013) Predictive biomarkers in adult gliomas: the present and the future. *Curr Opin Oncol* 25(6):689-694.
42. Olar A & Aldape K D (2014) Using the molecular classification of glioblastoma to inform personalized treatment. *J Pathol* 232(2):165-177.
43. Gajjar A J & Robinson G W (2014) Medulloblastoma-translating discoveries from the bench to the bedside. *Nat Rev Clin Oncol*.
44. Horn S, et al. (2013) TERT promoter mutations in familial and sporadic melanoma. *Science* 339(6122):959-961.
45. Huang F W, et al. (2013) Highly recurrent TERT promoter mutations in human melanoma. *Science* 339 (6122):957-959.
46. Killela P J, et al. (2013) TERT promoter mutations occur frequently in gliomas and a subset of tumors derived from cells with low rates of self-renewal. *Proc Natl Acad Sci USA* 110(15):6021-6026.
47. Bettegowda C, et al. (2013) Exomic sequencing of four rare central nervous system tumor types. *Oncotarget* 4(4):572-583.
48. Kinde I, et al. (2013) TERT promoter mutations occur early in urothelial neoplasia and are biomarkers of early disease and disease recurrence in urine. *Cancer Res* 73(24):7162-7167.
49. Zhang M, et al. (2014) Somatic mutations of SUZ12 in malignant peripheral nerve sheath tumors. *Nat Genet* 46(11):1170-1172.
50. Agrawal N, et al. (2011) Exome Sequencing of Head and Neck Squamous Cell Carcinoma Reveals Inactivating Mutations in NOTCH1. *Science*.
51. Agrawal N, et al. (2012) Comparative Genomic Analysis of Esophageal Adenocarcinoma and Squamous Cell Carcinoma. *Cancer Discov* 2(10):899-905.
52. Bettegowda C, et al. (2011) Mutations in CIC and FUBP1 contribute to human oligodendroglioma. *Science* 333(6048):1453-1455.

We claim:

1. A method comprising:
   a) receiving a Cerebral Spinal Fluid (CSF) sample from a human with a primary brain tumor, wherein said primary brain tumor is a glioma, a medulloblastoma, or an ependymoma and has been determined by imaging to abut a CSF reservoir, wherein the CSF reservoir is a ventricular reservoir or a basal cistern;
   b) assaying tumor-specific DNA shed from said primary brain tumor in said CSF sample and determining the presence of one or more point mutations in said tumor-specific DNA; and
   c) assaying nucleic acids from a normal tissue from the human and determining absence of the one or more point mutations determined to be present in said tumor-specific DNA.

2. The method of claim 1, further comprising the step of assaying nucleic acids in a tissue sample from said primary brain tumor from the human and determining the one or more point mutations.

3. The method of claim 2, wherein the step of assaying the nucleic acids in the tissue sample from said primary brain tumor is performed prior to the step of assaying said tumor-specific DNA in the CSF sample.

4. The method of claim 2, wherein the step of assaying the nucleic acids in the tissue sample from said primary brain tumor is performed using genome-wide screening.

5. The method of claim 2, wherein the step of assaying the nucleic acids in the tissue sample from said primary brain tumor is performed using exome-wide screening.

6. The method of claim 1, wherein the human has previously been subjected to surgical removal of the primary brain tumor.

7. The method of claim 1, wherein steps a) and b) are repeated using CSF samples collected from the human at different times.

8. The method of claim 1, wherein the step of assaying in step b) employs a specific probe or a specific primer to detect the one or more point mutations, wherein the specific probe or the specific primer hybridizes at or within 200 nucleotides of the point mutation.

9. The method of claim 8, wherein the specific probe is employed.

10. The method of claim 8, wherein the specific primer is employed.

11. The method of claim 1, wherein nested amplification reactions are used to detect the one or more point mutations.

12. The method of claim 1, wherein the one or more point mutations comprise a point mutation in TERT promoter.

13. The method of claim 1, wherein the primary brain tumor is a glioma.

14. The method of claim 1, wherein the primary brain tumor is a medulloblastoma.

15. The method of claim 1, wherein the primary brain tumor is an ependymoma.

* * * * *

```
                        SEQUENCE LISTING

<160> NUMBER OF SEQ ID NOS: 70

<210> SEQ ID NO 1
<211> LENGTH: 46
<212> TYPE: DNA
<213> ORGANISM: Artificial Sequence
<220> FEATURE:
<223> OTHER INFORMATION: Synthetic primers

<400> SEQUENCE: 1
cacacaggaa acagctatga ccatgcttca ggtggctcga gtagtg              46

<210> SEQ ID NO 2
<211> LENGTH: 45
<212> TYPE: DNA
<213> ORGANISM: Artificial Sequence
<220> FEATURE:
<223> OTHER INFORMATION: Synthetic primers

<400> SEQUENCE: 2
cacacaggaa acagctatga ccatgtttct tttgcctgca ggatt               45

<210> SEQ ID NO 3
<211> LENGTH: 48
<212> TYPE: DNA
<213> ORGANISM: Artificial Sequence
<220> FEATURE:
<223> OTHER INFORMATION: Synthetic primers
```

<400> SEQUENCE: 3
cacacaggaa acagctatga ccatgtggac aatgtggaga taaaggac    48

<210> SEQ ID NO 4
<211> LENGTH: 43
<212> TYPE: DNA
<213> ORGANISM: Artificial Sequence
<220> FEATURE:
<223> OTHER INFORMATION: Synthetic primers

<400> SEQUENCE: 4
cacacaggaa acagctatga ccatgctggt cctgcctcac tcg    43

<210> SEQ ID NO 5
<211> LENGTH: 45
<212> TYPE: DNA
<213> ORGANISM: Artificial Sequence
<220> FEATURE:
<223> OTHER INFORMATION: Synthetic primers

<400> SEQUENCE: 5
cacacaggaa acagctatga ccatggaagc aaacagctcg caagt    45

<210> SEQ ID NO 6
<211> LENGTH: 44
<212> TYPE: DNA
<213> ORGANISM: Artificial Sequence
<220> FEATURE:
<223> OTHER INFORMATION: Synthetic primers

<400> SEQUENCE: 6
cacacaggaa acagctatga ccatggccag ctgttgctga ccta    44

<210> SEQ ID NO 7
<211> LENGTH: 45
<212> TYPE: DNA
<213> ORGANISM: Artificial Sequence
<220> FEATURE:
<223> OTHER INFORMATION: Synthetic primers

<400> SEQUENCE: 7
cacacaggaa acagctatga ccatgagacc tcaggcggct catag    45

<210> SEQ ID NO 8
<211> LENGTH: 45
<212> TYPE: DNA
<213> ORGANISM: Artificial Sequence
<220> FEATURE:
<223> OTHER INFORMATION: Synthetic primers

<400> SEQUENCE: 8
cacacaggaa acagctatga ccatggagtg gttggggagg acatt    45

<210> SEQ ID NO 9
<211> LENGTH: 43
<212> TYPE: DNA
<213> ORGANISM: Artificial Sequence
<220> FEATURE:
<223> OTHER INFORMATION: Synthetic primers

<400> SEQUENCE: 9
cacacaggaa acagctatga ccatgctgtc aaggcgggct tct    43

<210> SEQ ID NO 10
<211> LENGTH: 45

-continued

```
<212> TYPE: DNA
<213> ORGANISM: Artificial Sequence
<220> FEATURE:
<223> OTHER INFORMATION: Synthetic primers

<400> SEQUENCE: 10
cacacaggaa acagctatga ccatgatcgg gcagtgatag agcag           45

<210> SEQ ID NO 11
<211> LENGTH: 45
<212> TYPE: DNA
<213> ORGANISM: Artificial Sequence
<220> FEATURE:
<223> OTHER INFORMATION: Synthetic primers

<400> SEQUENCE: 11
cacacaggaa acagctatga ccatggaagc ctctgattgg cacag           45

<210> SEQ ID NO 12
<211> LENGTH: 55
<212> TYPE: DNA
<213> ORGANISM: Artificial Sequence
<220> FEATURE:
<223> OTHER INFORMATION: Synthetic primers

<400> SEQUENCE: 12
cacacaggaa acagctatga ccatggcttg tgagtggatg ggtaaaacct atcat   55

<210> SEQ ID NO 13
<211> LENGTH: 55
<212> TYPE: DNA
<213> ORGANISM: Artificial Sequence
<220> FEATURE:
<223> OTHER INFORMATION: Synthetic primers

<400> SEQUENCE: 13
cacacaggaa acagctatga ccatggcttg tgagtggatg ggtaaaacct atcat   55

<210> SEQ ID NO 14
<211> LENGTH: 53
<212> TYPE: DNA
<213> ORGANISM: Artificial Sequence
<220> FEATURE:
<223> OTHER INFORMATION: Synthetic primers

<400> SEQUENCE: 14
cacacaggaa acagctatga ccatgtccac tacaactaca tgtgtaacag ttc     53

<210> SEQ ID NO 15
<211> LENGTH: 42
<212> TYPE: DNA
<213> ORGANISM: Artificial Sequence
<220> FEATURE:
<223> OTHER INFORMATION: Synthetic primers

<400> SEQUENCE: 15
cacacaggaa acagctatga ccatggcgga aaggaagggg ag              42

<210> SEQ ID NO 16
<211> LENGTH: 42
<212> TYPE: DNA
<213> ORGANISM: Artificial Sequence
<220> FEATURE:
<223> OTHER INFORMATION: Synthetic primers

<400> SEQUENCE: 16
```
cacacaggaa acagctatga ccatggcgga aaggaagggg ag                42

<210> SEQ ID NO 17
<211> LENGTH: 47
<212> TYPE: DNA
<213> ORGANISM: Artificial Sequence
<220> FEATURE:
<223> OTHER INFORMATION: Synthetic primers

<400> SEQUENCE: 17
cacacaggaa acagctatga ccatgtggct ctgactgtac caccatc          47

<210> SEQ ID NO 18
<211> LENGTH: 44
<212> TYPE: DNA
<213> ORGANISM: Artificial Sequence
<220> FEATURE:
<223> OTHER INFORMATION: Synthetic primers

<400> SEQUENCE: 18
cacacaggaa acagctatga ccatgcggaa atgtgggagg agag             44

<210> SEQ ID NO 19
<211> LENGTH: 45
<212> TYPE: DNA
<213> ORGANISM: Artificial Sequence
<220> FEATURE:
<223> OTHER INFORMATION: Synthetic primers

<400> SEQUENCE: 19
cacacaggaa acagctatga ccatgccagc acctatggca agttt            45

<210> SEQ ID NO 20
<211> LENGTH: 47
<212> TYPE: DNA
<213> ORGANISM: Artificial Sequence
<220> FEATURE:
<223> OTHER INFORMATION: Synthetic primers

<400> SEQUENCE: 20
cacacaggaa acagctatga ccatggccct gactttcaac tctgtct          47

<210> SEQ ID NO 21
<211> LENGTH: 45
<212> TYPE: DNA
<213> ORGANISM: Artificial Sequence
<220> FEATURE:
<223> OTHER INFORMATION: Synthetic primers

<400> SEQUENCE: 21
cacacaggaa acagctatga ccatggtcca acgtgccata tccat            45

<210> SEQ ID NO 22
<211> LENGTH: 44
<212> TYPE: DNA
<213> ORGANISM: Artificial Sequence
<220> FEATURE:
<223> OTHER INFORMATION: Synthetic primers

<400> SEQUENCE: 22
cacacaggaa acagctatga ccatgccttg tggcaccctg ggtc             44

<210> SEQ ID NO 23
<211> LENGTH: 44
<212> TYPE: DNA
<213> ORGANISM: Artificial Sequence

```
<220> FEATURE:
<223> OTHER INFORMATION: Synthetic primers

<400> SEQUENCE: 23
cacacaggaa acagctatga ccatgggaag ttgatccgct caca            44

<210> SEQ ID NO 24
<211> LENGTH: 42
<212> TYPE: DNA
<213> ORGANISM: Artificial Sequence
<220> FEATURE:
<223> OTHER INFORMATION: Synthetic primers

<400> SEQUENCE: 24
cacacaggaa acagctatga ccatggcgga aaggaagggg ag              42

<210> SEQ ID NO 25
<211> LENGTH: 42
<212> TYPE: DNA
<213> ORGANISM: Artificial Sequence
<220> FEATURE:
<223> OTHER INFORMATION: Synthetic primers

<400> SEQUENCE: 25
cacacaggaa acagctatga ccatggcgga aaggaagggg ag              42

<210> SEQ ID NO 26
<211> LENGTH: 42
<212> TYPE: DNA
<213> ORGANISM: Artificial Sequence
<220> FEATURE:
<223> OTHER INFORMATION: Synthetic primers

<400> SEQUENCE: 26
cacacaggaa acagctatga ccatggcgga aaggaagggg ag              42

<210> SEQ ID NO 27
<211> LENGTH: 42
<212> TYPE: DNA
<213> ORGANISM: Artificial Sequence
<220> FEATURE:
<223> OTHER INFORMATION: Synthetic primers

<400> SEQUENCE: 27
cacacaggaa acagctatga ccatggcgga aaggaagggg ag              42

<210> SEQ ID NO 28
<211> LENGTH: 48
<212> TYPE: DNA
<213> ORGANISM: Artificial Sequence
<220> FEATURE:
<223> OTHER INFORMATION: Synthetic primers

<400> SEQUENCE: 28
cacacaggaa acagctatga ccatggcaat tcactgtaaa gctggaaa        48

<210> SEQ ID NO 29
<211> LENGTH: 46
<212> TYPE: DNA
<213> ORGANISM: Artificial Sequence
<220> FEATURE:
<223> OTHER INFORMATION: Synthetic primers

<400> SEQUENCE: 29
cacacaggaa acagctatga ccatgtctga cataaaccag gccaac          46
```

<210> SEQ ID NO 30
<211> LENGTH: 44
<212> TYPE: DNA
<213> ORGANISM: Artificial Sequence
<220> FEATURE:
<223> OTHER INFORMATION: Synthetic primers

<400> SEQUENCE: 30
cacacaggaa acagctatga ccatgccgag tcctgggagt tttg                         44

<210> SEQ ID NO 31
<211> LENGTH: 45
<212> TYPE: DNA
<213> ORGANISM: Artificial Sequence
<220> FEATURE:
<223> OTHER INFORMATION: Synthetic primers

<400> SEQUENCE: 31
cacacaggaa acagctatga ccatgcgagg cactgcggta ttaag                        45

<210> SEQ ID NO 32
<211> LENGTH: 45
<212> TYPE: DNA
<213> ORGANISM: Artificial Sequence
<220> FEATURE:
<223> OTHER INFORMATION: Synthetic primers

<400> SEQUENCE: 32
cacacaggaa acagctatga ccatgacagc cagtcgactc tgagg                        45

<210> SEQ ID NO 33
<211> LENGTH: 49
<212> TYPE: DNA
<213> ORGANISM: Artificial Sequence
<220> FEATURE:
<223> OTHER INFORMATION: Synthetic primers

<400> SEQUENCE: 33
cacacaggaa acagctatga ccatgaatgg aacaaacaat gataagcaa                    49

<210> SEQ ID NO 34
<211> LENGTH: 53
<212> TYPE: DNA
<213> ORGANISM: Artificial Sequence
<220> FEATURE:
<223> OTHER INFORMATION: Synthetic primers

<400> SEQUENCE: 34
cacacaggaa acagctatga ccatgtccac tacaactaca tgtgtaacag ttc               53

<210> SEQ ID NO 35
<211> LENGTH: 55
<212> TYPE: DNA
<213> ORGANISM: Artificial Sequence
<220> FEATURE:
<223> OTHER INFORMATION: Synthetic primers

<400> SEQUENCE: 35
cacacaggaa acagctatga ccatgactca catgttgatt tgacttacta atgta             55

<210> SEQ ID NO 36
<211> LENGTH: 52
<212> TYPE: DNA
<213> ORGANISM: Artificial Sequence
<220> FEATURE:
<223> OTHER INFORMATION: Synthetic primers -continued

```
<221> NAME/KEY: misc_feature
<222> LOCATION: (1)...(52)
<223> OTHER INFORMATION: n = A,T,C or G

<400> SEQUENCE: 36
cgacgtaaaa cgacggccag tnnnnnnnnn nnnnngtgag gggccgtgtt gt            52

<210> SEQ ID NO 37
<211> LENGTH: 57
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(57)
<223> OTHER INFORMATION: n = A,T,C or G

<400> SEQUENCE: 37
cgacgtaaaa cgacggccag tnnnnnnnnn nnnnncctga attgtagcaa tcaccaa       57

<210> SEQ ID NO 38
<211> LENGTH: 58
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(58)
<223> OTHER INFORMATION: n = A,T,C or G

<400> SEQUENCE: 38
cgacgtaaaa cgacggccag tnnnnnnnnn nnnnnccacc agtggaaata agaacaga      58

<210> SEQ ID NO 39
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 39
cgacgtaaaa cgacggccag tnnnnnnnnn nnnnntccct cccctagaag gtctg         55

<210> SEQ ID NO 40
<211> LENGTH: 54
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(54)
<223> OTHER INFORMATION: n = A,T,C or G

<400> SEQUENCE: 40
cgacgtaaaa cgacggccag tnnnnnnnnn nnnnngcggt agcgatgagg tttc          54

<210> SEQ ID NO 41
<211> LENGTH: 56
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(56)
<223> OTHER INFORMATION: n = A,T,C or G
```

<400> SEQUENCE: 41
cgacgtaaaa cgacggccag tnnnnnnnnn nnnnnagagt cctttctcct gctgct       56

<210> SEQ ID NO 42
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 42
cgacgtaaaa cgacggccag tnnnnnnnnn nnnnnttgcg tgtggagtat ttgga        55

<210> SEQ ID NO 43
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 43
cgacgtaaaa cgacggccag tnnnnnnnnn nnnnngttcc ccatttgagg tctcg        55

<210> SEQ ID NO 44
<211> LENGTH: 52
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(52)
<223> OTHER INFORMATION: n = A,T,C or G

<400> SEQUENCE: 44
cgacgtaaaa cgacggccag tnnnnnnnnn nnnnngcagc acgagggtca gg           52

<210> SEQ ID NO 45
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 45
cgacgtaaaa cgacggccag tnnnnnnnnn nnnnntcatt gggtgttacg cttcc        55

<210> SEQ ID NO 46
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 46
cgacgtaaaa cgacggccag tnnnnnnnnn nnnnnagcag gcataggaac atcca        55

<210> SEQ ID NO 47
<211> LENGTH: 65
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(65)
<223> OTHER INFORMATION: n = A,T,C or G

<400> SEQUENCE: 47
cgacgtaaaa cgacggccag tnnnnnnnnn nnnnnatgca aaatcacatt attgccaaca    60
tgact                                                               65

<210> SEQ ID NO 48
<211> LENGTH: 65
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(65)
<223> OTHER INFORMATION: n = A,T,C or G

<400> SEQUENCE: 48
cgacgtaaaa cgacggccag tnnnnnnnnn nnnnnatgca aaatcacatt attgccaaca    60
tgact                                                               65

<210> SEQ ID NO 49
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 49
cgacgtaaaa cgacggccag tnnnnnnnnn nnnnntgtga tgatggtgag gatgg         55

<210> SEQ ID NO 50
<211> LENGTH: 50
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(50)
<223> OTHER INFORMATION: n = A,T,C or G

<400> SEQUENCE: 50
cgacgtaaaa cgacggccag tnnnnnnnnn nnnnncccgt cccgacccct                50

<210> SEQ ID NO 51
<211> LENGTH: 50
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(50)
<223> OTHER INFORMATION: n = A,T,C or G

<400> SEQUENCE: 51
cgacgtaaaa cgacggccag tnnnnnnnnn nnnnncccgt cccgacccct                50

```
<210> SEQ ID NO 52
<211> LENGTH: 53
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(53)
<223> OTHER INFORMATION: n = A,T,C or G

<400> SEQUENCE: 52
cgacgtaaaa cgacggccag tnnnnnnnnn nnnnngtggc aagtggctcc tga          53

<210> SEQ ID NO 53
<211> LENGTH: 59
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(59)
<223> OTHER INFORMATION: n = A,T,C or G

<400> SEQUENCE: 53
cgacgtaaaa cgacggccag tnnnnnnnnn nnnnnaaagc ccataaagga atgtaaacc    59

<210> SEQ ID NO 54
<211> LENGTH: 53
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(53)
<223> OTHER INFORMATION: n = A,T,C or G

<400> SEQUENCE: 54
cgacgtaaaa cgacggccag tnnnnnnnnn nnnncggga tggcttgaag aga           53

<210> SEQ ID NO 55
<211> LENGTH: 53
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(53)
<223> OTHER INFORMATION: n = A,T,C or G

<400> SEQUENCE: 55
cgacgtaaaa cgacggccag tnnnnnnnnn nnnnnggggg tgtggaatca acc          53

<210> SEQ ID NO 56
<211> LENGTH: 53
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(53)
<223> OTHER INFORMATION: n = A,T,C or G

<400> SEQUENCE: 56
cgacgtaaaa cgacggccag tnnnnnnnnn nnnnnggtgg ggagtgggac tca          53

<210> SEQ ID NO 57
<211> LENGTH: 55
<212> TYPE: DNA
```

```
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 57
cgacgtaaaa cgacggccag tnnnnnnnnn nnnnngttca gcctcctccc tcatc          55

<210> SEQ ID NO 58
<211> LENGTH: 56
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(56)
<223> OTHER INFORMATION: n = A,T,C or G

<400> SEQUENCE: 58
cgacgtaaaa cgacggccag tnnnnnnnnn nnnnncatca gatacaacgc caccat         56

<210> SEQ ID NO 59
<211> LENGTH: 50
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(50)
<223> OTHER INFORMATION: n = A,T,C or G

<400> SEQUENCE: 59
cgacgtaaaa cgacggccag tnnnnnnnnn nnnnncccgt cccgacccct                50

<210> SEQ ID NO 60
<211> LENGTH: 50
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(50)
<223> OTHER INFORMATION: n = A,T,C or G

<400> SEQUENCE: 60
cgacgtaaaa cgacggccag tnnnnnnnnn nnnnncccgt cccgacccct                50

<210> SEQ ID NO 61
<211> LENGTH: 50
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(50)
<223> OTHER INFORMATION: n = A,T,C or G

<400> SEQUENCE: 61
cgacgtaaaa cgacggccag tnnnnnnnnn nnnnncccgt cccgacccct                50

<210> SEQ ID NO 62
<211> LENGTH: 50
<212> TYPE: DNA
<213> ORGANISM: Artificial Sequence
<220> FEATURE:
<223> OTHER INFORMATION: Synthetic primers
<221> NAME/KEY: misc_feature
```

<222> LOCATION: (1)...(50)
<223> OTHER INFORMATION: n = A,T,C or G

<400> SEQUENCE: 62
cgacgtaaaa cgacggccag tnnnnnnnnn nnnnncccgt cccgacccct         50

<210> SEQ ID NO 63
<211> LENGTH: 57
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(57)
<223> OTHER INFORMATION: n = A,T,C or G

<400> SEQUENCE: 63
cgacgtaaaa cgacggccag tnnnnnnnnn nnnntggtc cttacttccc catagaa    57

<210> SEQ ID NO 64
<211> LENGTH: 56
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(56)
<223> OTHER INFORMATION: n = A,T,C or G

<400> SEQUENCE: 64
cgacgtaaaa cgacggccag tnnnnnnnnn nnnnnaccag gtcttcgtaa gcatga    56

<210> SEQ ID NO 65
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 65
cgacgtaaaa cgacggccag tnnnnnnnnn nnnntacag ctgaggggag gagaa      55

<210> SEQ ID NO 66
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 66
cgacgtaaaa cgacggccag tnnnnnnnnn nnnntgggt cttcctcctc ctctg      55

<210> SEQ ID NO 67
<211> LENGTH: 53
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(53)
<223> OTHER INFORMATION: n = A,T,C or G

<400> SEQUENCE: 67

```
cgacgtaaaa cgacggccag tnnnnnnnnn nnnnnatctg actccgccga ttg        53

<210> SEQ ID NO 68
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 68
cgacgtaaaa cgacggccag tnnnnnnnnn nnnnnggaag gggcgaaatt acagt      55

<210> SEQ ID NO 69
<211> LENGTH: 55
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(55)
<223> OTHER INFORMATION: n = A,T,C or G

<400> SEQUENCE: 69
cgacgtaaaa cgacggccag tnnnnnnnnn nnnnntgtga tgatggtgag gatgg      55

<210> SEQ ID NO 70
<211> LENGTH: 58
<212> TYPE: DNA
<213> ORGANISM: Artificial Sequence
<220> FEATURE:
<223> OTHER INFORMATION: Synthetic primers
<221> NAME/KEY: misc_feature
<222> LOCATION: (1)...(58)
<223> OTHER INFORMATION: n = A,T,C or G

<400> SEQUENCE: 70
cgacgtaaaa cgacggccag tnnnnnnnnn nnnnnacagt acaaaatgga ggacctga   58
```